United States Patent
Oda et al.

(10) Patent No.: US 9,980,696 B2
(45) Date of Patent: May 29, 2018

(54) RADIOGRAPHIC IMAGE CAPTURING APPARATUS, RADIOGRAPHIC IMAGE CAPTURING SYSTEM, CONTROL METHOD OF RADIOGRAPHIC IMAGE CAPTURING APPARATUS, AND CONTROL PROGRAM OF RADIOGRAPHIC IMAGE CAPTURING APPARATUS

(71) Applicant: FUJIFILM Corporation, Tokyo (JP)

(72) Inventors: Yasufumi Oda, Kanagawa (JP); Jun Enomoto, Kanagawa (JP); Ryou Imamura, Kanagawa (JP); Takashi Tajima, Kanagawa (JP); Kentaro Noma, Kanagawa (JP); Takeshi Kuwabara, Kanagawa (JP); Tetsuya Tsuji, Kanagawa (JP); Hiroaki Yasuda, Kanagawa (JP); Haruyasu Nakatsugawa, Kanagawa (JP); Takeshi Koishi, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 161 days.

(21) Appl. No.: 15/016,348

(22) Filed: Feb. 5, 2016

(65) Prior Publication Data

US 2016/0228087 A1 Aug. 11, 2016

(30) Foreign Application Priority Data

Feb. 10, 2015 (JP) .................. 2015-024698
Oct. 23, 2015 (JP) .................. 2015-209215

(51) Int. Cl.
*H05G 1/58* (2006.01)
*A61B 6/00* (2006.01)

(52) U.S. Cl.
CPC .............. *A61B 6/54* (2013.01); *A61B 6/465* (2013.01); *A61B 6/467* (2013.01); *A61B 6/5211* (2013.01); *A61B 6/542* (2013.01)

(58) Field of Classification Search
CPC .. A61B 6/00; A61B 6/46; A61B 6/461; A61B 6/464; A61B 6/5211; A61B 6/54
(Continued)

(56) References Cited

U.S. PATENT DOCUMENTS

2015/0181629 A1* 6/2015 Jun .................. H04W 76/021
455/420

FOREIGN PATENT DOCUMENTS

| JP | 2012-045179 A | 3/2012 |
|---|---|---|
| JP | 2013-111402 A | 6/2013 |
| JP | 2013-141484 A | 7/2013 |

* cited by examiner

*Primary Examiner* — Jurie Yun
(74) *Attorney, Agent, or Firm* — Sughrue Mion, PLLC

(57) ABSTRACT

Disclosed is a technique capable of enhancing usability of a radiographic image capturing apparatus, system, control method of the radiographic image capturing apparatus and a non-transitory computer readable recording medium recorded with a control program, for a user. A radiographic image capturing apparatus includes: an I/F unit and an imaging control unit that function as a communication unit that selectively performs communication with any one of a portable information terminal and a console which are plural control apparatuses that have different image processing capacities with respect to a radiographic image and respectively perform a control relating to capturing of the radiographic image; and an imaging control unit that functions as a selection unit that selects any one of plural imaging modes predetermined with respect to the capturing of the radio-
(Continued)

graphic image according to the image processing capacity of the control apparatus that performs communication with the communication unit.

22 Claims, 42 Drawing Sheets

(58) Field of Classification Search
USPC .......................................... 378/114, 115, 116
See application file for complete search history.

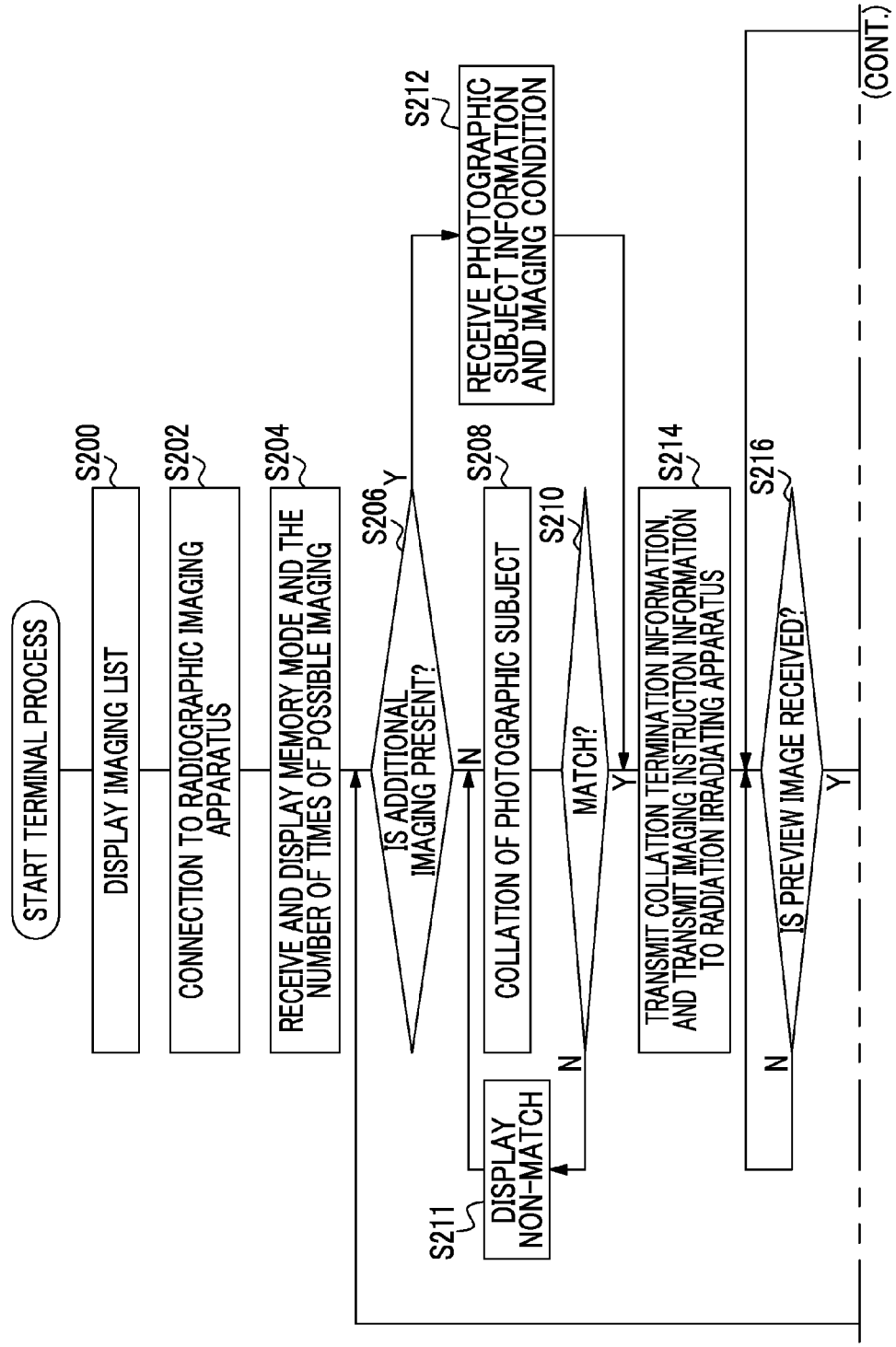

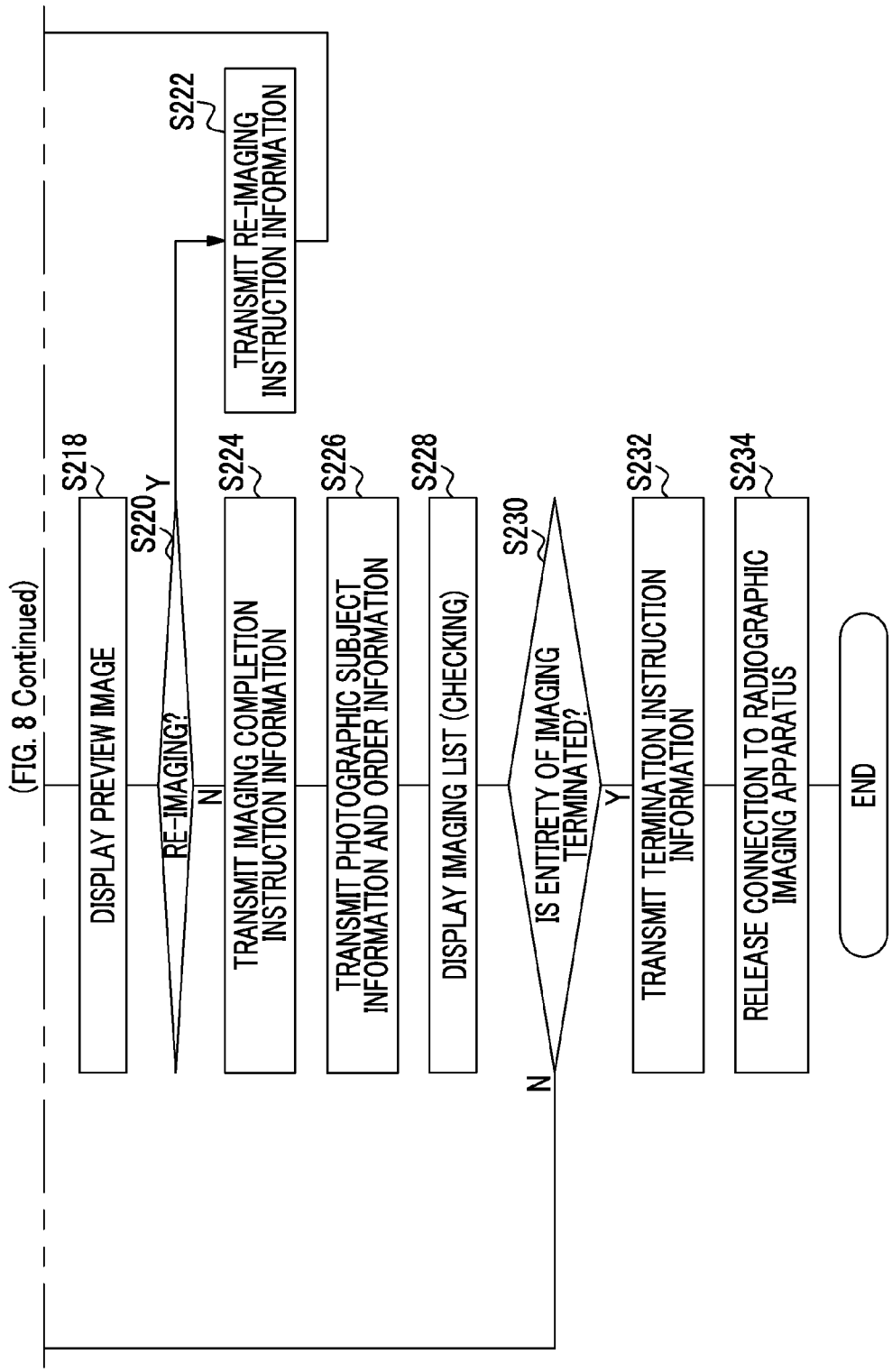

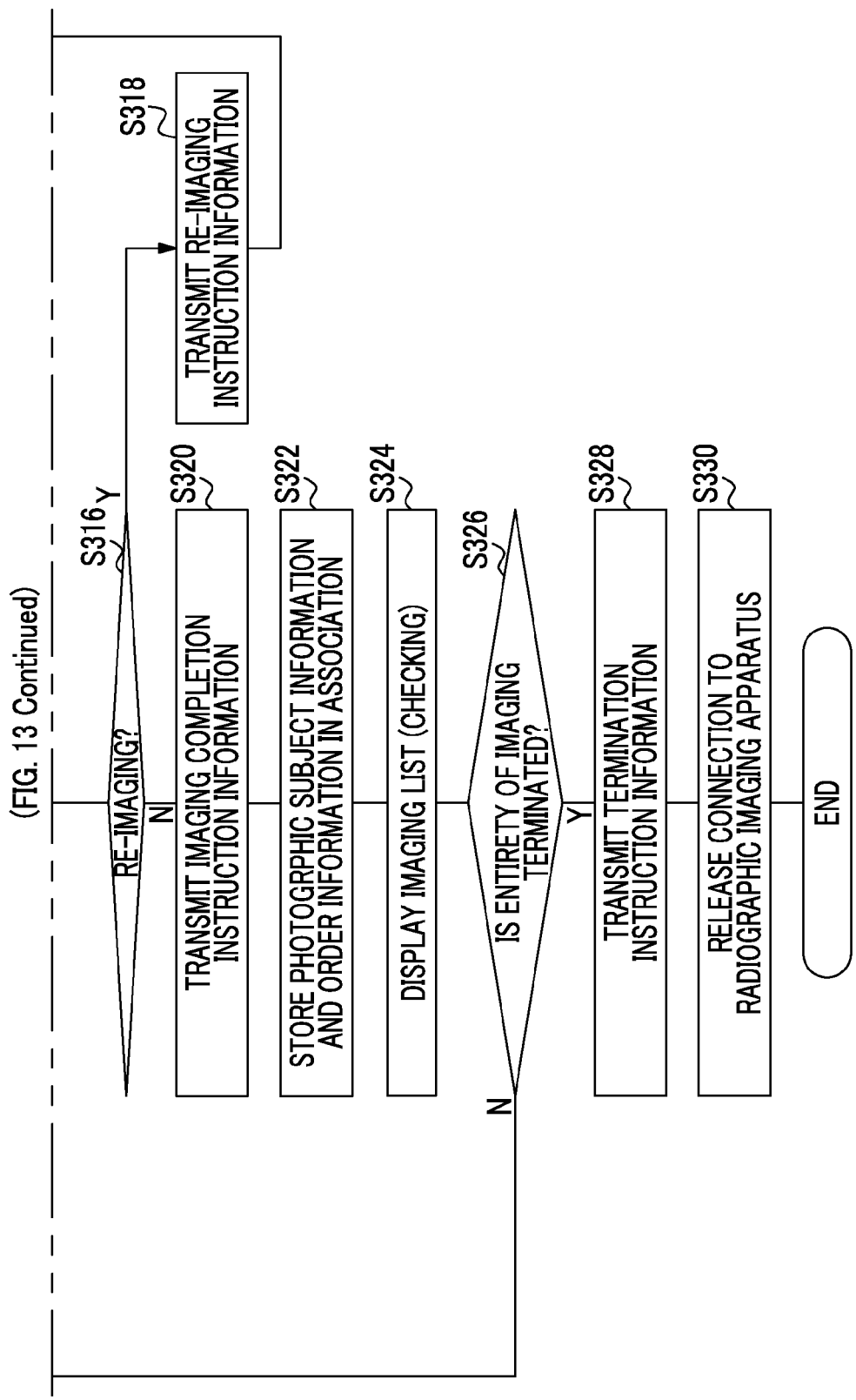

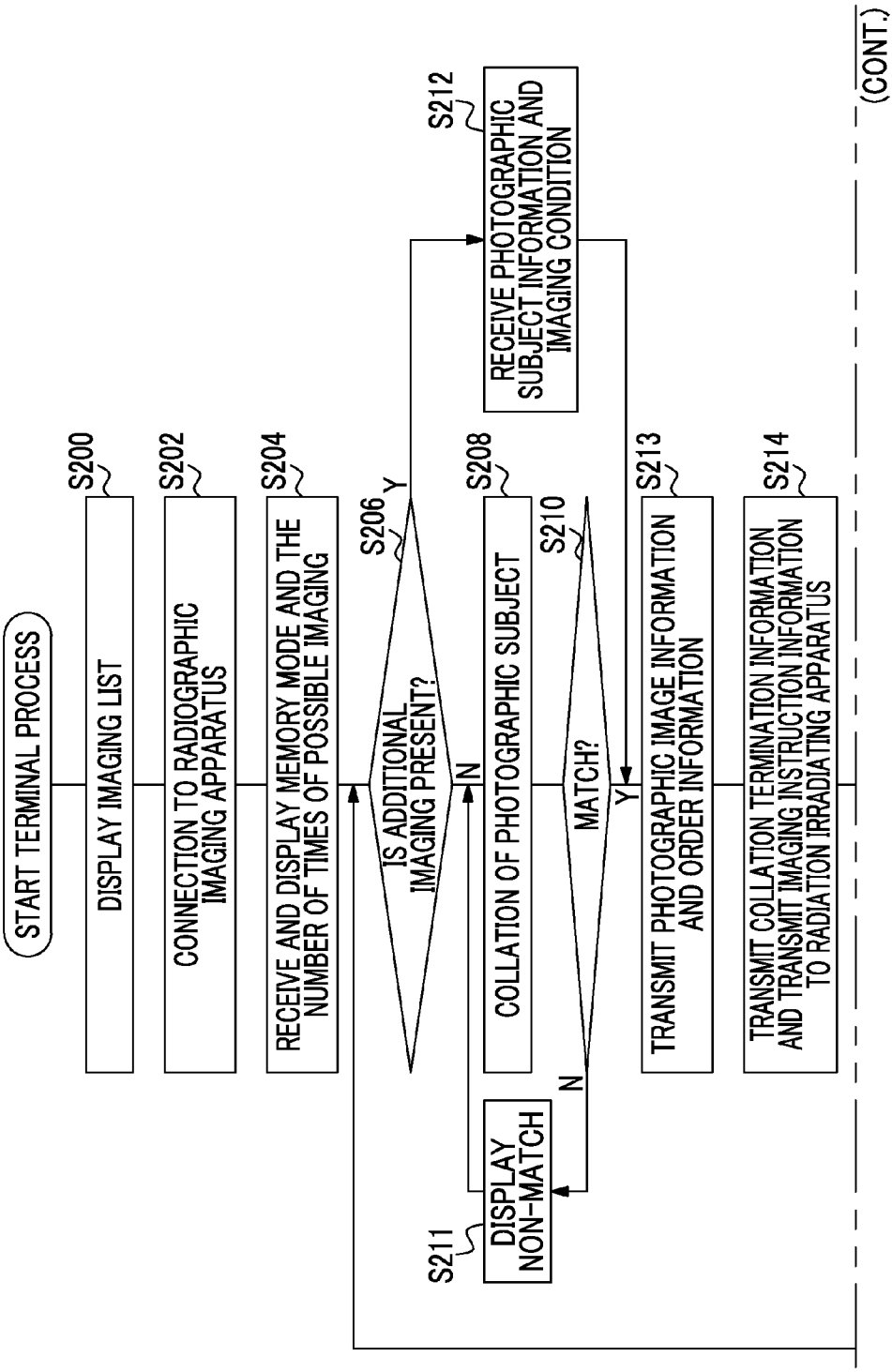

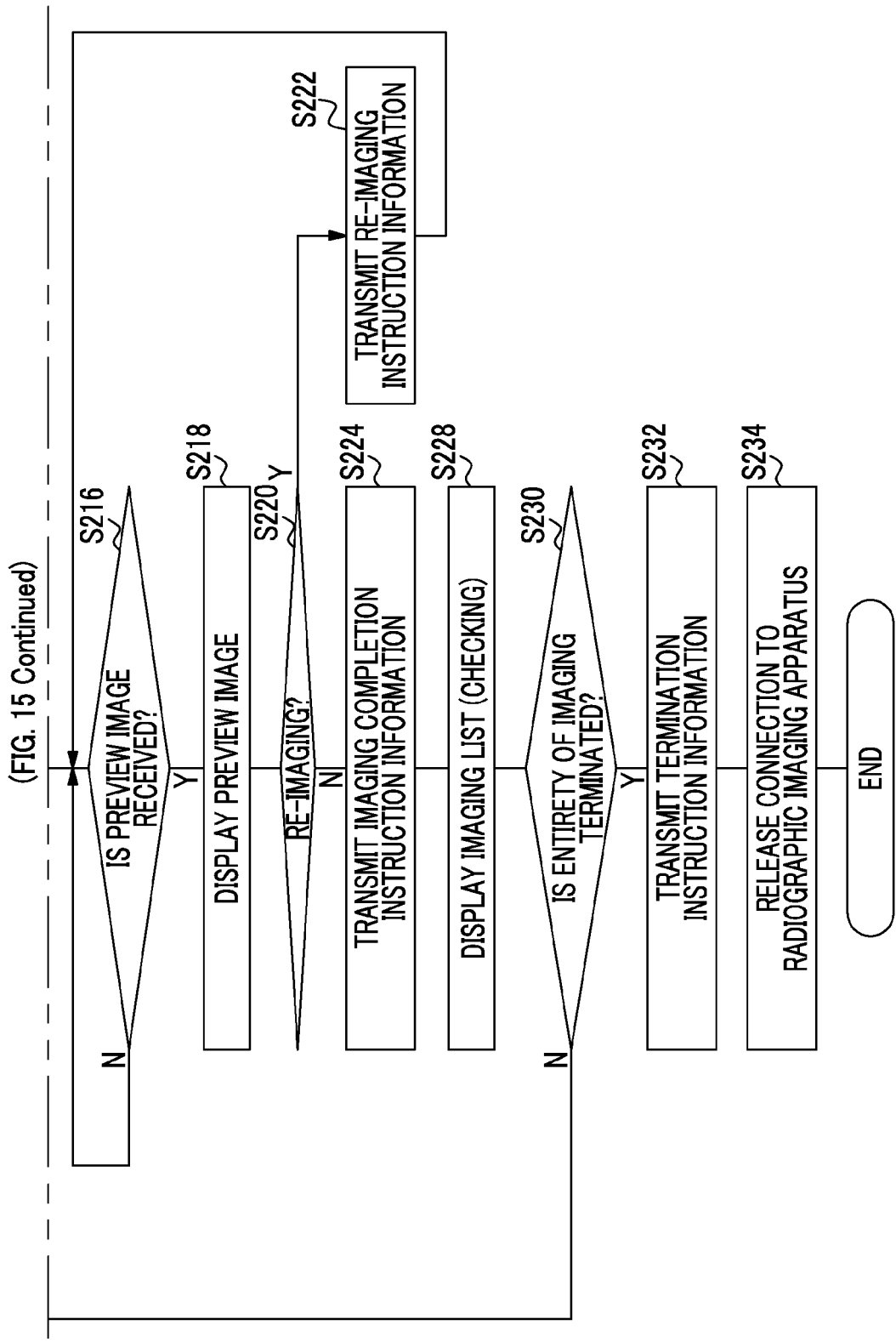

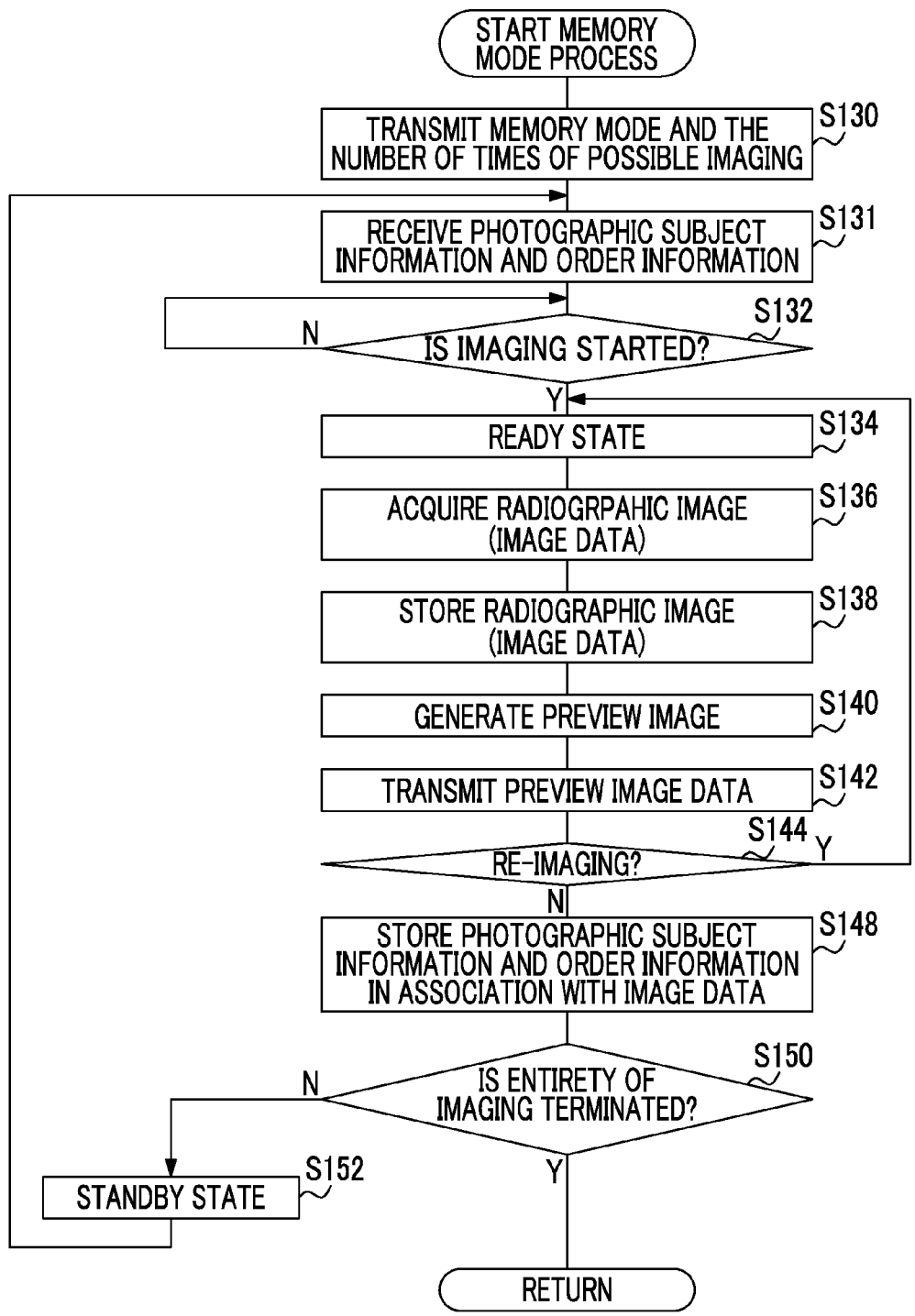

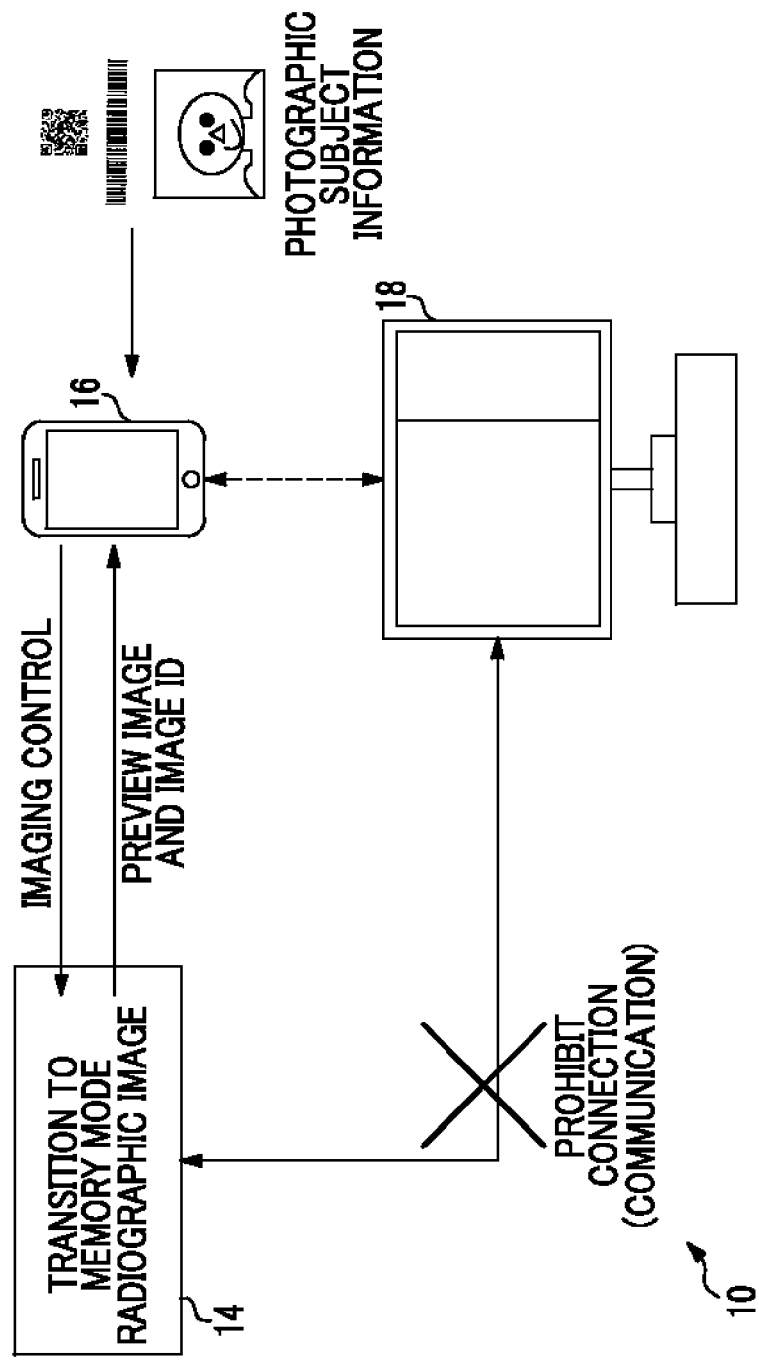

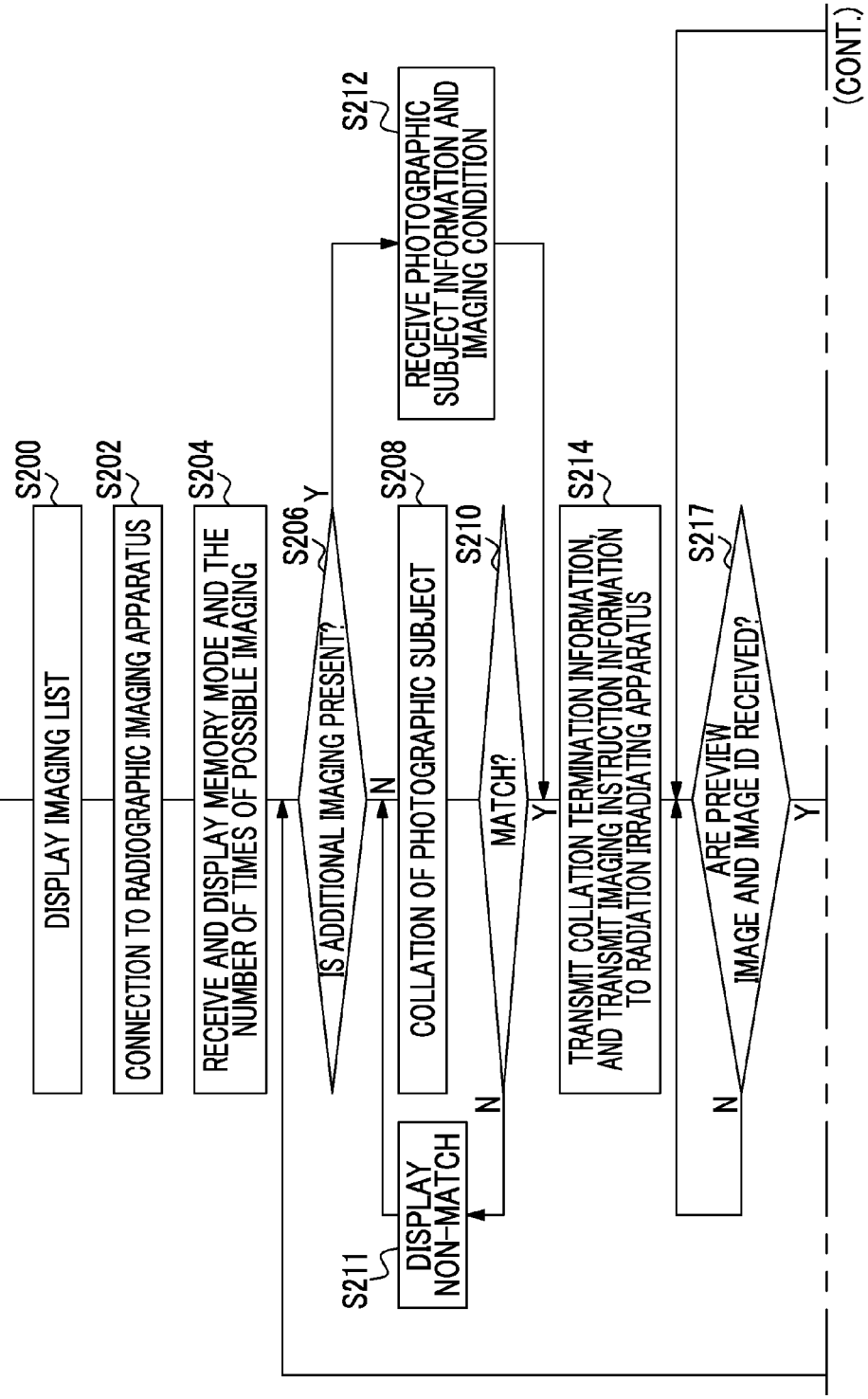

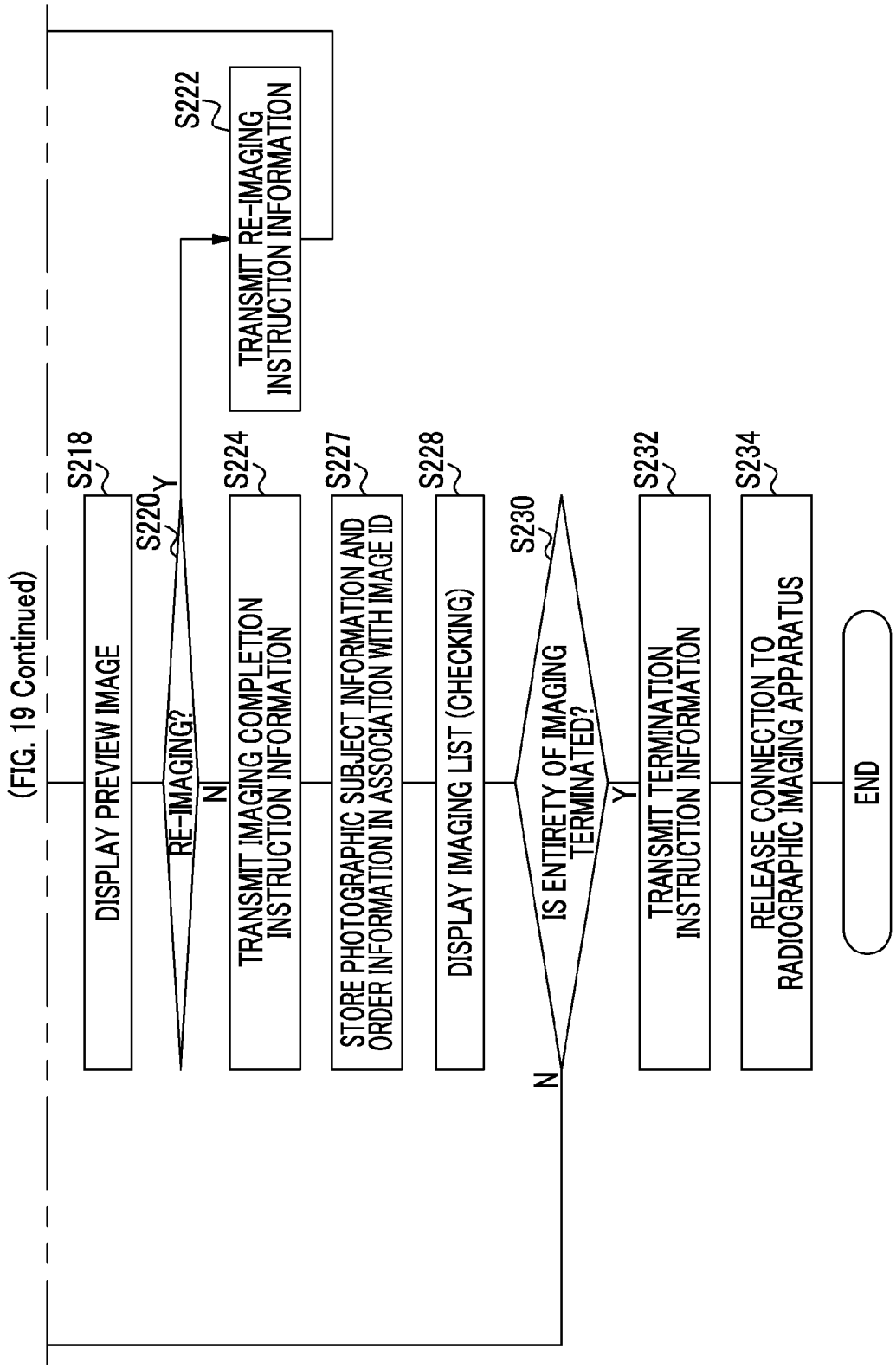

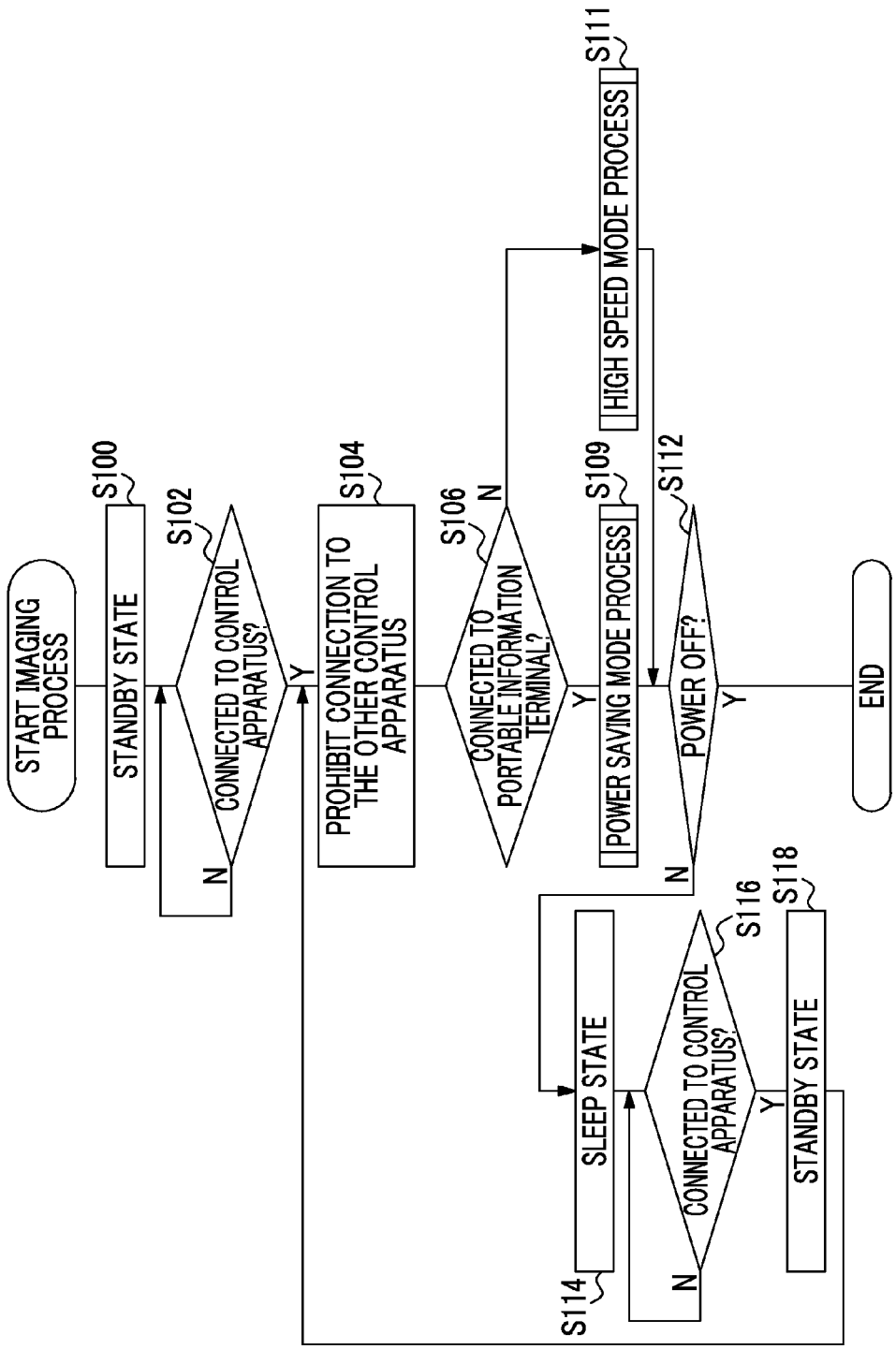

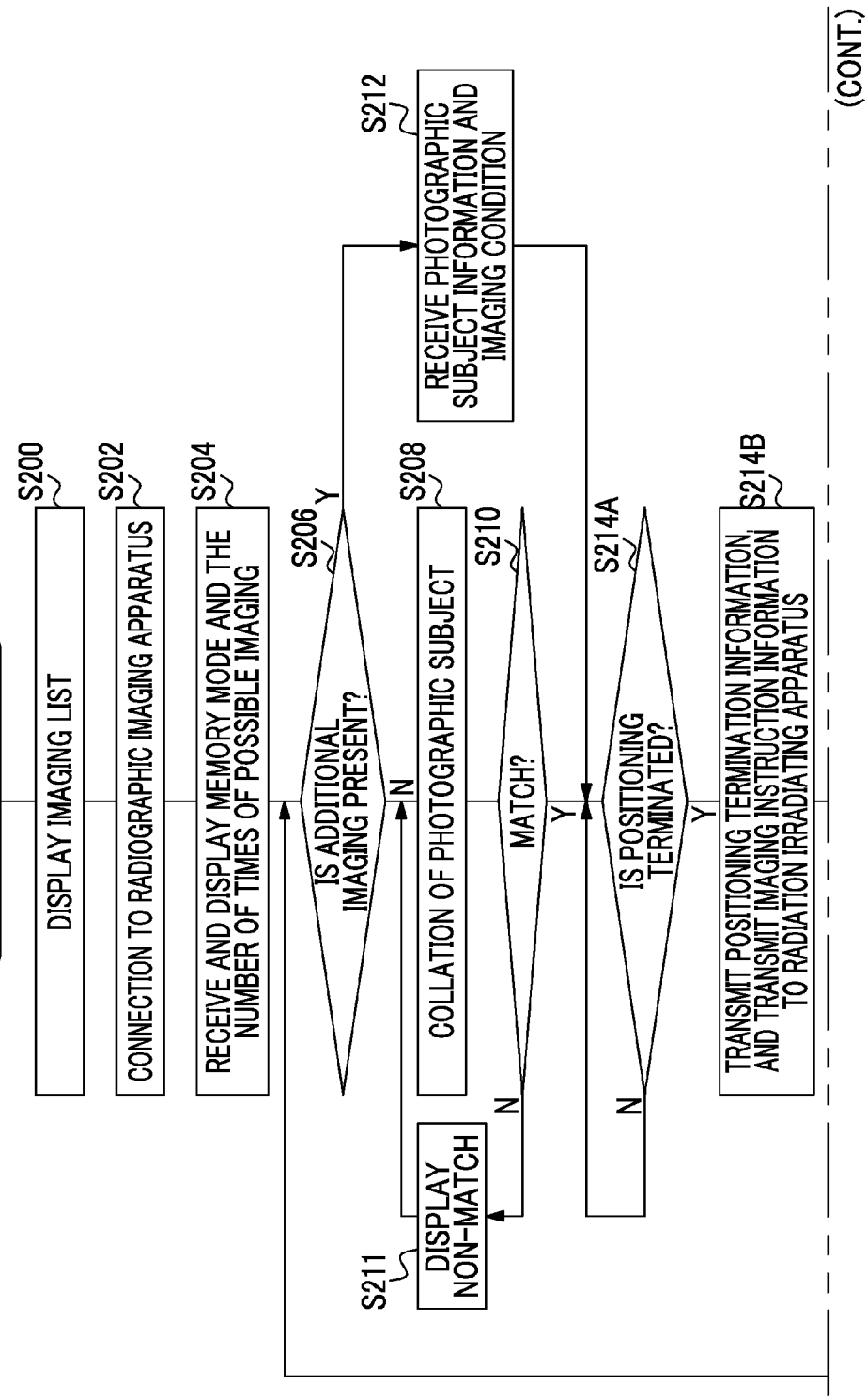

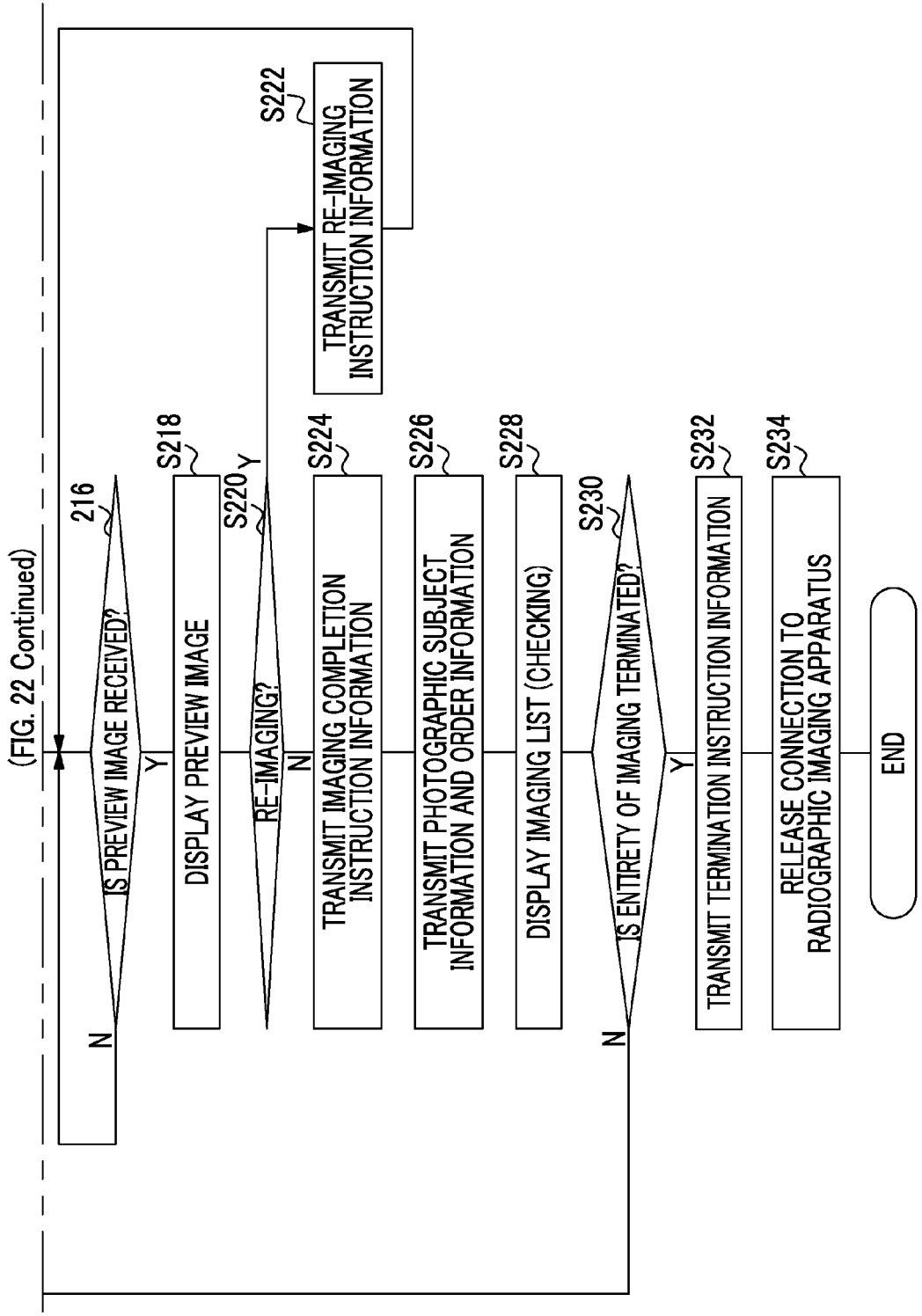

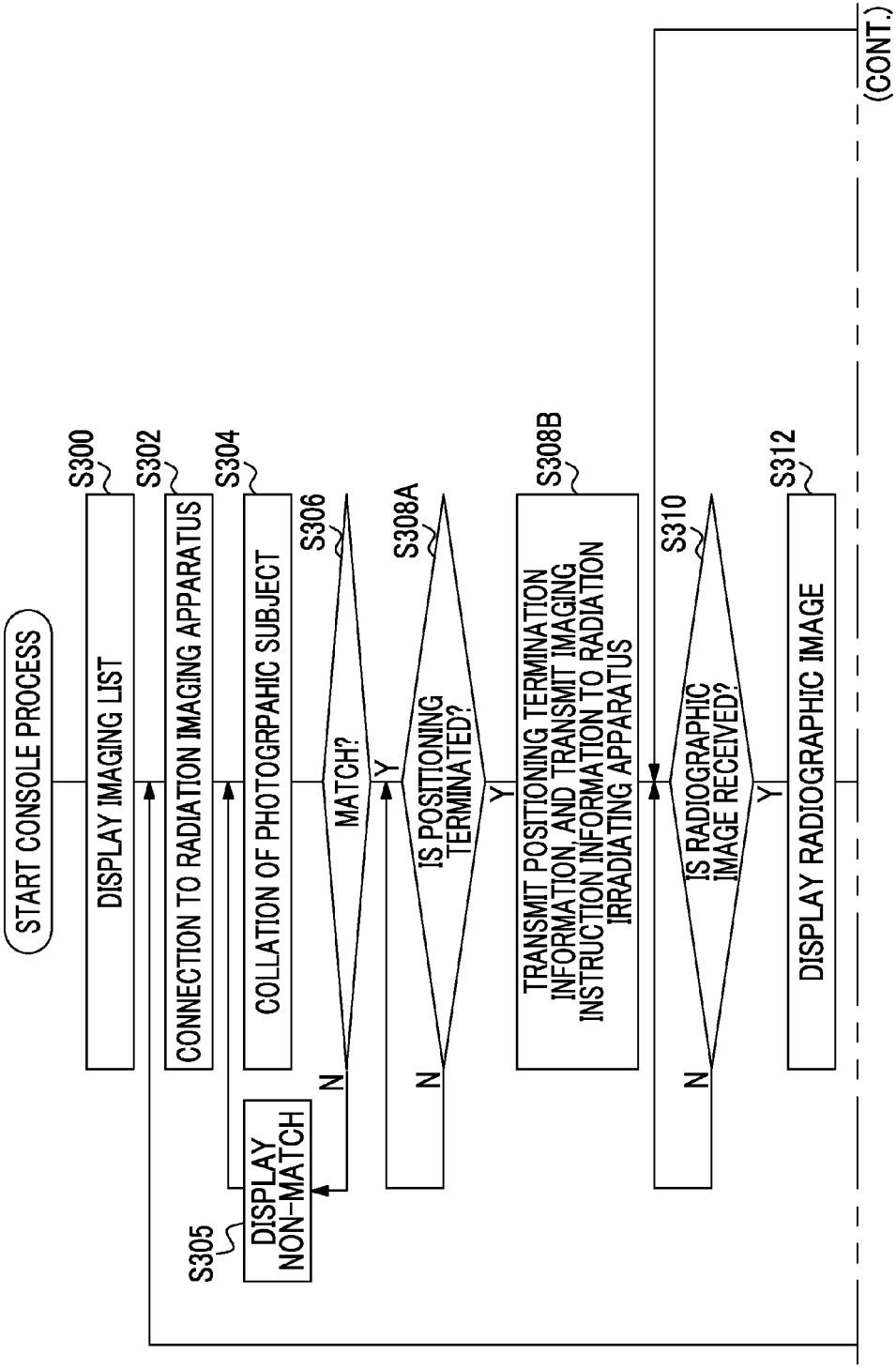

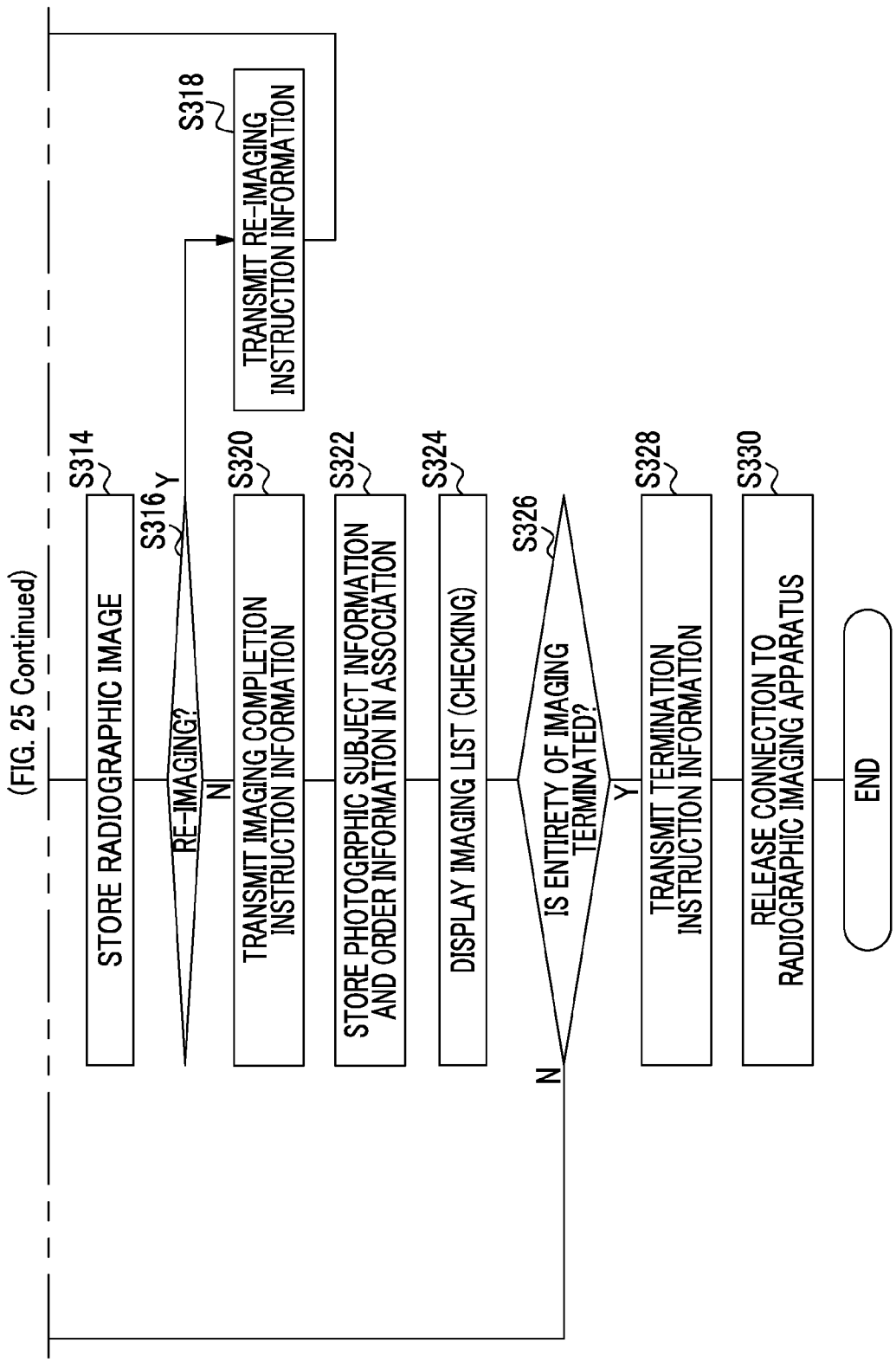

FIG. 28

| HARDWARE | SOFTWARE | DISPLAY IMAGE QUALITY A>B>C N: NO IMAGE |
|---|---|---|
| LAPTOP | FOR CONSOLE | A |
| LAPTOP | OsiriX | B |
| TABLET LARGE SCREEN | FOR CONSOLE | A |
| TABLET SMALL SCREEN | OsiriX | B |
| TABLET SMALL SCREEN | EASY VIEWER | C |
| TABLET LARGE SCREEN | NO RADIOGRAPHIC IMAGE (NO PROCESSING SOFTWARE AND NO IMAGE DISPLAY) | N |

TABLET: LARGE SCREEN IS EQUAL TO OR GREATER THAN 9-INCH (CORRESPONDING TO DIAGONAL LENGTH OF 23 cm), AND SMALL SCREEN IS SMALLER THAN 9-INCH

FIG. 29

| | APPLICABLE COMMUNICATION METHOD |
|---|---|
| CONTROL APPARATUS 1 | WiFi<br>Bluetooth<br>IrDa |
| CONTROL APPARATUS 2 | WiFi<br>Bluetooth<br>IrDa |
| CONTROL APPARATUS 3 | WiFi<br>Bluetooth<br>NFC |
| CONTROL APPARATUS 4 | WiFi<br>Bluetooth<br>NFC |
| CONTROL APPARATUS 5 | WiFi<br>Bluetooth<br>NFC |
| CONTROL APPARATUS 6 | WiFi<br>Bluetooth<br>NFC |

OTHER COMMUNICATION METHODS : Wi-Fi
MIMO (Multiple Input Multiple Output)

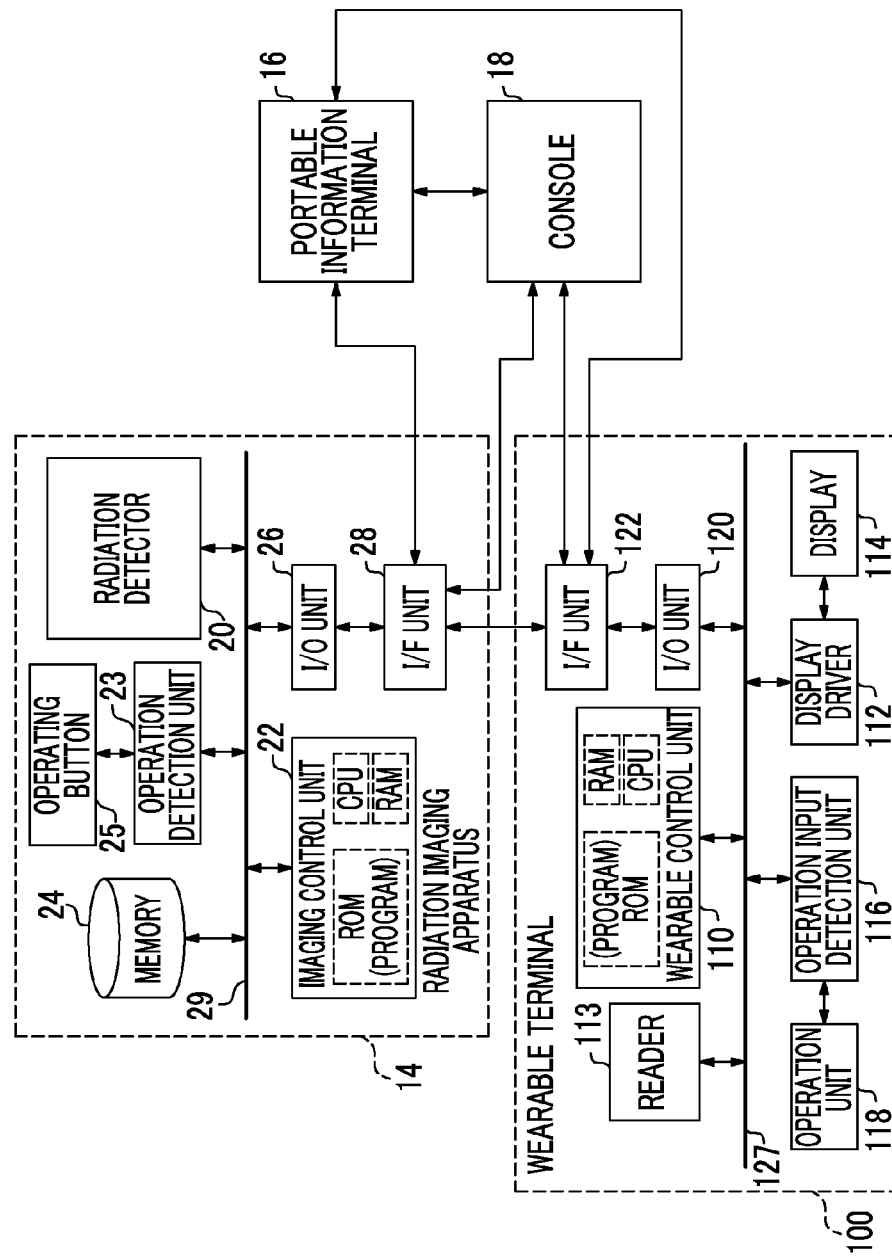

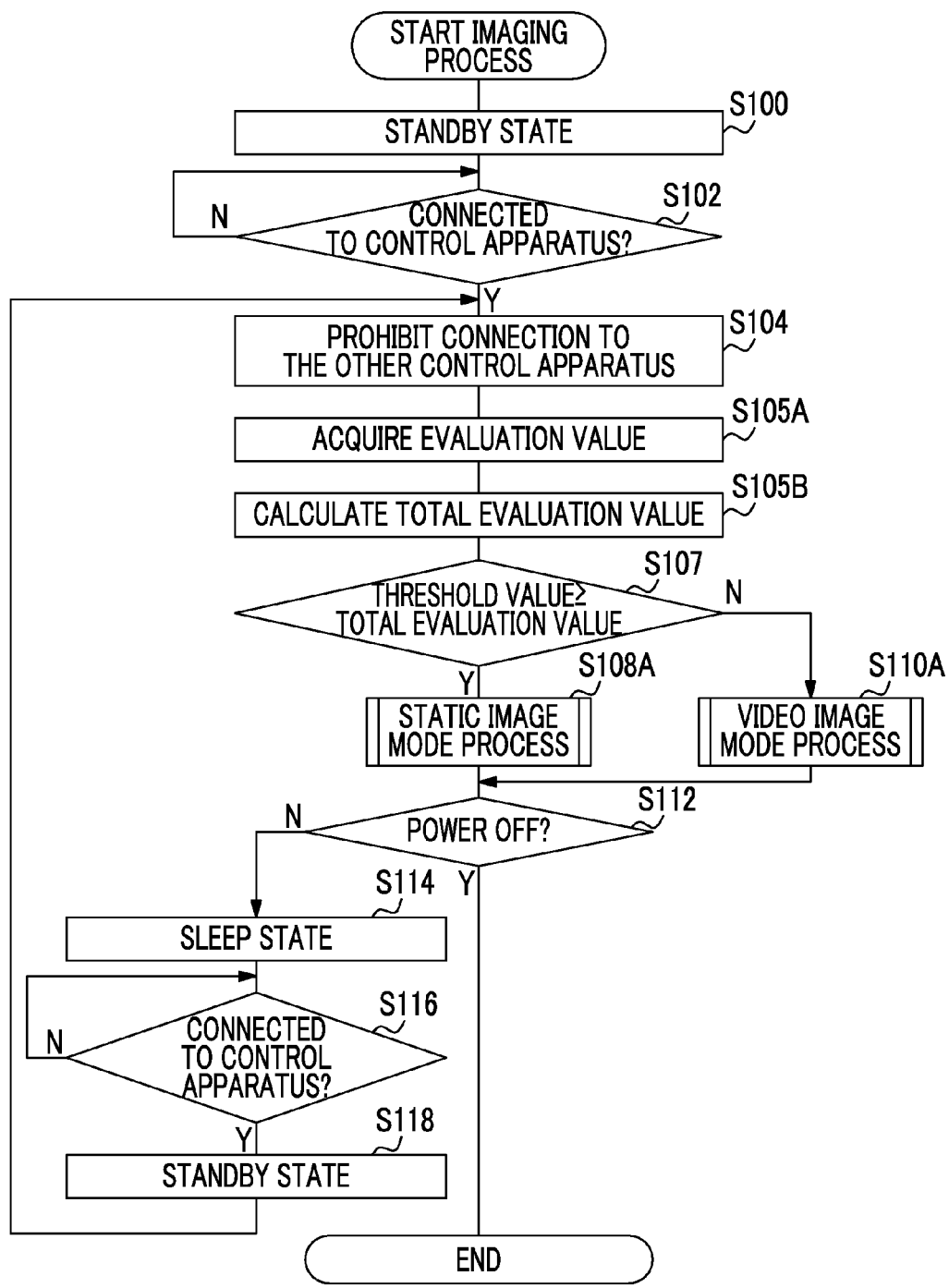

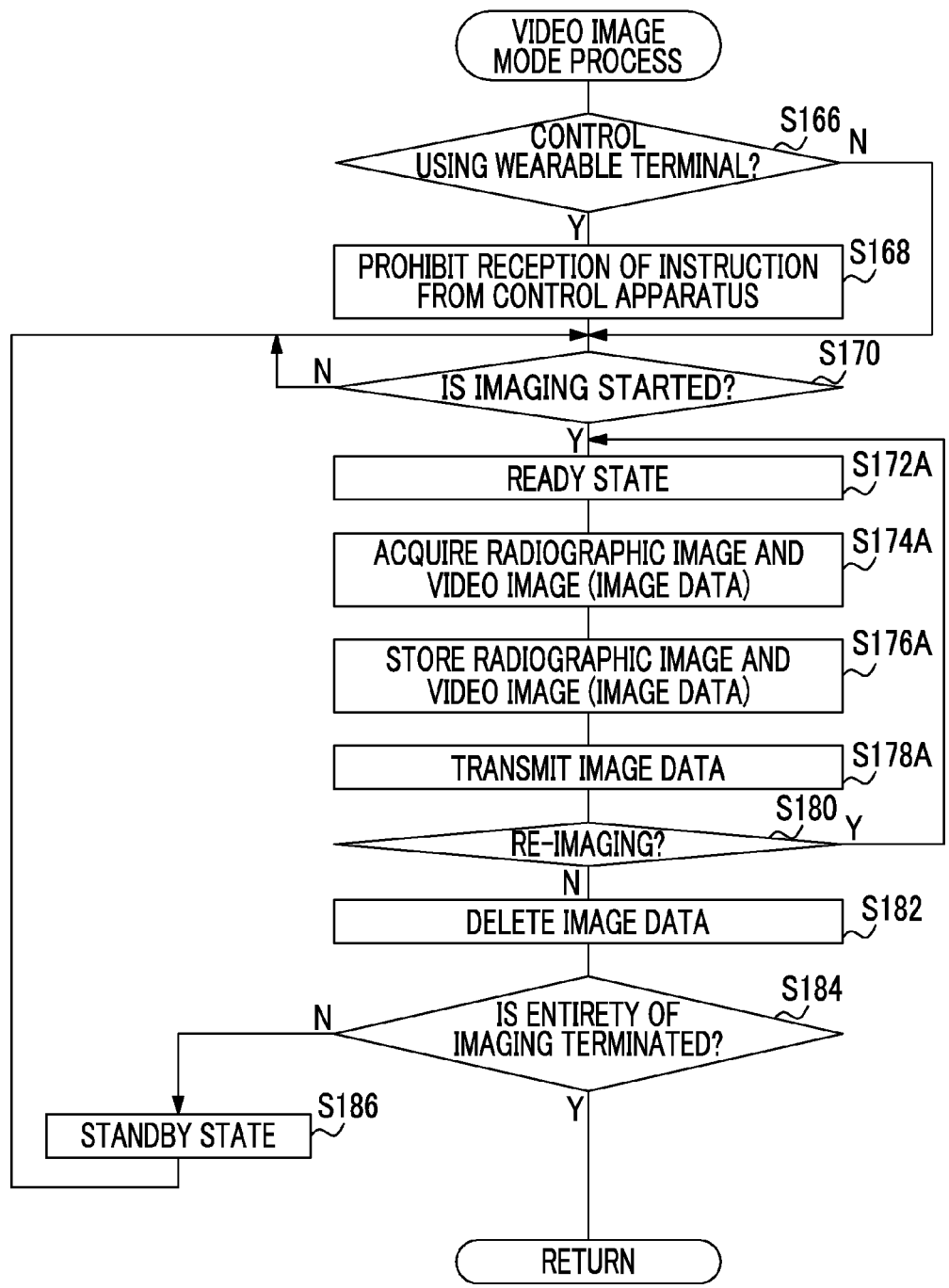

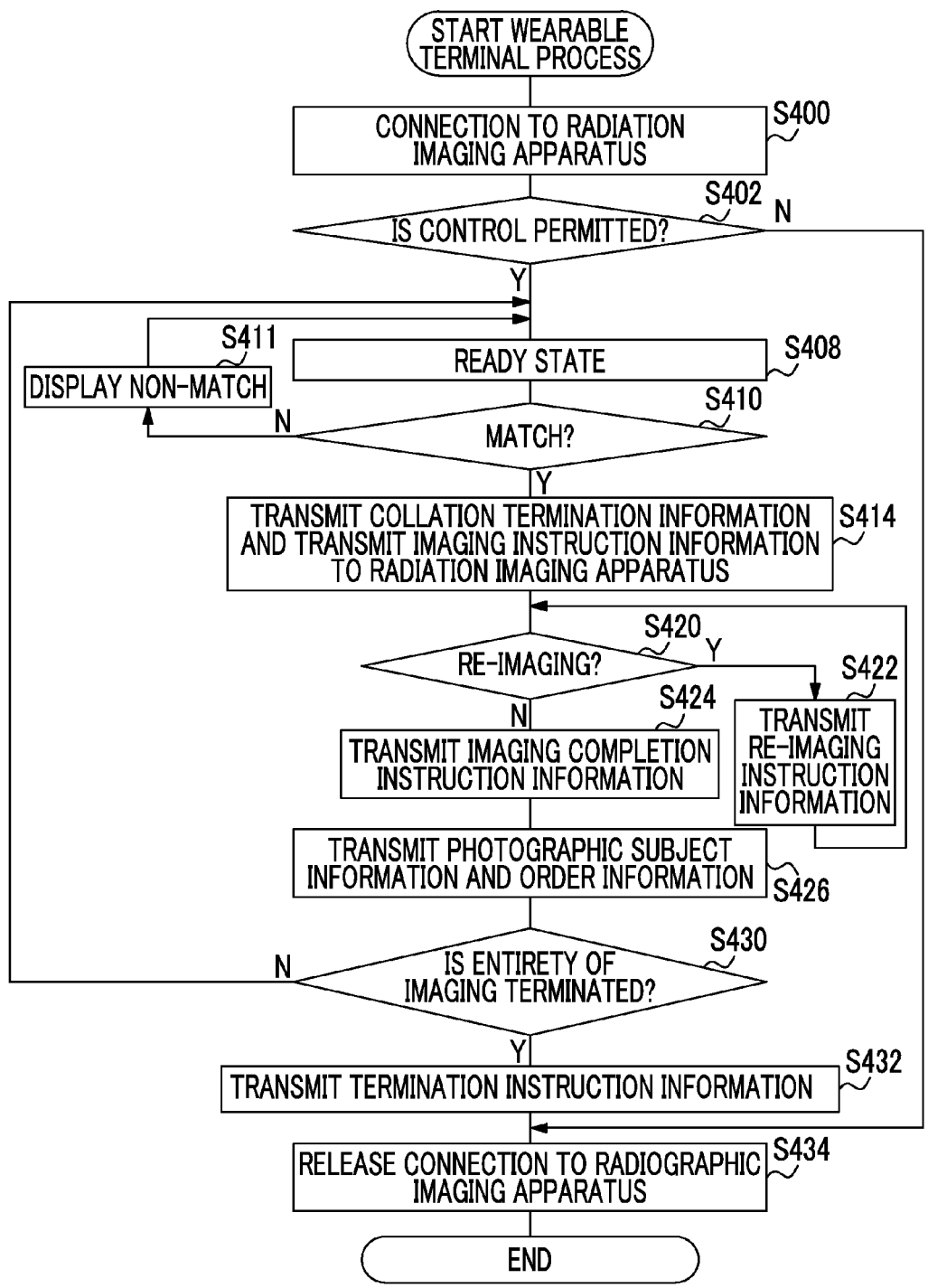

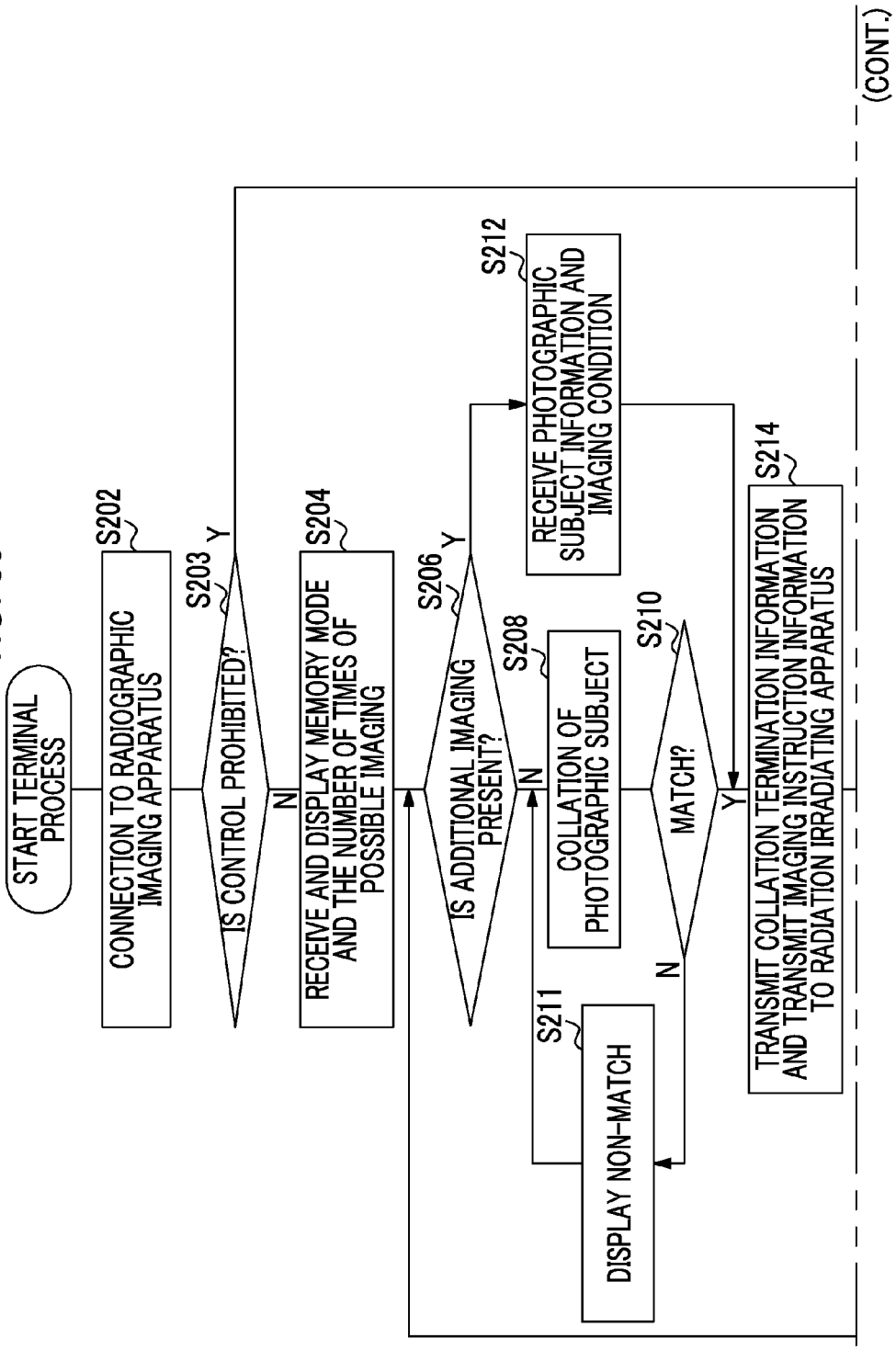

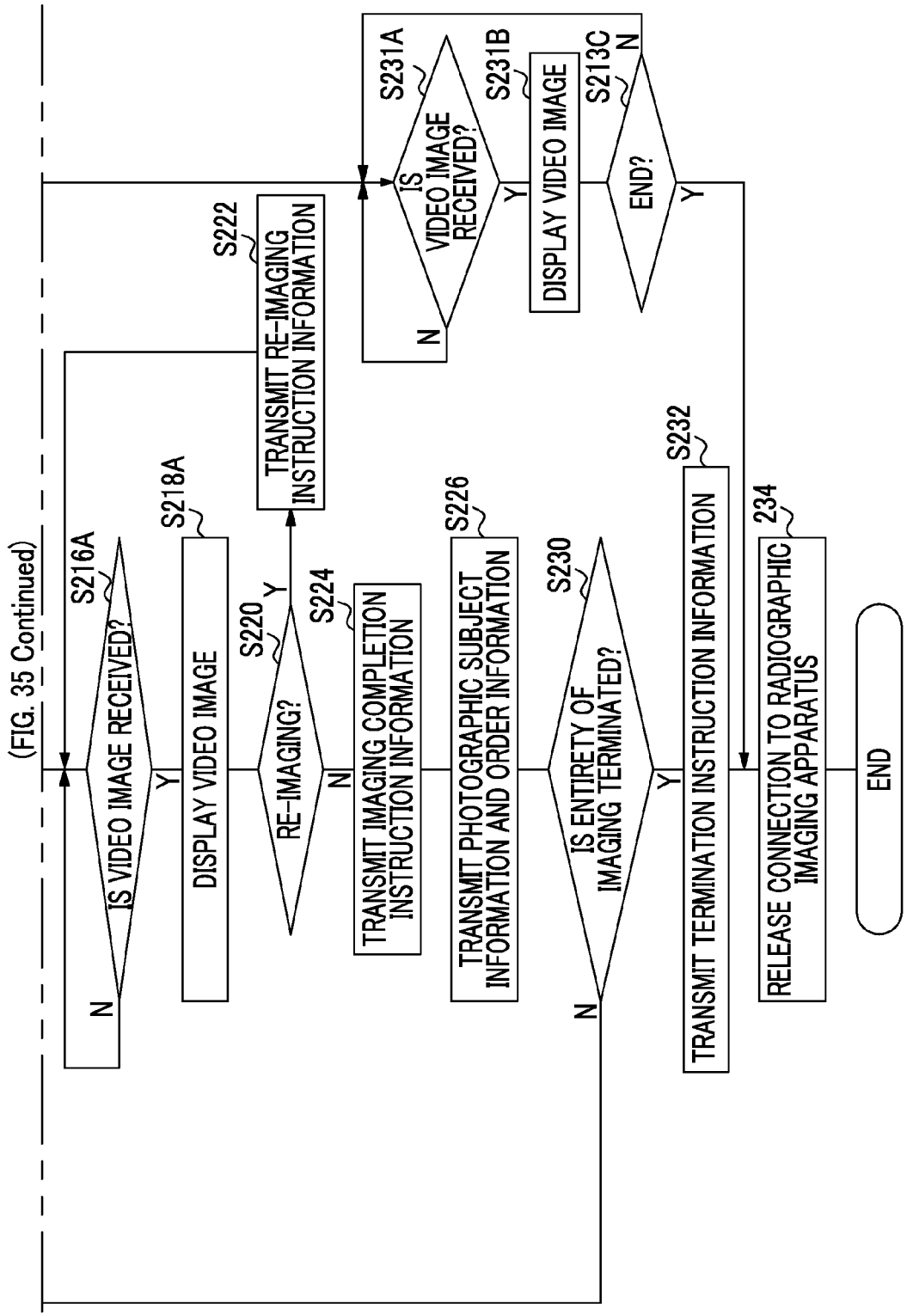

RADIOGRAPHIC IMAGE CAPTURING APPARATUS, RADIOGRAPHIC IMAGE CAPTURING SYSTEM, CONTROL METHOD OF RADIOGRAPHIC IMAGE CAPTURING APPARATUS, AND CONTROL PROGRAM OF RADIOGRAPHIC IMAGE CAPTURING APPARATUS

CROSS-REFERENCE TO RELATED APPLICATIONS

The present application claims priority under 35 U.S.C. § 119 to Japanese Patent Application No. 2015-024698, filed on Feb. 10, 2015 and Japanese Patent Application No. 2015-209215, filed on Oct. 23, 2015. Each of the above application(s) is hereby expressly incorporated by reference, in its entirety, into the present application.

BACKGROUND OF THE INVENTION

1. Field of the Invention

The present invention relates to a radiographic image capturing apparatus, a radiographic image capturing system, a control method of the radiographic image capturing apparatus, and a non-transitory computer readable recording medium recorded with a control program of the radiographic image capturing apparatus.

2. Description of the Related Art

In the related art, as a radiographic image capturing apparatus that images a photographic subject, a radiographic image capturing apparatus that performs imaging for medical diagnosis is known. The radiographic image capturing apparatus is configured so that radiation is emitted from an irradiator and a radiation detector detects the radiation passed through a photographic subject to image a radiographic image.

As a control apparatus that controls the radiographic image capturing apparatus, plural control apparatuses having different image processing functions may be used. For example, JP2013-111402A discloses a medical image broadcast system in which a console and a portable device are used as a control apparatus. Further, JP2013-141484A discloses a radiographic image capturing system in which a console and a portable terminal are used as a control apparatus.

Further, by limiting an image processing function as necessary, even a single control apparatus may be used as a control apparatus having plural image processing functions. For example, JP2012-45179A discloses a technique in which a console that limits a display function according to an imaging location where a radiographic image capturing apparatus is disposed is used as a radiographic image capturing control apparatus.

SUMMARY OF THE INVENTION

In a radiographic image capturing apparatus, there is a case where an imaging mode depending on each image processing function should be selected corresponding to plural control apparatuses having different image processing functions or a control apparatus having plural image processing functions. Thus, a user may feel inconvenience in use.

An object of the invention is to provide a technique capable of enhancing usability of a radiographic image capturing apparatus for a user.

In order to solve the problem, according to an aspect of the invention, there is provided a radiographic image capturing apparatus including: a communication unit that selectively performs communication with any one of a plurality of control apparatuses that has different image processing capacities with respect to a radiographic image and respectively performs a control relating to capturing of the radiographic image; and a selection unit that selects any one of a plurality of imaging modes predetermined with respect to the capturing of the radiographic image according to the image processing capacity of the control apparatus that performs communication with the communication unit in a case of capturing the radiographic image.

Further, in the radiographic image capturing apparatus according to this aspect of the invention, the plurality of imaging modes may include a plurality of imaging modes that varies according to the image processing capacities, and the selection unit may exclusively select any one of the plurality of imaging modes for each of the control apparatuses, according to the image processing capacities of the plurality of control apparatuses.

Further, in the radiographic image capturing apparatus according to this aspect of the invention, the plurality of control apparatuses may include a control apparatus having an image processing capacity, among the plurality of control apparatuses, lower than those of the other control apparatuses, the plurality of imaging modes may include a memory mode which is an imaging mode in which image data of a plurality of radiographic images obtained by imaging is stored in a storage unit integrated with the radiographic image capturing apparatus, and the selection unit may select the memory mode in a case where the communication unit performs communication with the control apparatus having an image processing capacity, among the plurality of control apparatuses, lower than those of the other control apparatuses.

Further, in the radiographic image capturing apparatus according to this aspect of the invention, the storage unit may be detachably and attachably mounted to the radiographic image capturing apparatus.

Further, in the radiographic image capturing apparatus according to this aspect of the invention, a control apparatus having an image processing capacity, among the plurality of control apparatuses, higher than those of the other control apparatuses may have a predetermined image processing function of generating a radiographic image for image reading, and a control apparatus having an image processing capacity lower than those of the other control apparatuses may not have the predetermined image processing function.

Further, in the radiographic image capturing apparatus according to this aspect of the invention, a control apparatus having an image processing capacity, among the plurality of control apparatuses, higher than those of the other control apparatuses may include a display unit capable of displaying a radiographic image for image reading, and a control apparatus having an image processing capacity lower than those of the other control apparatuses may include a display unit incapable of displaying the radiographic image for image reading.

Further, in the radiographic image capturing apparatus according to this aspect of the invention, the image data of the plurality of radiographic images may be image data of radiographic images in a plurality of units, in which image data of radiographic images obtained by an imaging group collected based on a predetermined reference may be one unit.

Further, in the radiographic image capturing apparatus according to this aspect of the invention, each of the plurality of control apparatuses may include a display unit having a display capacity depending on the image processing capacity, and the selection unit may select any one of the plurality of predetermined imaging modes according to the display capacity of the display unit.

Further, in the radiographic image capturing apparatus according to this aspect of the invention, the display capacity may include the size of a display region of the display unit, the plurality of imaging modes may include a memory mode which is an imaging mode in which image data of a plurality of radiographic images obtained by imaging is stored in a storage unit integrated with the radiographic image capturing apparatus, and the selection unit may select the memory mode in a case where the communication unit performs communication with the control apparatus having the display unit in which the size of the display region is smaller than a predetermined size.

Further, in the radiographic image capturing apparatus according to this aspect of the invention, the selection unit may further select any one of the plurality of imaging modes predetermined with respect to the capturing of the radiographic image, according to a communication capacity through which the communication unit performs communication with the control apparatus.

Further, in the radiographic image capturing apparatus according to this aspect of the invention, the plurality of imaging modes may include a video mode which is an imaging mode in which a video image is captured, and the radiographic image capturing apparatus may further include a permission unit that permits, in a case where the selection unit selects the video mode, a wearable device to execute at least a part of the control relating to the capturing of the radiographic image, performed by the control apparatus that performs communication with the communication unit.

Further, in the radiographic image capturing apparatus according to this aspect of the invention, the plurality of control apparatuses may include a control apparatus having an image processing capacity, among the plurality of control apparatuses, higher than those of the other control apparatuses, the plurality of imaging modes may include a normal mode which is an imaging mode in which image data of a plurality of radiographic images obtained by imaging is sequentially transmitted, and the selection unit may select the normal mode in a case where the communication unit performs communication with the control apparatus having an image processing capacity, among the plurality of control apparatuses, higher than those of the other control apparatuses.

Further, in the radiographic image capturing apparatus according to this aspect of the invention, the plurality of imaging modes may include a normal mode in which image data of a plurality of radiographic images obtained by imaging is sequentially transmitted, and a memory mode in which the image data of the plurality of radiographic images is stored in a storage unit integrated with the radiographic image capturing apparatus, and the selection unit may select the memory mode in a case where the communication unit performs communication with a control apparatus having an image processing capacity, among the plurality of control apparatuses, lower than those of the other control apparatuses.

Further, the radiographic image capturing apparatus according to this aspect of the invention may further include: a reception unit that receives a setting of the imaging mode, and the selection unit may select any one of the plurality of predetermined imaging modes based on the setting received by the reception unit.

According to another aspect of the invention, there is provided a radiographic image capturing apparatus including: a communication unit that selectively performs communication with any one of a plurality of control apparatuses that respectively performs a control relating to capturing of a radiographic image; an evaluation unit that evaluates at least one selected from a group including an image processing capacity with respect to the radiographic image, of the control apparatus that performs communication with the communication unit and a communication capacity through which the communication unit performs communication with the control apparatus, in a case of capturing the radiographic image; and a selection unit that selects any one of a plurality of imaging modes predetermined with respect to the capturing of the radiographic image based on an evaluation result of the evaluation unit.

Further, in the radiographic image capturing apparatus according to this aspect of the invention, the plurality of imaging modes may include a video mode which is an imaging mode in which a video image is captured, and the radiographic image capturing apparatus may further include: a permission unit that permits, in a case where the selection unit selects the video mode, a wearable device to execute at least a part of the control relating to the capturing of the radiographic image, performed by the control apparatus that performs communication with the communication unit.

Further, in the radiographic image capturing apparatus according to this aspect of the invention, in a case where the permission unit gives permission to the wearable device, the communication unit may transmit the radiographic image to the control apparatus that communicates with the communication unit, among the control apparatus that communicates with the communication unit and the wearable device.

According to still another aspect of the invention, there is provided a radiographic image capturing apparatus including: a communication unit that performs communication with a control apparatus that has a plurality of image processing functions having different image processing capacities with respect to a radiographic image, in which any one of the functions is selectively executed, and performs a control relating to capturing of the radiographic image; and a selection unit that selects any one of a plurality of imaging modes predetermined with respect to the capturing of the radiographic image according to the function executed by the control apparatus, among the plurality of functions, in a case of capturing the radiographic image.

According to still another aspect of the invention, there is provided a radiographic image capturing system including: the radiographic imaging apparatus according to the aspect of the invention; and a plurality of control apparatuses that has different image processing capacities with respect to a radiographic image obtained by imaging in the radiographic imaging apparatus and respectively performs a control relating to capturing of the radiographic image.

According to still another aspect of the invention, there is provided a radiographic image capturing system including: the radiographic imaging apparatus according to the aspect of the invention; and a control apparatus that has a first and a second image processing functions having different image processing capacities with respect to a radiographic image obtained by imaging in the radiographic imaging apparatus, in which any one of the functions is selectively executed, and performs a control relating to capturing of the radiographic image.

According to still another aspect of the invention, there is provided a control method of a radiographic image capturing apparatus, including: selectively performing communication with any one of a plurality of control apparatuses that has different image processing capacities with respect to a radiographic image and respectively performs a control relating to capturing of the radiographic image; and selecting any one of a plurality of imaging modes predetermined with respect to the capturing of the radiographic image according to the image processing capacity of the control apparatus with which the communication is performed in a case of capturing the radiographic image.

According to still another aspect of the invention, there is provided a non-transitory computer readable recording medium recorded with a control program of the radiographic image capturing apparatus, causing a computer to execute a process including: selectively performing communication with any one of a plurality of control apparatuses that has different image processing capacities with respect to a radiographic image and respectively performs a control relating to capturing of the radiographic image; and selecting any one of a plurality of imaging modes predetermined with respect to the capturing of the radiographic image according to the image processing capacity of the control apparatus with which the communication is performed in a case of capturing the radiographic image.

According to the invention, it is possible to obtain an effect of enhancing usability of a radiographic image capturing apparatus for a user.

BRIEF DESCRIPTION OF THE DRAWINGS

FIG. 8 is a flowchart illustrating an example of the flow of a terminal process executed by a terminal control unit of the portable information terminal of the first embodiment.

FIG. 15 is a flowchart illustrating an example of the flow of a terminal process executed by a terminal control unit of a portable information terminal of a second embodiment.

FIG. 16 is a flowchart illustrating an example of the flow of a memory mode process executed by an imaging control unit of a radiographic image capturing apparatus of the second embodiment.

FIG. 18 is a diagram illustrating a concept of the memory mode process in the radiographic image capturing apparatus of the third embodiment.

FIG. 19 is a flowchart illustrating an example of the flow of a terminal process executed by a terminal control unit of a portable information terminal of the third embodiment.

FIG. 20 is a flowchart illustrating an example of the flow of an imaging process executed by an imaging control unit of a radiographic image capturing apparatus of a fourth embodiment.

FIG. 22 is a flowchart illustrating an example of the flow of a terminal process executed by a terminal control unit of a portable information terminal of the fourth embodiment.

FIG. 25 is a flowchart illustrating an example of the flow of a console process executed by a console control unit of the fourth embodiment.

FIG. 28 is a diagram illustrating a specific example of an evaluation value of an image processing capacity.

FIG. 29 is a diagram illustrating a correspondence relationship between a control apparatus and an applicable communication method.

FIG. 31 is a block diagram illustrating an example of a schematic configuration of a radiographic image capturing apparatus, a portable information terminal, and a console of the sixth embodiment.

FIG. 32 is a flowchart illustrating an example of the flow of an imaging process executed by an imaging control unit of the radiographic image capturing apparatus of the sixth embodiment.

FIG. 33 is a flowchart illustrating an example of the flow of a video mode process executed by the imaging control unit of the radiographic image capturing apparatus of the sixth embodiment.

FIG. 34 is a flowchart illustrating an example of the flow of a wearable terminal process executed by a wearable control unit of a wearable terminal of the sixth embodiment.

FIG. 35 is a flowchart illustrating an example of the flow of a terminal process executed by a terminal control unit of a portable information terminal of the sixth embodiment.

DESCRIPTION OF THE PREFERRED EMBODIMENTS

Figure 1:
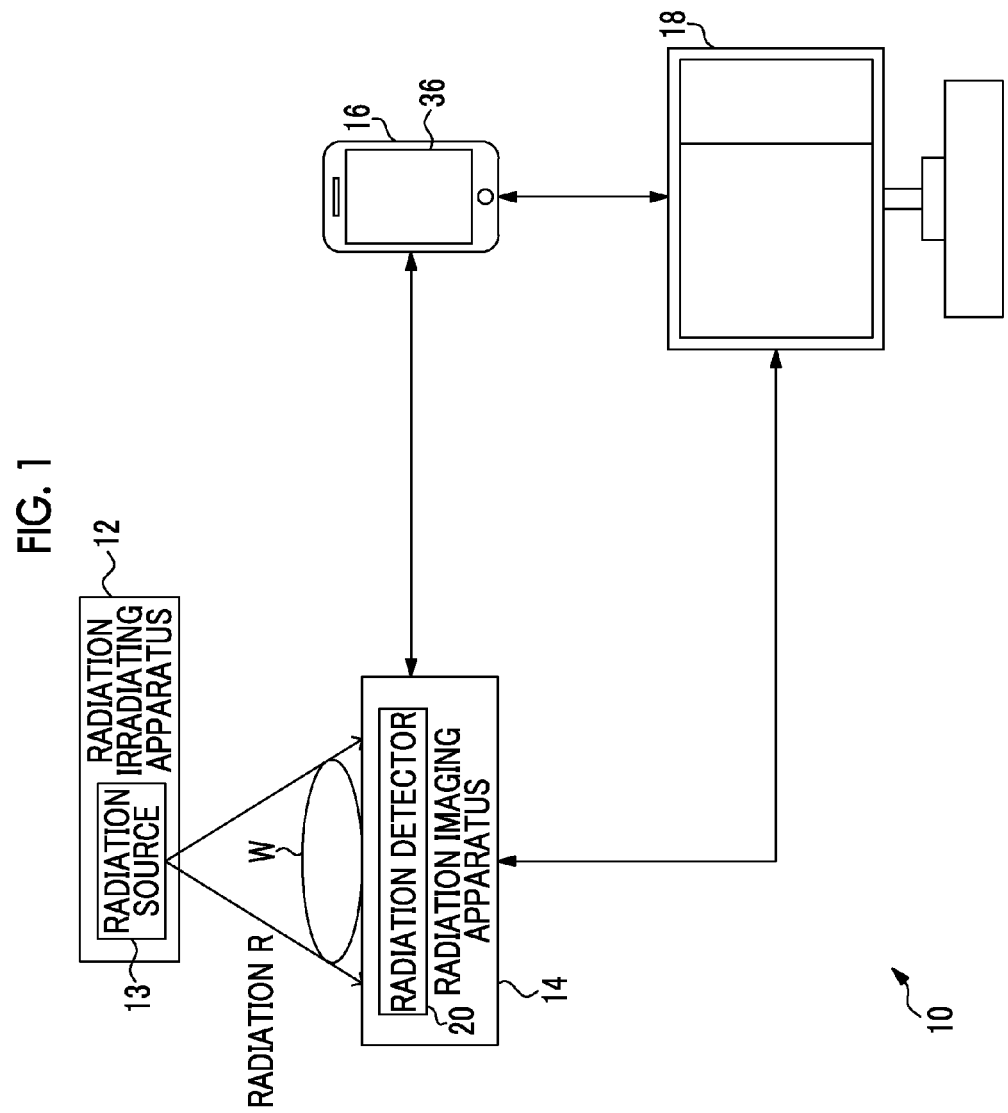
FIG. 1 is a schematic configuration diagram illustrating an example of a radiographic image capturing system of an embodiment.

Hereinafter, examples of embodiments according to the invention will be described with reference to the accompanying drawings. In the figures, the same reference numerals are given to components having the same functions, and repetitive description thereof will not be made.

First Embodiment

First, a schematic configuration of a radiographic image capturing system of a first embodiment will be described. FIG. 1 is a schematic configuration diagram illustrating an example of a radiographic image capturing system of this embodiment.

A radiographic image capturing system 10 includes an irradiator 12, a radiographic image capturing apparatus 14, a portable information terminal 16, and a console 18.

The irradiator 12 includes a radiation source 13. The irradiator 12 has a function of irradiating a photographic subject W with radiation R (for example, X-ray) from the radiation source 13. As a specific example of the irradiator 12, a mobile car may be used, for example. A method for instructing the irradiator 12 to execute the irradiation with the radiation R is not particularly limited, but in this embodiment, an irradiation execution instruction is performed from the portable information terminal 16 or the console 18.

The radiographic image capturing apparatus 14 includes a radiation detector 20 that detects radiation R that is emitted from the irradiator 12 and passes through the photographic subject W. The radiographic image capturing apparatus 14 has a function of capturing a radiographic image of the photographic subject W using the radiation detector 20. In this embodiment, an electronic cassette is used as the radiographic image capturing apparatus 14.

The portable information terminal 16 of this embodiment may be driven by a built-in battery, specifically, a tablet terminal, a smart phone which is a so-called a personal digital assistant (PDA), or the like may be used. The portable information terminal 16 has a function of controlling the capturing of the radiographic image using the radiographic image capturing apparatus 14 based on order information input through an external system such as a radiology information system (RIS) or the console 18. Thus, the portable information terminal 16 receives the order information from the external system or the console 18. The order information in this embodiment corresponds to one example of an imaging group collected on the basis of a predetermined standard of the invention. Further, image data of a radiographic image obtained by imaging corresponding to one piece of order information corresponds to one unit.

The console 18 has a function of controlling the entirety of the radiographic image capturing system 10 or a function of controlling the capturing of the radiographic image using the radiographic image capturing apparatus 14, based on the order information input through the external system such as a radiology information system (RIS), for example. Thus, the console 18 receives the order information from the external system.

In the radiographic image capturing system 10 of this embodiment, in a case where the capturing of the radiographic image is performed at a predetermined imaging location such as a hospital ward, a hospital room, or an operating room, the irradiator 12, the radiographic image capturing apparatus 14, and the portable information terminal 16 are disposed at the imaging location to perform the capturing of the radiographic image. In this case, the console 18 performs the imaging in a state of being disposed at a location (for example, in a clinic or the like of the department of radiology) different from the imaging location where the irradiator 12, the radiographic image capturing apparatus 14, and the portable information terminal 16 are disposed.

In the portable information terminal 16 and the console 18 of this embodiment, image processing functions are different from each other. In the radiographic image capturing system 10 of this embodiment, in a case where a user performs image reading of a radiographic image (including a medical examination and a diagnosis), the console 18, an image reader (not shown) such as a viewer which is separately provided, or the like is used. Thus, the image processing function of the console 18 is for generating a high-quality radiographic image capable of enduring image reading of a user, and has a high image processing capacity. On the other hand, since a display capacity using a display 36 is not necessarily high in the portable information terminal 16, the portable information terminal 16 is not suitable for display of a radiographic image for image reading. Thus, the image processing function of the portable information terminal 16 has a lower image processing capacity than that of the console 18. It is sufficient if the portable information terminal 16 of this embodiment has an image processing function of displaying a preview image (which will be described later in detail) generated by the radiographic image capturing apparatus 14 on the display 36. The preview image refers to at least one of a low quality image compared with the radiographic image for image reading or an image with a small amount of data.

Further, in the portable information terminal 16 and the console 18 of this embodiment, control functions for performing an imaging control using the radiographic image capturing apparatus 14 are different from each other. The portable information terminal 16 has only a part of the function of the console 18 for controlling the capturing of the radiographic image. Each of the portable information terminal 16 and the console 18 is an example of a control apparatus of the invention. In this embodiment, the portable information terminal 16 and the console 18 are referred to as a "control apparatus" without distinction.

Figure 2:
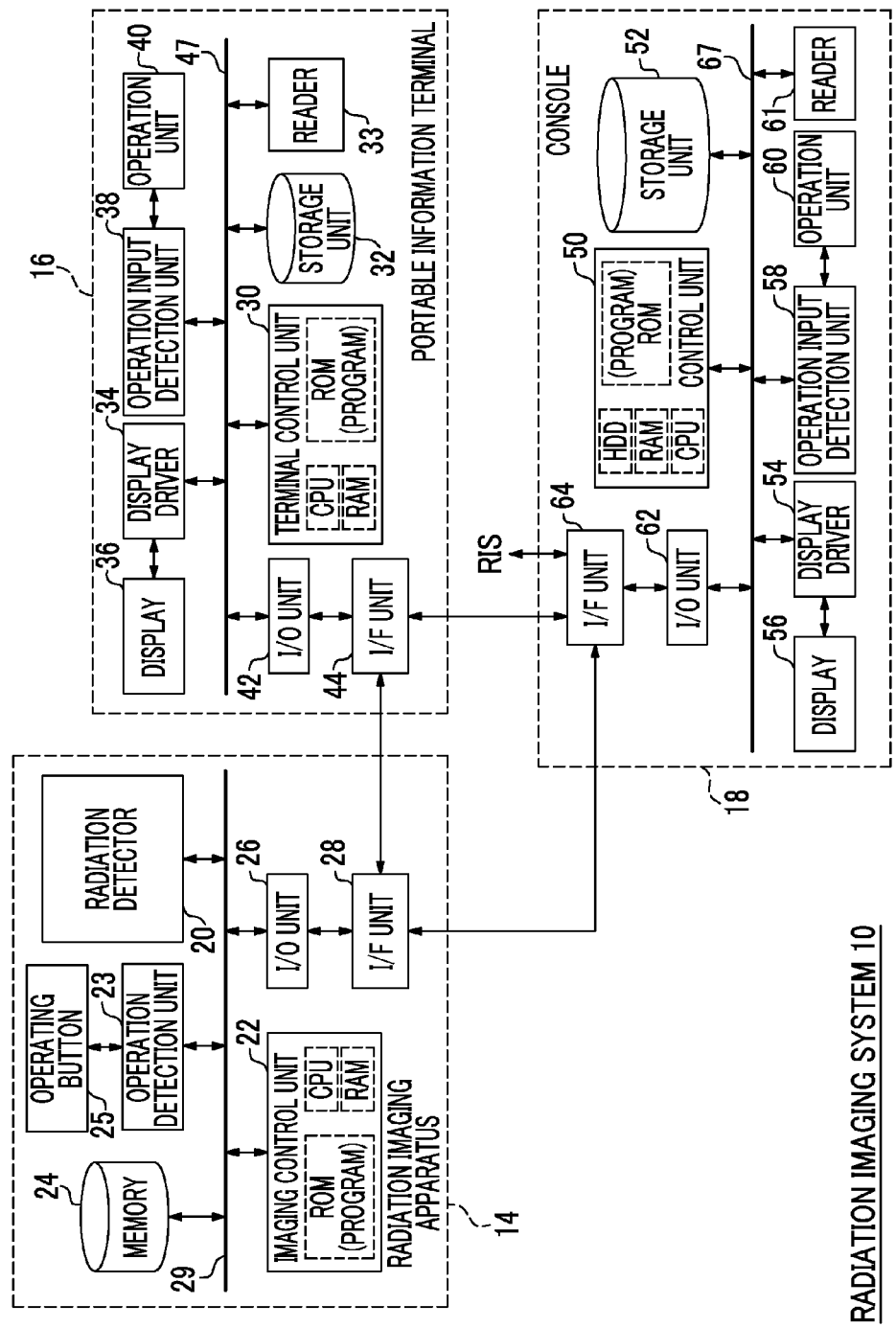
FIG. 2 is a block diagram illustrating an example of a schematic configuration of a radiographic image capturing apparatus, a portable information terminal, and a console of an embodiment.

Next, respective functions of the radiographic image capturing apparatus 14, the portable information terminal 16, and the console 18 will be described in detail. FIG. 2 is a block diagram illustrating an example of schematic configurations of the radiographic image capturing apparatus 14, the portable information terminal 16, and the console 18 of the radiographic image capturing system 10.

The radiographic image capturing apparatus 14 of this embodiment includes a radiation detector 20, an imaging control unit 22, an operation detection unit 23, a memory 24, an operating button 25, an input/output (I/O) unit 26, and an interface (I/F) unit 28. The radiation detector 20, the imaging control unit 22, the operation detection unit 23, the memory 24, and the input/output (I/O) unit 26 are connected to each other through a bus 29 such as a system bus or a control bus to be able to exchange a variety of information.

The radiographic image capturing apparatus 14 of this embodiment detects irradiation starting with radiation R using the host apparatus in an asynchronous manner with the irradiator 12 to perform the capturing of the radiographic image. In the radiographic image capturing apparatus 14, a method of detecting the irradiation starting with the radiation R using the host apparatus in an asynchronous manner with the irradiator 12 is not particularly limited. For example, the radiographic image capturing apparatus 14 may include a detection unit that detects a radiation dose of the irradiated radiation R, and may detect, when the irradiation dose detected by the detection unit exceeds a predetermined threshold value as an irradiation start, that the irradiation is started. The radiographic image capturing apparatus 14 is not limited to this embodiment, and may be any apparatus having a function of capturing the radiographic image depending on the radiation R that passes through the photographic subject W.

The radiation detector 20 includes a function of detecting the radiation R that passes through the photographic subject W under the control of the imaging control unit 22. The radiation detector 20 of this embodiment is not particularly limited. For example, the radiation detector 20 may be a radiation detector of an indirect conversion type that converts radiation R into light and converts the converted light into electric charges, or may be a radiation detector of a direct conversion type that directly converts radiation R into electric charges.

The imaging control unit 22 is an example of a selection unit of the invention, and has a function of controlling an overall operation of the radiographic image capturing apparatus 14.

The imaging control unit 22 includes a central processing unit (CPU), a read only memory (ROM), and a random access memory (RAM). The ROM stores various process programs including an imaging process program (which will be described later) executed by the CPU, or the like. The RAM has a function of temporarily storing a variety of data.

The operating button 25 is connected to the operation detection unit 23, and is provided at a position where there is no obstacle in a case where a radiographic image is captured, in a housing (not shown) of the radiographic image capturing apparatus 14.

The memory 24 is an example of a storage unit integrated with the host apparatus of the invention. The memory 24 stores image data of a radiographic image obtained by imaging, or the like. As a specific example of the memory 24, a solid state drive (SSD) or the like may be used. The memory 24 may be integrated with the radiographic image capturing apparatus 14 in a case of performing the capturing of the radiographic image, and for example, may be a memory capable of being detachably and attachably mounted from the radiographic image capturing apparatus 14, such as a universal serial bus (USB) memory or a secure digital (SD) memory card (registered trademark).

The I/F unit 28 is connected to the I/O unit 26, and has a function of performing communication of a variety of information with the portable information terminal 16 or the console 18 through wireless communication or the like using a radio wave or light. The radiographic image capturing apparatus 14 of this embodiment uses short-range wireless communication in a case of performing communication with the portable information terminal 16, and uses wireless local area network (LAN) communication in a case of performing communication with the console 18. Specifically, the radiographic image capturing apparatus 14 uses Bluetooth (registered trademark) in a case of performing communication with the portable information terminal 16, and uses Wireless-Fidelity (Wi-Fi, registered trademark) in a case of performing communication with the console 18.

The I/F unit 28 and the imaging control unit 22 form an example of a communication unit of the invention.

The portable information terminal 16 of this embodiment includes a terminal control unit 30, a storage unit 32, a reader 33, a display driver 34, a display 36, an operation input detection unit 38, an operation unit 40, an I/O unit 42, and an I/F unit 44. The terminal control unit 30, the storage unit 32, the reader 33, the display driver 34, the operation input detection unit 38, and the I/O unit 42 are connected to each other through a bus 47 such as a system bus or a control bus to be able to exchange a variety of information.

The terminal control unit 30 has a function of controlling an overall operation of the portable information terminal 16. Further, the terminal control unit 30 has a function of acquiring order information through the I/F unit 44 through the console 18 or an external system.

The terminal control unit 30 includes a CPU, a ROM, and a RAM. The ROM stores in advance various process programs including a terminal program (which will be described later) executed by the CPU, or the like. The RAM has a function of temporarily storing a variety of data.

The reader 33 of this embodiment has a function of reading a character, an image, or the like. Specifically, the reader 33 has a camera function, and functions as a barcode reader.

The display 36 of this embodiment is an example of a display unit of the invention, and has a function of displaying a variety of information relating to imaging or a preview image of a radiographic image obtained by imaging. The display driver 34 has a function of controlling display of the variety of information on the display 36.

The operation unit 40 is used when a user inputs an instruction relating to capturing of a radiographic image, a variety of information, or the like. The operation unit 40 of this embodiment includes a touch panel, a touch pen, plural keys, a mouse, or the like. In this embodiment, the display 36 and the operation unit 40 are integrated to form a touch panel display. The operation input detection unit 38 has a function of detecting an operation state with respect to the operation unit 40.

The I/O unit 42 and the I/F unit 44 have a function for performing communication of a variety of information with the radiographic image capturing apparatus 14 or the console 18. The portable information terminal 16 of this embodiment uses short-range wireless communication in a case of performing communication with the radiographic image capturing apparatus 14, and uses wireless LAN communication in a case of performing communication with the console 18 through wireless communication using radio waves or light, or the like. Specifically, the portable information terminal 16 of this embodiment uses Bluetooth (registered trademark) in a case of performing communication with the radiographic image capturing apparatus 14, and uses Wi-Fi (registered trademark) in a case of performing communication with the console 18.

The storage unit 32 stores the above-mentioned order information or the like. As a specific example of the storage unit 32, an SSD or the like may be used. The storage unit 32 may be a memory capable of being detachably and attachably mounted to the portable information terminal 16, such as a USB memory or an SD memory card.

The console 18 of this embodiment functions as a server computer. The console 18 includes a control unit 50, a storage unit 52, a display driver 54, a display 56, an operation input detection unit 58, an operation unit 60, a reader 61, an I/O unit 62, and an I/F unit 64. The control unit 50, the storage unit 52, the display driver 54, the operation input detection unit 58, the reader 61, and the I/O unit 62 are connected to each other through a bus 67 such as a system bus or a control bus to be able to exchange a variety of information.

The control unit 50 has a function of controlling an overall operation of the console 18, and includes a CPU, a ROM, a RAM, and a hard disk drive (HDD). The ROM stores in advance various process programs or the like executed by the CPU. The RAM has a function of temporarily storing a variety of data. The HDD has a function of storing and retaining a variety of data.

The display 56 of this embodiment is an example of a display unit of the invention, and has a function of displaying a variety of information relating to imaging, a radiographic image for image reading, or the like. The display driver 54 has a function of controlling display of a variety of information on the display 56. The operation unit 60 is used when a user inputs information relating to capturing of a radiographic image, or the like. The operation unit 60 of this embodiment includes a touch panel, a touch pen, plural keys, a mouse, and the like, for example. In a case where the operation unit 60 includes the touch panel, the touch panel may be integrated with the display 56. The operation input detection unit 58 has a function of detecting an operation state with respect to the operation unit 60.

The reader 61 of the embodiment has a function of reading a character, an image or the like. Specifically, the reader 61 has a camera function, and functions as a barcode reader.

The I/O unit 62 and the I/F unit 64 have a function for performing communication of a variety of information with the radiographic image capturing apparatus 14 or the portable information terminal 16. The console 18 of this embodiment uses wireless LAN communication in a case of performing communication with the radiographic image capturing apparatus 14 and the portable information terminal 16 through wireless communication using radio waves or light, or the like. Specifically, the console 18 of this embodiment uses Wi-Fi (registered trademark) in a case of performing communication with the radiographic image capturing apparatus 14 and the portable information terminal 16.

The storage unit 52 stores image data of a radiographic image and photographic subject information in association.

As a specific example of the storage unit 52, an HDD, an SSD, or the like may be used.

Next, an operation of the radiographic image capturing system 10 of this embodiment in a case where a radiographic image is captured will be described.

Figure 3:
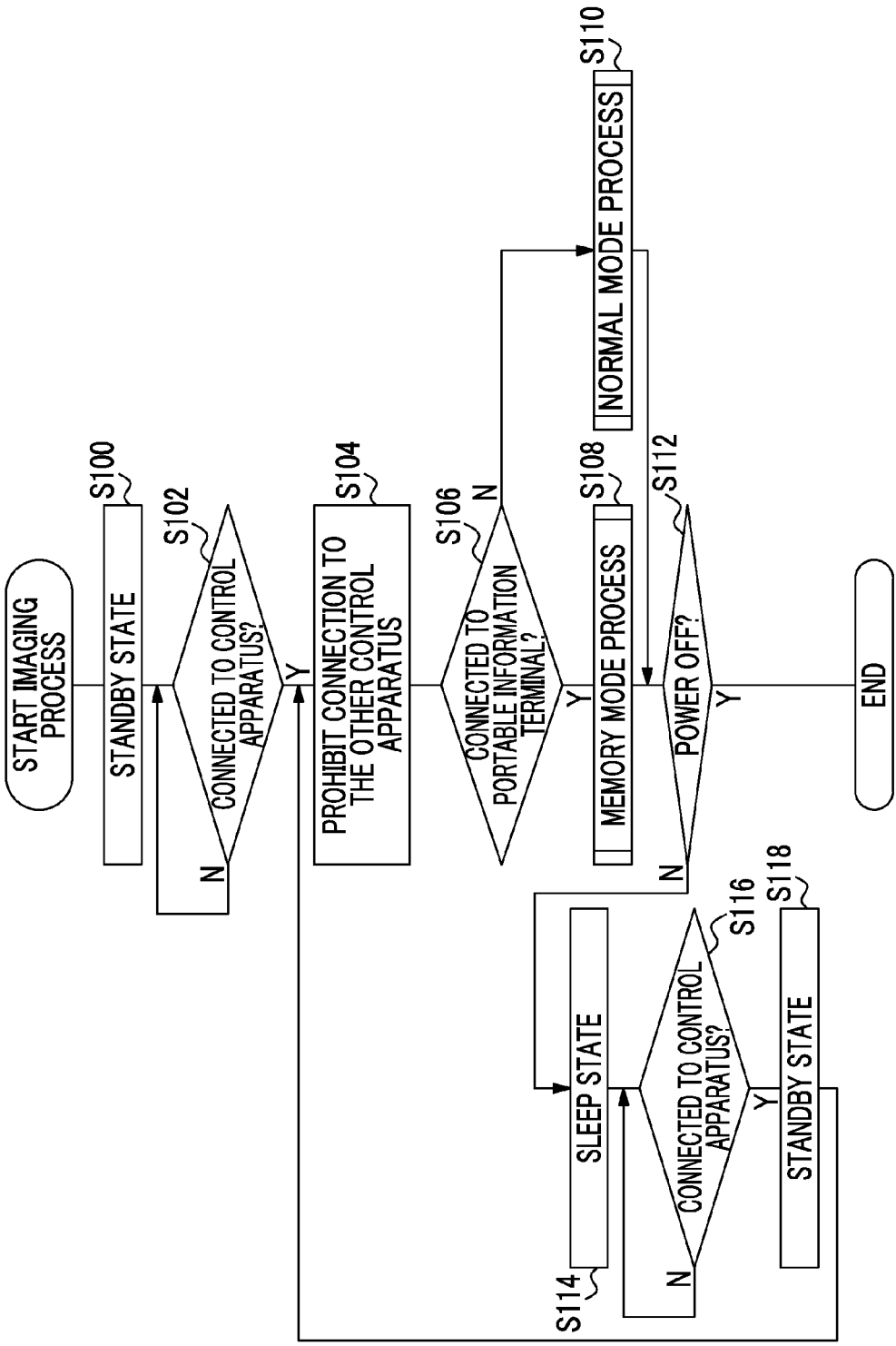
FIG. 3 is a flowchart illustrating an example of the flow of an imaging process executed by an imaging control unit of a radiographic image capturing apparatus of a first embodiment.

First, an operation of the radiographic image capturing apparatus 14 will be described. FIG. 3 shows a flowchart illustrating an example of the flow of an imaging process executed by the imaging control unit 22 of the radiographic image capturing apparatus 14 of this embodiment. In the radiographic image capturing apparatus 14 of this embodiment, the imaging control unit 22 executes an imaging process program stored in the ROM of the host apparatus to execute the imaging process.

The imaging process is executed when power is supplied using a power switch (not shown) of the radiographic image capturing apparatus 14.

In step S100 of FIG. 3, the imaging control unit 22 sets the radiation detector 20 to a standby state. Here, the "standby state" in this embodiment refers to a state where the power switch of the radiographic image capturing apparatus 14 is turned on to wait for an instruction of capturing of a radiographic image.

In the next step S102, the imaging control unit 22 determines which control apparatus of the portable information terminal 16 and the console 18 is connected. Here, the "connection" means connection through communication, which may not be direct and physical connection. Thus, in this embodiment, "connection to the radiographic image capturing apparatus 14" means that communication is performed with the radiographic image capturing apparatus 14.

In the imaging control unit 22 of the radiographic image capturing apparatus 14, in a case where communication is received from the portable information terminal 16 or the console 18, it is determined that the control apparatus is connected. In a case where the control apparatus is not connected, the standby state is continued, and in a case where the control apparatus is connected, the procedure proceeds to step S104.

In step S104, the imaging control unit 22 prohibits connection of the host apparatus and a control apparatus different from the connected control apparatus. The imaging control unit 22 prohibits the connection with the different control apparatus by prohibiting communication with the different control apparatus. For example, in a case where it is determined in step S102 that the portable information terminal 16 is connected, connection with the console 18 is prohibited. Similarly, in a case where it is determined in step S102 that the console 18 is connected, connection with the portable information terminal 16 is prohibited. As the connection with the different control apparatus is prohibited, the radiographic image capturing apparatus 14 is only connected to a single control apparatus. Thus, in the radiographic image capturing apparatus 14, it is possible to prevent non-match from occurring with respect to controls performed by the plural control apparatuses.

In the next step S106, the imaging control unit 22 determines whether or not the connected control apparatus is the portable information terminal 16.

A method of determining whether or not the connected control apparatus in the imaging control unit 22 of this embodiment is the portable information terminal 16 is not particularly limited. For example, as described above, since the portable information terminal 16 and the console 18 have different communication types, the determination may be performed by a communication type (Bluetooth (registered trademark) or Wi-Fi (registered trademark)) for connection from the control apparatus. Further, for example, identification information indicating which one of the portable information terminal 16 and the console 18 is the host apparatus may be transmitted to the radiographic image capturing apparatus 14 from the control apparatus, and the determination may be performed based on the identification information.

In the radiographic image capturing apparatus 14 of this embodiment, as an imaging mode of a radiographic image which is executable by the host apparatus, a memory mode which is an imaging mode in which image data of plural radiographic images obtained by imaging is stored in the memory 24 is provided. Since the portable information terminal 16 has a low image processing capacity compared with that of the console 18 and does not display a radiographic image for image reading, in a case where the connected control apparatus is the portable information terminal 16, the radiographic image capturing apparatus 14 selects the memory mode as the imaging mode.

Further, in the radiographic image capturing apparatus 14 of this embodiment, as the imaging mode, a normal mode which is an imaging mode in which image data of a radiographic image obtained by imaging is appropriately transmitted to the control apparatus but the image data of the plural radiographic images is not stored in the memory 24 of the radiographic image capturing apparatus 14 is provided. Since the console 18 has a high image processing capacity compared with that of the portable information terminal 16 and displays a radiographic image for image reading, in a case where the connected control apparatus is the console 18, the radiographic image capturing apparatus 14 selects the normal mode as the imaging mode.

In the normal mode, there is a case where image data of a radiographic image captured whenever capturing one radiographic image is transmitted to the control apparatus and then the next imaging is performed, but in a case where capturing of plural radiographic images is instructed by one piece of order information, it may be convenient to continuously capture plural radiographic images instructed by one piece of order information for a user.

That is, the memory mode in the radiographic image capturing apparatus 14 of this embodiment is an imaging type capable of continuously performing imaging depending on plural pieces of order information. In the case of the memory mode, the image data stored in the memory 24 is transmitted to an external apparatus such as the control apparatus on the condition that a series of continuous imaging is terminated (for example, a memory mode process is terminated, which will be described later in detail), or on the condition that transmission of the image data is instructed from the external apparatus such as the control apparatus, for example.

On the other hand, in the case of the normal mode, the image data stored in the memory 24 is transmitted to the external apparatus such as the control apparatus on the condition that capturing of one radiographic image is terminated, or on the condition that imaging depending on one piece of order information is terminated.

In the radiographic image capturing apparatus 14 of this embodiment, in a case where the connected control apparatus is the portable information terminal 16, the memory mode is selected as the imaging mode. On the other hand, in a case where the connected control apparatus is the console 18, the normal mode is selected as the imaging mode.

Thus, in a case where the determination in step S106 is affirmative, the procedure proceeds to step S108 in order to perform a process depending on the memory mode.

Figure 4:
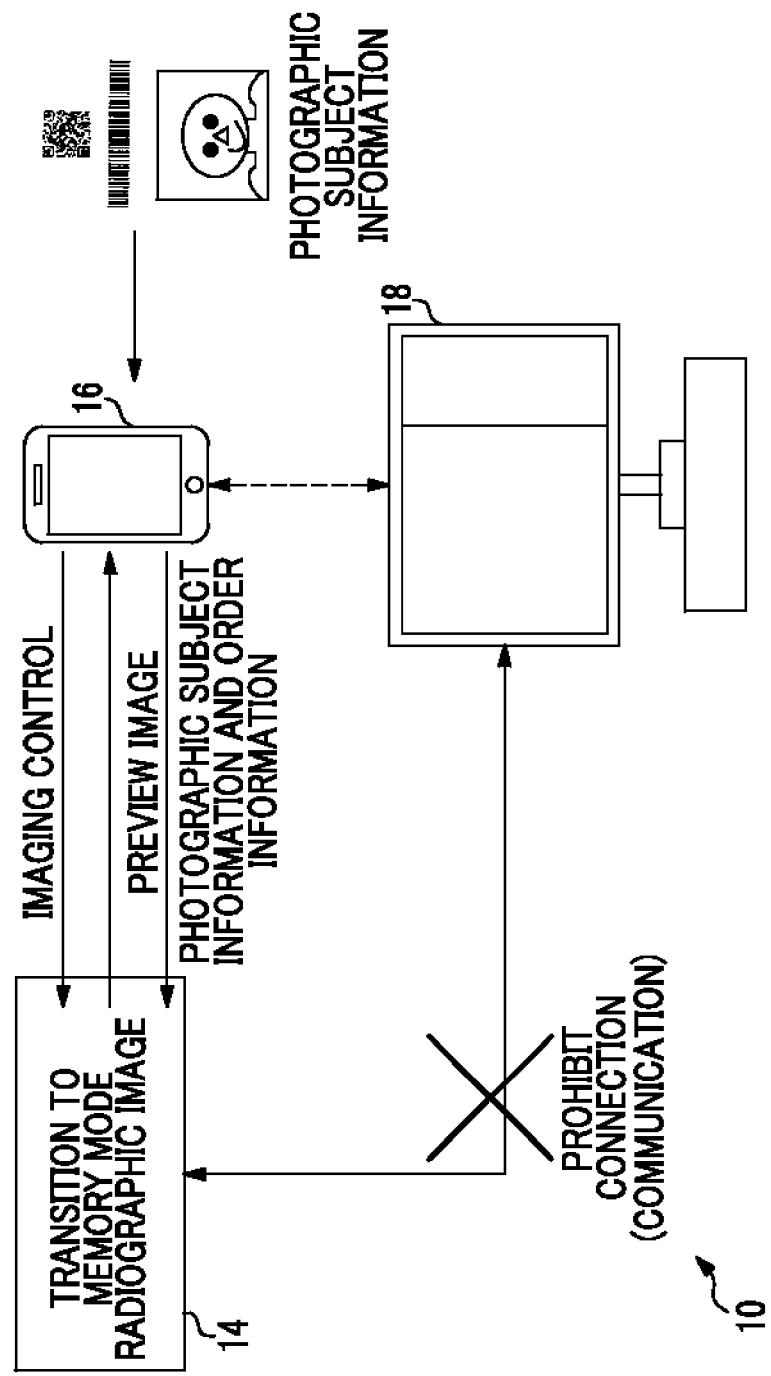
FIG. 4 is a diagram illustrating a concept of a memory mode process in the radiographic image capturing apparatus of the first embodiment.

In step S108, the imaging control unit 22 performs the memory mode process. FIG. 4 is a diagram illustrating a concept of the memory mode process in the radiographic image capturing apparatus 14 of this embodiment. Further, FIG. 5 is a flowchart illustrating an example of the flow of the memory mode process executed by the imaging control unit 22 of this embodiment.

Figure 5:
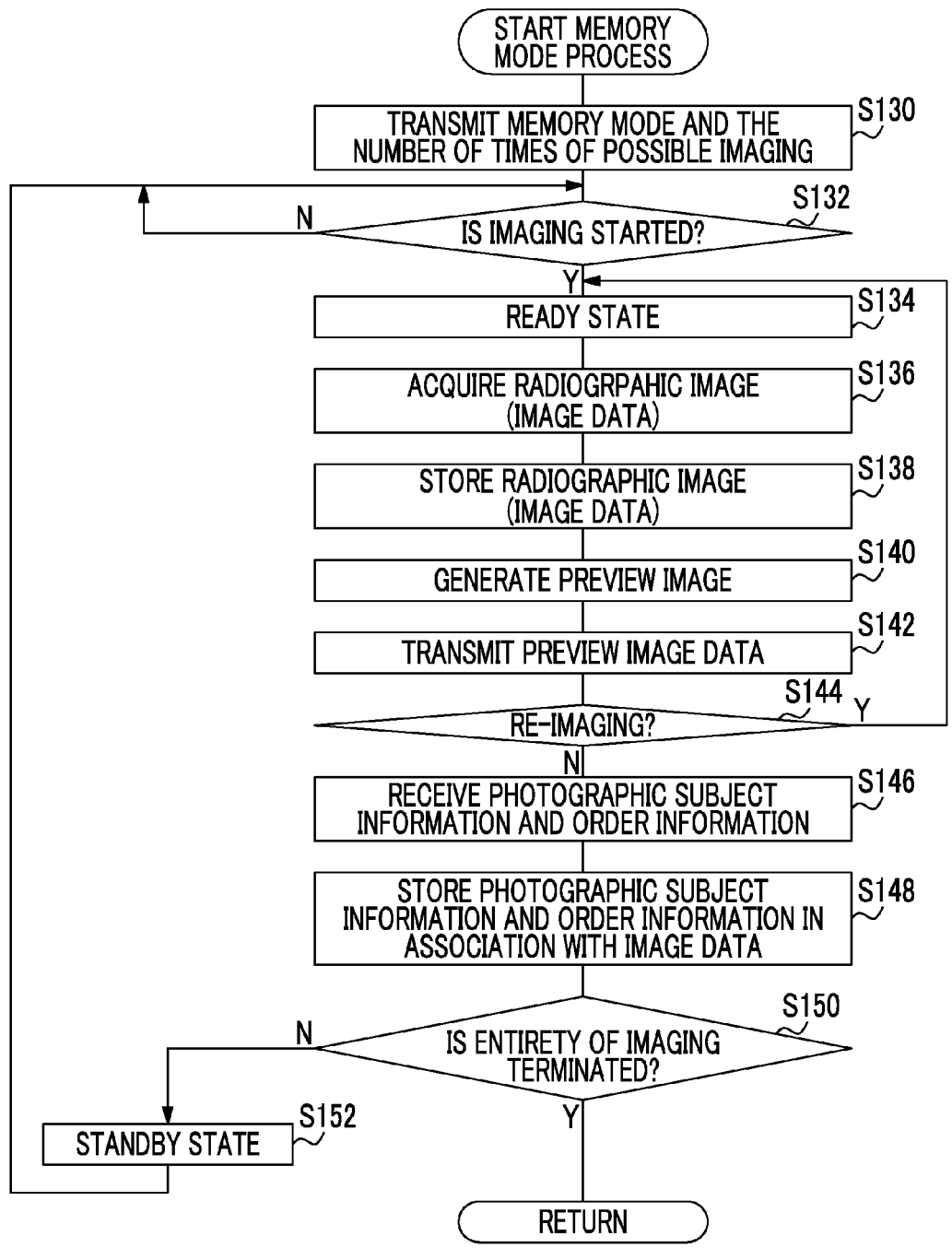
FIG. 5 is a flowchart illustrating an example of the flow of the memory mode process executed by the imaging control unit of the radiographic image capturing apparatus of the first embodiment.

As shown in FIG. 5, in step S130 of the memory mode process, the imaging control unit 22 transmits information indicating that the mode is changed to the memory mode and information indicating the number of photographable images to the portable information terminal 16. As described later, the transmitted information is displayed on the display 36 of the portable information terminal 16 (see step S204 in FIG. 8). In a case where the radiographic image capturing apparatus 14 has a display unit, the information may be displayed on the display unit of the radiographic image capturing apparatus 14.

The imaging control unit 22 determines the number of photographable images from an empty capacity of the memory 24. A determination method is not particularly limited, but for example, the number of photographable images may be determined based on the size (average size) of image data of a radiographic image with an average size and average resolution. Further, for example, in a case where order information is obtained, a correspondence relationship between the order information and the size of the image data of the radiographic image captured according to the order information may be stored in advance, and the number of photographable images may be determined based on the size of the image data corresponding to the obtained order information.

Information to be transmitted to the portable information terminal 16 is not limited thereto. For example, instead of the information indicating the number of photographable images, or together with the information indicating the number of photographable images, information indicating the empty capacity of the memory 24 may be transmitted to the portable information terminal 16.

In the next step S132, the imaging control unit 22 determines whether capturing of a radiographic image is started. Here, since the portable information terminal 16 is connected as the control device, the portable information terminal 16 instructs the capturing of the radiographic image. Specifically, in a case where collation termination information (which will be described later, see step S214 in FIG. 8) is received from the portable information terminal 16, the imaging control unit 22 determines that the capturing of the radiographic image is started.

In a case where the collation termination information is not received, a standby state is continued as it is, and in a case where the collation termination information is received, the procedure proceeds to step S134.

In step S134, the imaging control unit 22 performs a control for causing the radiation detector 20 to enter a ready state which is a state where detection of radiation R can be immediately performed. The "ready state" in this embodiment refers to a state where the radiation detector 20 can immediately perform imaging, and refers to a state where irradiation starting with the radiation R is waited for. In this way, in the ready state, for example, since the radiation detector 20 performs an operation of detecting irradiation starting with radiation R, for example, power consumption increases compared with that in the standby state.

In this embodiment, in a case where the portable information terminal 16 is connected to the radiographic image capturing apparatus 14 as the control apparatus, the portable information terminal 16 instructs the irradiator 12 to perform the capturing of the radiographic image. Thus, in a case where imaging instruction information for a radiographic image transmitted from the portable information terminal 16 is received, the irradiator 12 performs irradiation with radiation R.

Under the above-described control of the portable information terminal 16 and the imaging control unit 22, the radiation detector 20 detects the radiation R that is emitted from the irradiator 12 and passes through the photographic subject W, to thereby capture the radiographic image depending on the photographic subject W.

If the radiographic image is captured by the radiation detector 20, in the next step S136, the imaging control unit 22 acquires image data obtained by the capturing of the radiographic image from the radiation detector 20. In the next step S138, the imaging control unit 22 stores the acquired image data in the memory 24.

In the next step S140, the imaging control unit 22 generates a preview image based on the image data (raw data) stored in the memory 24. The preview image is an image used when a user determines whether or not the capturing of the radiographic image relating to the photographic subject W is appropriately performed or at least re-imaging is necessary. The imaging control unit 22 of this embodiment performs image processing for generating a preview image with respect to raw data of the radiographic image to generate the preview image. Here, the imaging control unit 22 of this embodiment uses image processing for which it does not take a relatively long time, among plural kinds of image processing performed in a case of generating a radiographic image for image reading, as the image processing for generating the preview image. As a specific example, the imaging control unit 22 performs offset correction and gain correction with respect to the raw data of the radiographic image, but does not perform defect pixel correction. A function of the image processing for performing the defective pixel correction corresponds to an example of a predetermined image processing function of generating the radiographic image for image reading of the invention.

Further, in the radiographic image capturing apparatus 14 of this embodiment, as the imaging process for generating the preview image, image processing for thinning the raw data of the radiographic image is also performed. Thus, the image data of the preview image has a data volume smaller than that of the raw data. The degree of the thinning may be determined in advance according to a resolution of the display 36 of the portable information terminal 16, a transmission speed of the image data, an image quality of a preview image desired by a user, and the like, or may be instructed by the user from the portable information terminal 16.

Accordingly, the preview image displayed on the display 36 of the portable information terminal 16 of this embodiment has image quality lower than that of the radiographic image for image reading displayed on the display 56 of the console 18.

In the next step S142, the imaging control unit 22 transmits image data of the generated preview image to the portable information terminal 16. In the portable information terminal 16, the preview image is displayed on the display 36 based on the received image data (see step S218 in FIG. 8). The user refers to and confirms the preview image displayed on the display 36 of the portable information terminal 16, and gives an instruction about the necessity of re-imaging to the radiographic image capturing apparatus 14 using the operation unit 40 of the portable information terminal 16. Specifically, in a case where a message indicating that the re-imaging is necessary is input to the operation unit 40 by the user, the portable information terminal 16 transmits re-imaging instruction information to the radiographic image capturing apparatus 14 (see step S222 in FIG. 8). Further, in a case where a message indicating that the re-imaging is not necessary is input to the operation unit 40 by the user, the portable information terminal 16 transmits imaging completion instruction information to the radiographic image capturing apparatus 14 (see step S224 in FIG. 8).

In the next step S144, the imaging control unit 22 determines whether or not the re-imaging instruction information is received from the portable information terminal 16 to determine whether to perform the re-imaging. Here, in a case where the determination is affirmative, the procedure returns to step S134 to repeat capturing of a radiographic image of the photographic subject W again. In performing the re-imaging, after the user confirms the preview image, it is preferable that information indicating that the re-imaging is performed is stored in the memory 24 in association with the image data of the radiographic image for which the re-imaging is instructed.

On the other hand, in a case where the determination in step S144 is negative, the imaging control unit 22 considers that the imaging completion instruction information is received from the portable information terminal 16, and the procedure proceeds to step S146.

In a case where capturing of plural radiographic images is instructed by one piece of order information, for example, in a case where plural radiographic images are captured with respect to the same photographic subject W, the processes of steps S134 to 144 are repeatedly performed.

If the capturing of the radiographic images is completed, the portable information terminal 16 transmits at least one of the photographic subject information or the order information to the radiographic image capturing apparatus 14 (see step S226 in FIG. 8).

Thus, in step S146, the imaging control unit 22 receives at least one of the photographic subject information or the order information from the portable information terminal 16. Further, in the next step S148, the imaging control unit 22 stores the received at least one of the photographic subject information or the order information in the memory 24 in association with the image data of the radiographic image stored by the process of step S138.

In the next step S150, the imaging control unit 22 determines whether or not the entirety of imaging is terminated. In a case where it is determined that the entirety of imaging is not terminated, the procedure proceeds to step S152, and the imaging control unit 22 performs a control for bringing the radiation detector 20 into a standby state. Here, although described in detail later, "the entirety of imaging" refers to the entirety of imaging included in an imaging list in the portable information terminal 16.

If the entirety of imaging is terminated, the portable information terminal 16 transmits termination instruction information (see step S232 in FIG. 8). Thus, in a case where the termination instruction information is not received in step S150, the imaging control unit 22 of the radiographic image capturing apparatus 14 determines that the entirety of imaging is not terminated. On the other hand, in a case where the termination instruction information is received, it is determined that the entirety of imaging is completed.

In step S150, in a case where it is determined that the entirety of imaging is terminated, the imaging control unit 22 terminates the memory mode process.

According to the above-described memory mode process, as shown in FIG. 4, for example, the image data of the preview image generated from the radiographic image obtained from the imaging is transmitted to the portable information terminal 16 from the radiographic image capturing apparatus 14. Further, at least one of the photographic subject information or the order information is transmitted to the radiographic image capturing apparatus 14 from the portable information terminal 16. The radiographic image capturing apparatus 14 stores at least one of the received photographic subject information or order information in the memory 24 in association with the image data of the radiographic image.

In this way, if the memory mode process is terminated, the procedure proceeds to step S112 of the imaging process (see FIG. 3). If the memory mode process is terminated, the connection (communication) of the radiographic image capturing apparatus 14 and the portable information terminal 16 is released by the portable information terminal 16 (see step S234 in FIG. 8).

On the other hand, in a case where the determination in step S106 of the imaging process is negative, it is considered that the console 18 is connected, and the procedure proceeds to step S110.

Figure 6:
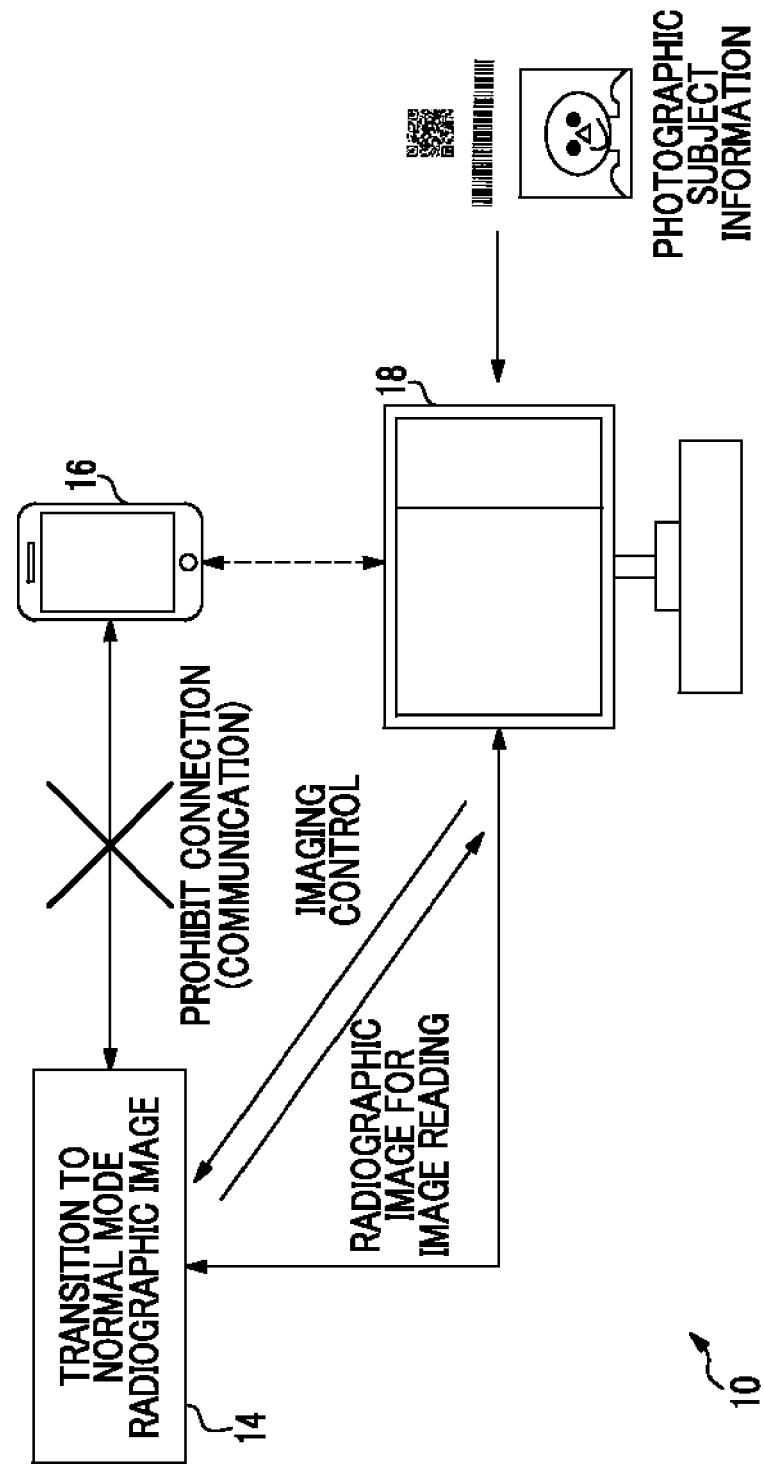
FIG. 6 is a diagram illustrating a concept of a normal mode process in the radiographic image capturing apparatus of the first embodiment.

In step S110, the imaging control unit 22 performs a normal mode process. FIG. 6 is a diagram illustrating a concept of the normal mode process in the radiographic image capturing apparatus 14 of this embodiment. Further, FIG. 7 is a flowchart illustrating an example of the flow of the normal mode process executed by the imaging control unit 22 of this embodiment.

Figure 7:
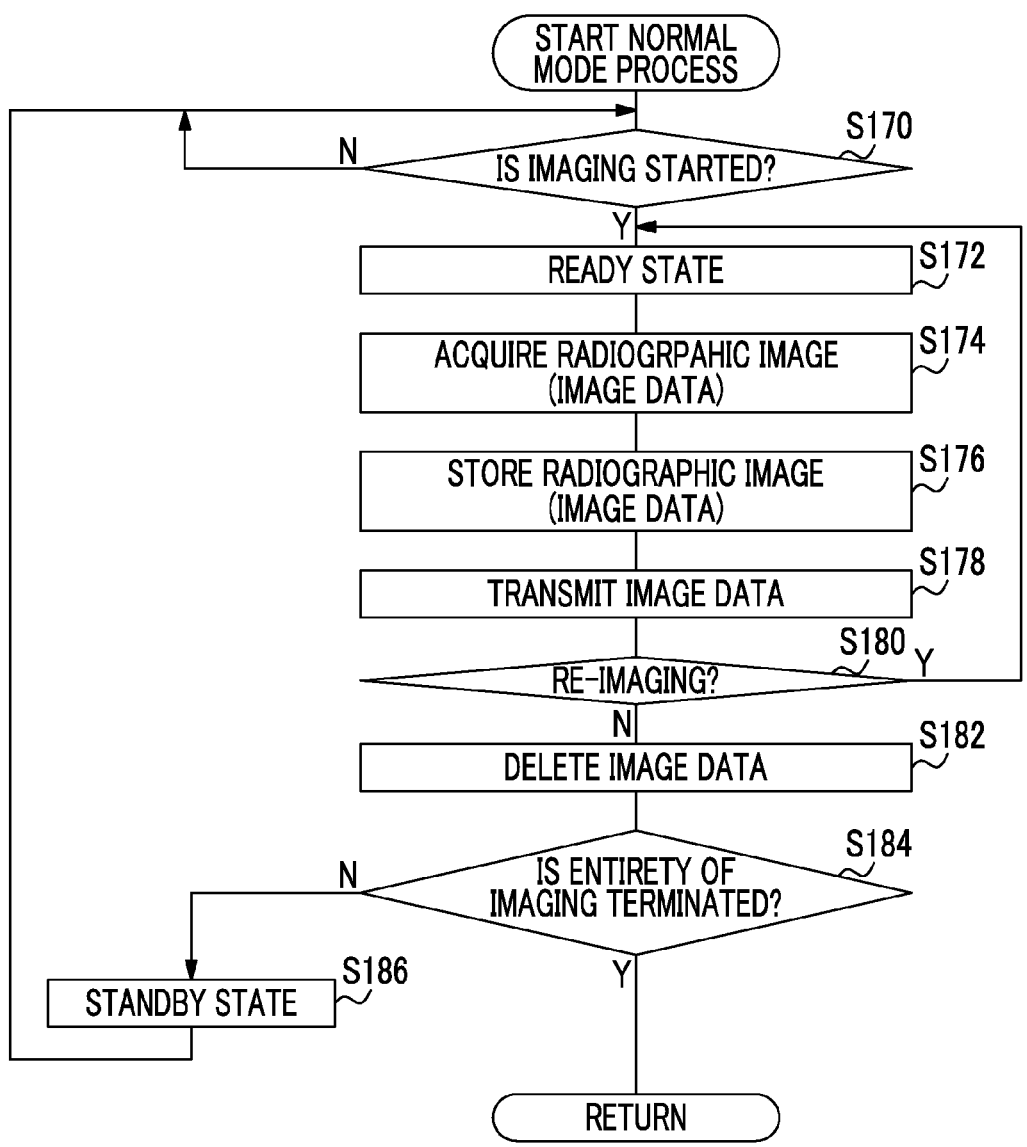
FIG. 7 is a flowchart illustrating an example of the flow of the normal mode process executed by the imaging control unit of the radiographic image capturing apparatus of the first embodiment.

As shown in FIG. 7, in step S170 of the normal mode process, the imaging control unit 22 determines whether capturing of a radiographic image is started. Here, since the console 18 is connected as the control apparatus, the condole 18 instructs the capturing of the radiographic image. Specifically, in a case where collation termination information (see step S308 in FIG. 13) (which will be described later) is received from the console 18, the imaging control unit 22 determines that the capturing of the radiographic image is started.

In a case where the collation termination information is not received, the standby state is continued as it is, and in a case where the collation termination information is received, the procedure proceeds to step S172.

In steps S172 to S176, the same processes as the processes in steps S134 to 138 of the memory mode process (see FIG. 5) are performed, so that a radiographic image depending on the photographic subject W is captured, and image data of the radiographic image is stored in the memory 24.

In the next step S178, the imaging control unit 22 transmits the image data of the radiographic image to the console 18. The image data of the radiographic image to be transmitted herein may be raw data, or may be image data after predetermined image processing. In this embodiment, as a specific example, the imaging control unit 22 transmits image data of a radiographic image for image reading obtained by performing offset correction, gain correction, and defect correction with respect to the raw data to the console 18.

Figure 13:
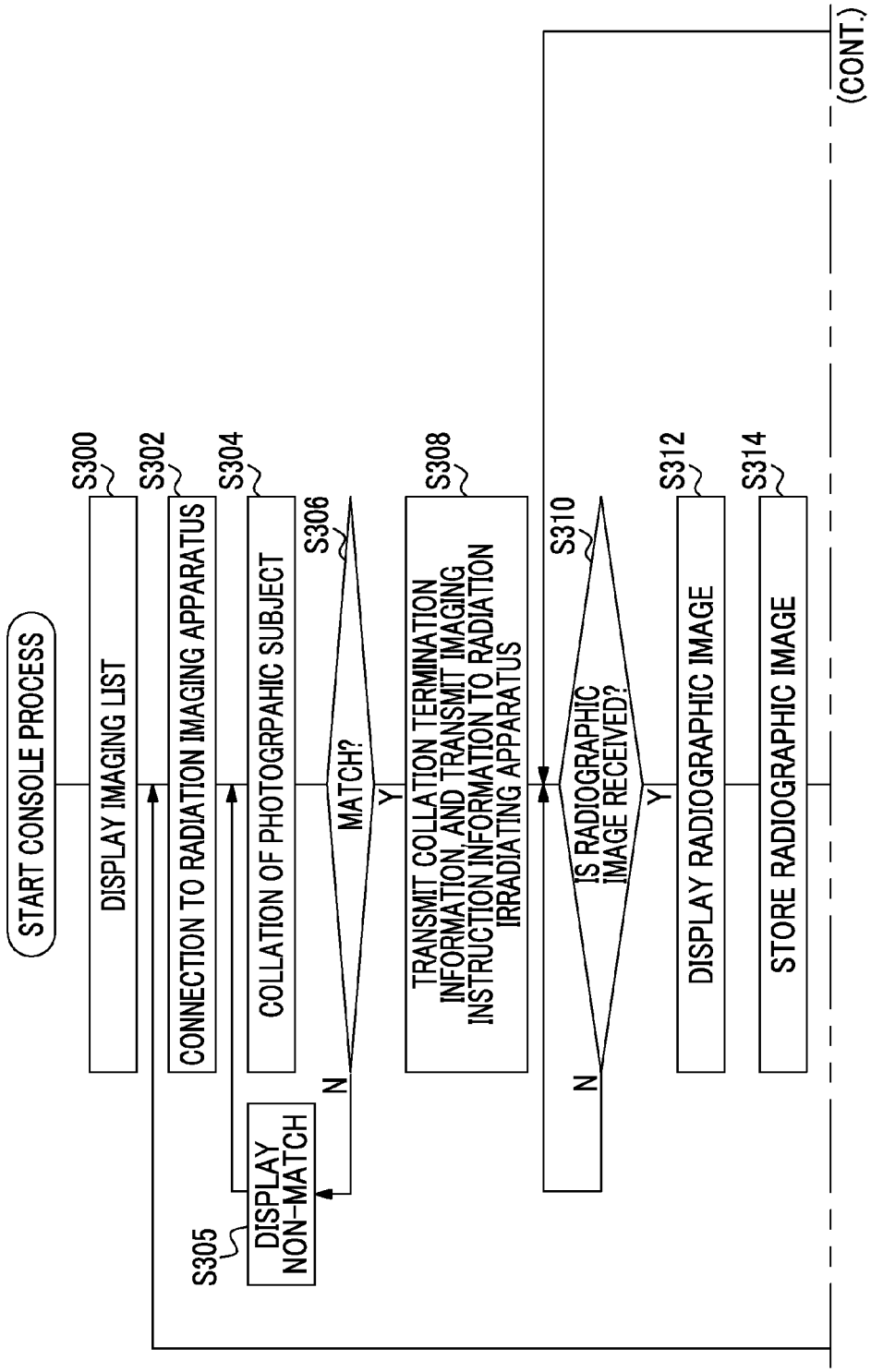
FIG. 13 is a flowchart illustrating an example of the flow of a console process executed by a console control unit of the first embodiment.

In the console 18, the radiographic image for image reading is displayed on the display 56, based on the image data of the received radiographic image for image reading (see step S312 in FIG. 13). The user refers to and confirms the radiographic image displayed on the display 56 of the console 18, and gives an instruction about the necessity of re-imaging to the radiographic image capturing apparatus 14 using the operation unit 60 of the console 18. Specifically, in a case where a message indicating that the re-imaging is necessary is input by the user using the operation unit 60, the console 18 transmits re-imaging instruction information to the radiographic image capturing apparatus 14 (see step S318 in FIG. 13). Further, in a case where a message indicating that the re-imaging is not necessary is input by the user through the operation unit 60, the console 18 transmits imaging completion instruction information to the radiographic image capturing apparatus 14 (see step S320 in FIG. 13).

In the next step S180, the imaging control unit 22 determines whether or not the re-imaging instruction information is received from the console 18 to determine whether to perform the re-imaging. Here, in a case where the determination is affirmative, the procedure returns to step S172 to repeat the capturing of the radiographic image of the photographic subject W again. On the other hand, in a case where the determination in step S180 is negative, the imaging control unit 22 considers that the imaging completion instruction information is received from the console 18, and the procedure proceeds to step S182.

In the radiographic image capturing apparatus 14 of the embodiment, in a case where capturing of plural radiographic images is instructed with respect to one piece of order information, for example, in a case where plural radiographic images are captured with respect to the same photographic subject W, the processes of steps S172 to 180 are repeatedly performed.

If the capturing of the radiographic images is completed, the imaging control unit 22 deletes the image data (raw data) of the radiographic image stored in the memory 24 in step S182.

In the next step S184, the imaging control unit 22 determines whether or not the entirety of imaging is terminated. Here, in a case where it is determined that the entirety of imaging is not terminated, the procedure proceeds to step S186, and the imaging control unit 22 perform a control for bringing the radiation detector 20 into the standby state.

If the entirety of imaging is terminated, the console 18 transmits the termination instruction information (see step S328 in FIG. 13). Thus, in a case where the termination instruction information is not received in step S184, the imaging control unit 22 of the radiographic image capturing apparatus 14 determines that the entirety of imaging is not terminated. On the other hand, in a case where the termination instruction information is received, it is determined that the entirety of imaging is terminated.

In step S184, in a case where it is determined that the entirety of imaging is terminated, the imaging control unit 22 terminates the normal mode process.

According to the above-described normal mode process, as shown in FIG. 6, for example, the image data of the radiographic image for image reading generated from the radiographic image obtained from the imaging is transmitted to the console 18 from the radiographic image capturing apparatus 14. Further, the console 18 stores the radiographic image for image reading and at least one of the photographic subject information or the order information in the storage unit 52 in association.

In this way, if the normal mode process is terminated, the procedure proceeds to step S112 of the imaging process (see FIG. 3). If the normal mode process is terminated, the connection (communication) of the radiographic image capturing apparatus 14 and the console 18 is released by the console 18 (see step S330 in FIG. 13).

In step S112, the imaging control unit 22 determines whether or not the power switch of the radiographic image capturing apparatus 14 is in an off state. In a case where the power switch is not in the off state, the procedure proceeds to step S114.

In step S114, the imaging control unit 22 performs a control for bringing the host apparatus into a sleep state. The "sleep state" in this embodiment represents a state where only the CPU of the imaging control unit 22 is operated, which is a state where power consumption is less than that in the standby state.

In the next step S116, the imaging control unit 22 determines whether or not the control apparatus is connected, in a similar manner to step S102. In a case where the control apparatus is not connected, the sleep state is continued. On the other hand, in a case where the control apparatus is connected, the procedure proceeds to step S118. In step S118, the imaging control unit 22 performs a control for causing the host apparatus return to the standby state from the sleep state, and then, the procedure returns to step S104 to repeat the imaging process.

On the other hand, in step S112, in a case where the power switch is in the off state, the imaging control unit 22 terminates the imaging process.

In the radiographic image capturing apparatus 14 of this embodiment, the imaging control unit 22 selectively performs communication with any one of the portable information terminal 16 and the console 18 which function as the control apparatus through the I/F unit 28. By selectively performing the communication, the radiographic image capturing apparatus 14 is connected to the control apparatus. In capturing the radiographic image, in a case where the connected control apparatus is the portable information terminal 16, the imaging control unit 22 selects the memory mode as the imaging mode. Further, in capturing a radiographic image, in a case where the connected control apparatus is the console 18, the imaging control unit 22 selects the normal mode as the imaging mode.

In the memory mode, the imaging control unit 22 generates a preview image and transmits image data thereof to the portable information terminal 16, and stores image data of radiographic images obtained by imaging corresponding to plural pieces of order information in the memory 24. Further, in the normal mode, the imaging control unit 22 generates a radiographic image for image reading and transmits image data thereof to the console 18, and does not store the image data of the radiographic images by imaging corresponding to plural pieces of order information in the memory 24.

Thus, in the radiographic image capturing control apparatus 14 of this embodiment, it is possible to select an imaging mode suitable for the connected control apparatus.

Next, an operation of the portable information terminal 16 in a case where a radiographic image is captured under the control of the portable information terminal 16 will be described.

FIG. 8 is a flowchart illustrating an example of the flow of a terminal process executed by the terminal control unit 30 of the portable information terminal 16 of this embodiment. In the portable information terminal 16 of this embodiment, the terminal control unit 30 executes a terminal process program stored in the ROM of the host apparatus, to thereby execute the terminal process.

The terminal process is performed in a case where the portable information terminal 16 is disposed at a position where the portable information terminal 16 can communicate with the radiographic image capturing apparatus 14, and in a case where an execution instruction of the terminal process is performed by the user through the operation unit 40.

In step S200 of FIG. 8, the terminal control unit 30 displays an imaging list on the display 36. In the portable information terminal 16 of this embodiment, the imaging list is acquired in advance from an external system such as the console 18 or an RIS, or the like, and is stored in the storage unit 32, or the like, but a timing when the imaging list is acquired is not limited thereto. In the terminal process, the imaging list may be acquired from the console 18 or the external system immediately before the process of step S200 is executed.

Figure 9:
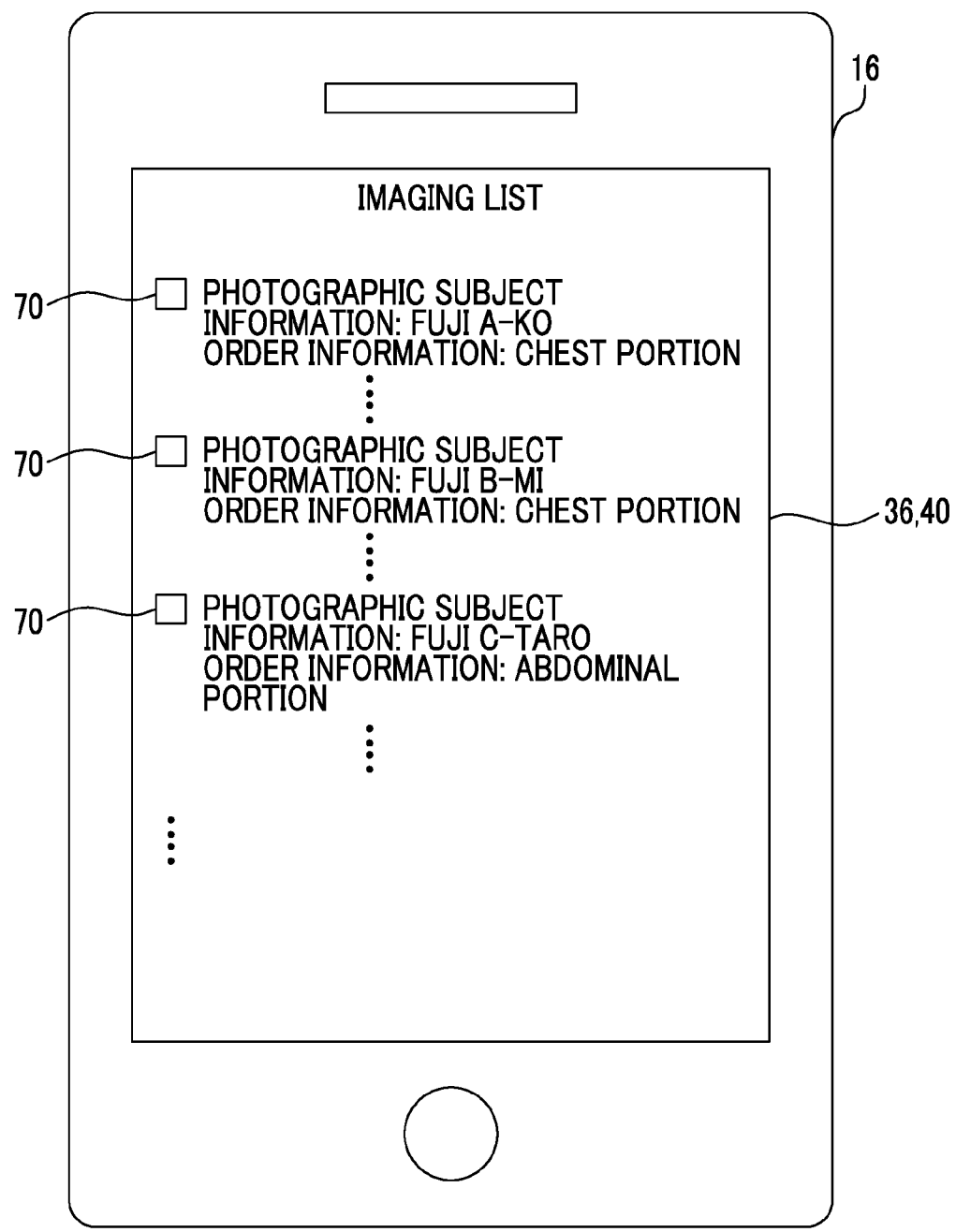
FIG. 9 is a schematic diagram illustrating a specific example of a state where an imaging list is displayed on a display of the portable information terminal.

FIG. 9 is a schematic diagram illustrating a specific example of a state where the imaging list is displayed on the display 36 of the portable information terminal 16. In the specific example shown in FIG. 9, as the imaging list, plural imaging processes individually corresponding to plural pieces of order information are displayed, and in each imaging process, a check box 70, subject information, and order information are displayed. The check box 70 represents whether imaging is completed, and in a case where the check box 70 is checked, it means that the imaging is completed.

As the imaging list is displayed on the display 36, the user can confirm imaging to be performed from the imaging list.

In the next step S202, the terminal control unit 30 connects the host apparatus to the radiographic image capturing apparatus 14. Specifically, the terminal control unit 30 performs communication with the radiographic image capturing apparatus 14, to thereby connect the host apparatus to the radiographic image capturing apparatus 14. In this way, as the radiographic image capturing apparatus 14 is connected to the portable information terminal 16 are connected, it is possible to control the radiographic image capturing apparatus 14 using the portable information terminal 16.

Further, as described above, as the portable information terminal 16 is connected, the radiographic image capturing apparatus 14 performs the memory mode process (see FIG. 5). Further, the radiographic image capturing apparatus 14 transmits information indicating that the mode is changed to the memory mode as described above and information indicating the number of photographable images to the portable information terminal 16, while the memory mode process is being executed (see step S130 in FIG. 5).

Figure 10:
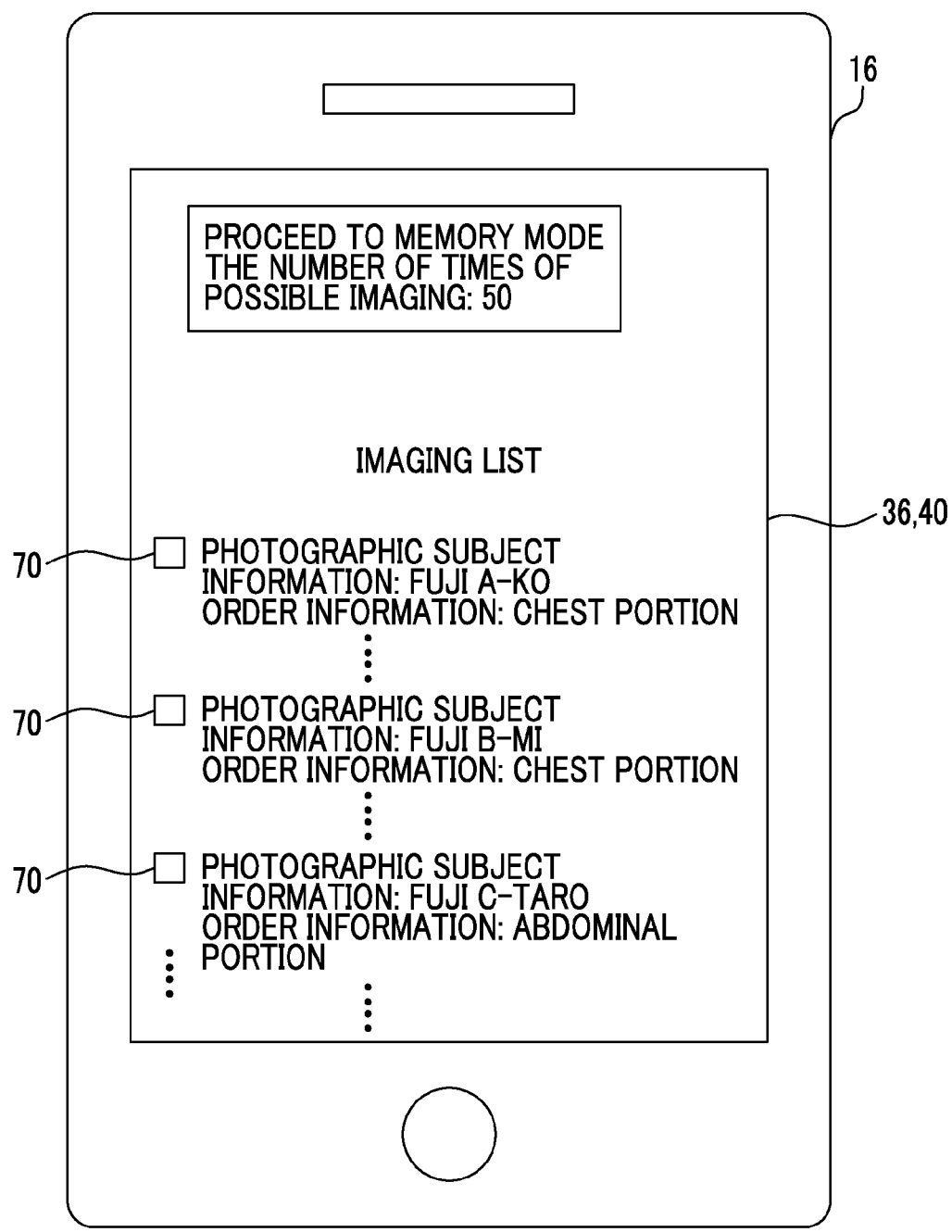
FIG. 10 is a schematic diagram illustrating a specific example of a state where information indicating that a mode is changed to a memory mode and information indicating the number of photographable images are displayed on the display of the portable information terminal.

In the next step S204, the terminal control unit 30 receives the information indicating that the mode is changed to the memory mode and the information indicating the number of photographable images, and displays the result on the display 36. FIG. 10 is a schematic diagram illustrating a specific example of a state where the information indicating that the mode is changed to the memory mode and the information indicating the number of photographable images are displayed on the display 36 of the portable information terminal 16. In FIG. 10, the state where the information indicating that the mode is changed to the memory mode and the information indicating the number of photographable images together with the imaging list are displayed on the display is displayed, but the display method is not limited thereto. For example, only the information indicating that the mode is switched to be changed to the memory mode from the state where the imaging list is displayed on the display 36 (see FIG. 9) and the information indicating the number of photographable images may be displayed thereon.

The user confirms the information displayed on the display 36. In performing imaging depending on the imaging list, in a case where the number of photographable images is insufficient, the user changes the radiographic image capturing apparatus 14 to another apparatus, and in a case where the memory 24 of the radiographic image capturing apparatus 14 is detachable and attachable, the user changes the radiographic image capturing apparatus 14 to another memory 24, to thereby make it possible to continue the capturing of the radiographic image.

The radiographic image capturing apparatus 14 may select or switch the imaging mode according to the number of photographable images. For example, in a case where the order information is obtained, the mode may be switched from the memory mode to the normal mode, in a case where the number of photographable images is smaller than the number of photographable images corresponding to one piece of order information, or in a case where the number of photographable images is smaller than the number of photographable images of all of radiographic images included in the imaging list.

However, generally, in a case where the capturing of the radiographic image is performed, differently from the order information included in the imaging list, imaging to be additionally performed (hereinafter, referred to as "additional imaging") may be necessary. In this case, if the portable information terminal 16 is not connected to the console 18 or the external system, in a state where order information corresponding to the additional imaging is not issued, the capturing of the radiographic image is first performed, and after the console 18 is connected to the external system after the imaging, association of the order information and the image data of the radiographic image is performed.

In a case where such additional imaging is present, the user inputs photographic subject information and imaging conditions using the operation unit 40.

Then, in the next step S206, the terminal control unit 30 detects whether or not the photographic subject information and the imaging conditions are input through the operation unit 40 using the operation input detection unit 38, to thereby determine whether or not the additional imaging is present. Here, in a case where the additional imaging is present, the procedure proceeds to step S212 from step S206, and the terminal control unit 30 receives the photographic subject information and the imaging conditions input through the operation unit 40 by the user, and then, the procedure proceeds to step S214.

On the other hand, in a case where there is no additional imaging, the procedure proceeds to step S208 from step S206.

In step S208, the terminal control unit 30 performs collation of the photographic subject W. Here, the terminal control unit 30 reads, as photographic subject information, a photographic subject name disclosed in a name tag of a photographic subject W, a medical record card, or the like, a bar code, and a two-dimensional code such as a QR code (registered trademark), and the like using the reader 33, and collates the read data with the imaging list information, to thereby perform the collation of the photographic subject W. Further, for example, in a case where a photo image including the face of the photographic subject W is included in the imaging list information, the terminal control unit 30 may take a picture of the face of the photographic subject W using the reader 33, and may perform face recognition or the like using an image of the photographed face, for example, to thereby perform the collation of the photographic subject W. In this way, the collation method of the photographic subject W is not particularly limited, and any method capable of collating the photographic subject W to be photographed with the imaging list information may be used. In addition, fingerprint recognition or the like may be used.

In the next step S210, the terminal control unit 30 determines whether or not the photographic subject W matches a photographic subject W included in the imaging list information, based on the collation result in the process of step S208. In this way, by performing the collation of the photographic subject W, the portable information terminal 16 of this embodiment can suppress capturing of a radiographic image of the photographic subject W which is not scheduled to be imaged.

In a case where the photographic subject W does not match the imaging list information, the procedure proceeds to step S211, and the terminal control unit 30 displays information indicating the non-match on the display 36. According to the information indicating the non-match between the photographic subject W and the imaging list information displayed on the display 36, the user confirms that the photographic subject W is not included in the imaging list. Further, the user changes a capturing target of a radiographic image to the photographic subject W which is included in the imaging list and is scheduled to be imaged, and causes the portable information terminal 16 to perform collation of the changed photographic subject W. Thus, in the case of the non-match, the procedure proceeds to step S208, and the terminal control unit 30 performs collation of the photographic subject W again.

On the other hand, in a case where the photographic subject W matches the imaging list information, the procedure proceeds to step S214. In step S214, the terminal control unit 30 transmits collation termination information to the radiographic image capturing apparatus 14. In this embodiment, the collation termination information represents that the collation of the photographic subject W is terminated, and includes information for instructing the radiographic image capturing apparatus 14 to capture a radiographic image. Thus, as described above, in a case of receiving the collation termination information from the portable information terminal 16, the radiographic image capturing apparatus 14 determines that the capturing of the radiographic imaging is started (see step S132 in FIG. 5).

Further, in step S214, the terminal control unit 30 transmits imaging instruction information for a radiographic image to the irradiator 12 based on order information. A timing when the imaging instruction information for the radiographic image is transmitted to the irradiator 12 is not limited to this embodiment, and after the collation termination information is transmitted, and in a case where irradiation starting with the radiation R is instructed from the user through the operation unit 40, the terminal control unit 30 may transmit the imaging instruction information to the irradiator 12.

In the radiographic image capturing apparatus 14, the capturing of the radiographic image is performed through processes of steps S134 to S142 of the memory mode process shown in FIG. 5, as described above, and image data indicating a preview image generated based on the radiographic image obtained by imaging is transmitted to the portable information terminal 16.

Thus, in the next step S216, the terminal control unit 30 determines whether image data of the preview image is received. The procedure waits until the image data is received, and if the image data is received, the procedure proceeds to step S218.

Figure 11:
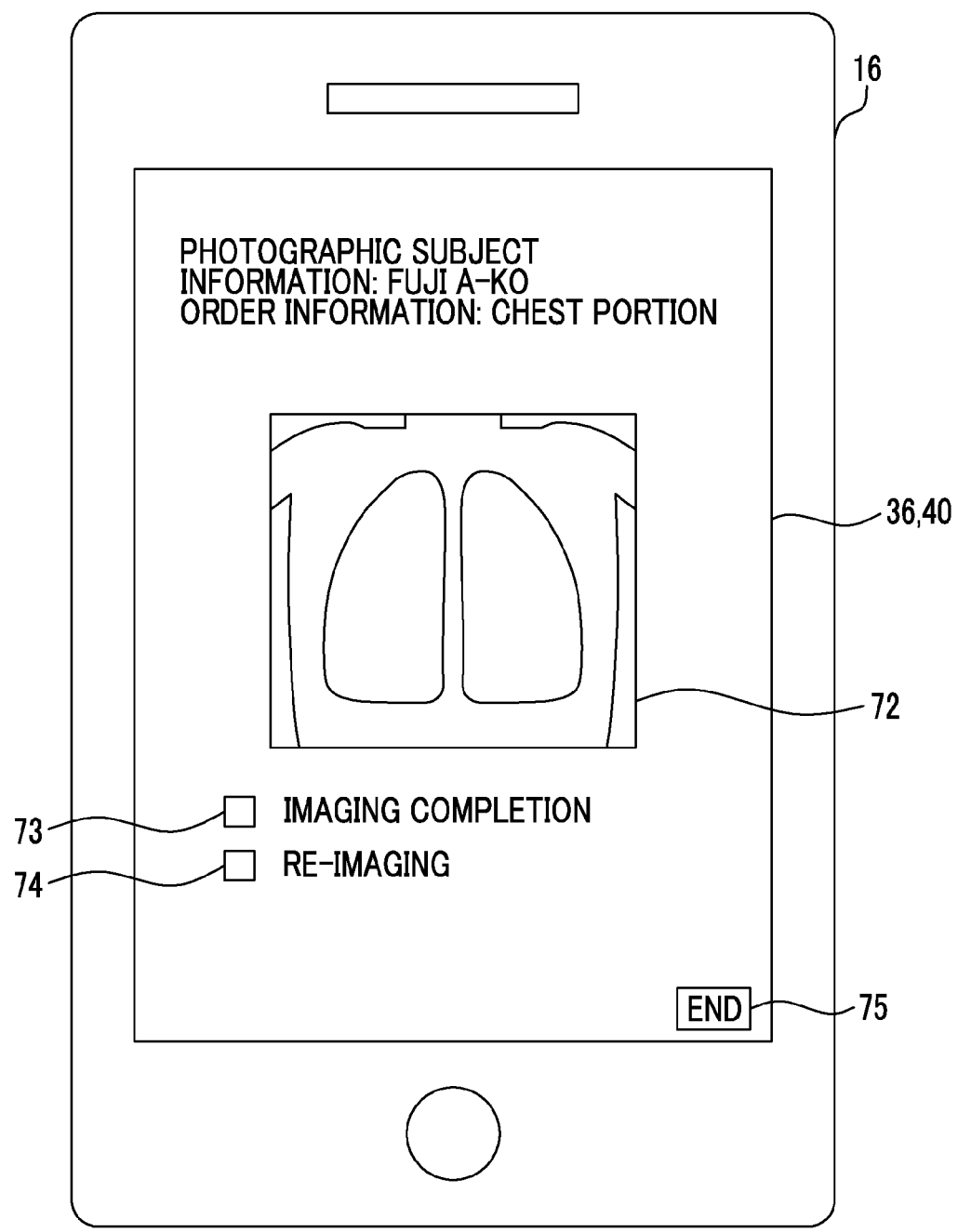
FIG. 11 is a schematic diagram illustrating a specific example of a state where a preview image is displayed on the display of the portable information terminal.

In step S218, the terminal control unit 30 displays the preview image on the display 36 using the received image data. FIG. 11 shows a schematic diagram illustrating a specific example of a state where a preview image 72 is displayed on the display 36 of the portable information terminal 16.

The user confirms the preview image 72, and determines whether to perform re-imaging. The user instructs the re-imaging in a case where a desired portion is not included in the displayed preview image 72, in a case of camera shaking, picture blur, or the like is generated in an image, or in a case where the radiographic image obtained by imaging is not appropriate. Further, the radiographic image capturing apparatus 14 of this embodiment detects irradiation starting with the radiation R using the host apparatus to capture the radiographic image in an asynchronous manner with the irradiator 12. Thus, due to noise such as a shock to the radiographic image capturing apparatus 14, the irradiation starting with the radiation R may be erroneously detected to capture the radiographic image, and the preview image may be transmitted to the portable information terminal 16. In such a case, the user instructs re-imaging.

Specifically, in the portable information terminal 16 of this embodiment, in a case where the user instructs the re-imaging, an operation of checking the check box 74 displayed on the display 36 is performed, and then, operates an end button 75.

On the other hand, in a case where the imaging is completed without performing the re-imaging, the user performs an operation of checking the check box 73 displayed on the display 36, and then, operates the end button 75.

The terminal control unit 30 detects these operations using the operation input detection unit 38. Further, in a case where it is detected that the instruction operation of performing the re-imaging is performed by the user, the terminal control unit 30 causes the procedure to proceed to step S222. Further, the terminal control unit 30 transmits the re-imaging instruction information to the radiographic image capturing apparatus 14, and then, the procedure returns to step S216.

On the other hand, in a case where it is detected that the instruction operation of completing the imaging is performed by the user, the terminal control unit 30 causes the procedure to proceed to step S224. In step S224, the terminal control unit 30 transmits the imaging completion instruction information to the radiographic image capturing apparatus 14, and then, the procedure proceeds to step S226.

In step S226, the terminal control unit 30 transmits at least one of the photographic subject information or the order information to the radiographic image capturing apparatus 14. Specifically, in a case where the order information of the imaged photographic subject W is present, the terminal control unit 30 transmits the order information, and in a case where the order information of the imaged photographic subject W is not present, for example, in the case of additional imaging, the terminal control unit 30 transmits the photographic subject information. As described above, at least one of the photographic subject information or the order information transmitted to the radiographic image capturing apparatus 14 is stored in the memory 24 of the radiographic image capturing apparatus 14 in association with the image data of the radiographic image (see step S148 in FIG. 5).

Figure 12:
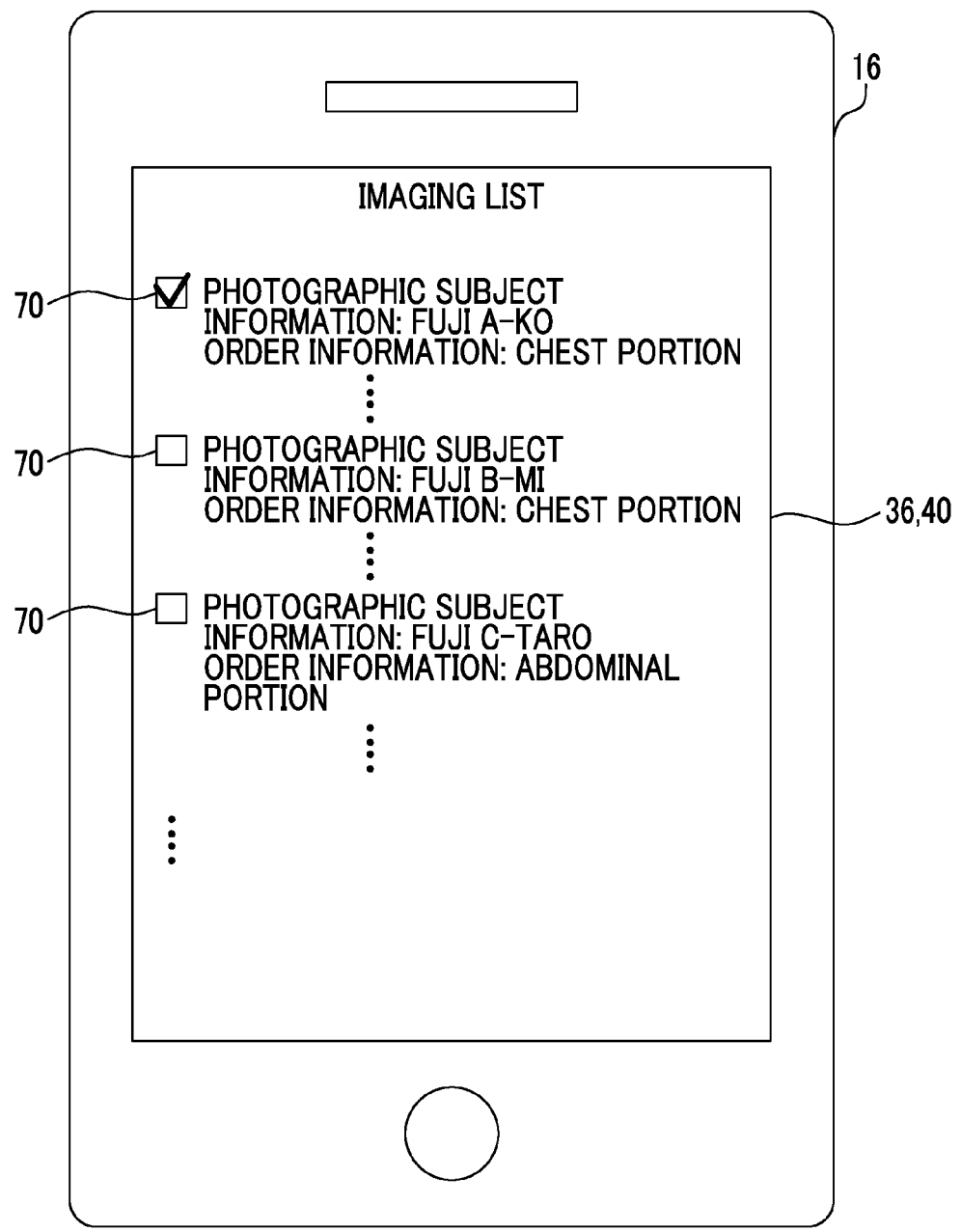
FIG. 12 is a schematic diagram illustrating a specific example of a state where an imaging list including information indicating that imaging is finished is displayed on the display of the portable information terminal.

In the next step S228, the terminal control unit 30 displays the imaging list on the display 36 again. Here, the terminal control unit 30 displays a state where the check box 70 corresponding to the imaging-completed order information is checked. FIG. 12 is a schematic diagram illustrating a specific example of a state where an imaging list including order information indicating that imaging is completed is displayed on the display 36 of the portable information terminal 16. In the specific example shown in FIG. 12, the check box 70 corresponding to "photographic subject information: FUJI A-KO, order information: chest portion, etc." displayed on the top is checked, and represents that imaging corresponding to the information is completed. The user can confirm whether order information for which capturing of a radiographic image is not terminated is present according to whether or not the check box 70 is checked.

The capturing of the radiographic image is not limited to the order disclosed in the imaging list. The imaging may be performed in the order of the collation completion in the processes of steps S208 to S210.

In the next step S230, the terminal control unit 30 determines whether or not the entirety of imaging included in the imaging list is terminated. In a case where it is determined that the entirety of imaging is not terminated, the procedure returns to step S206, and repeats the terminal process. On the other hand, in a case where it is determined that the entirety of imaging is terminated, the procedure proceeds to step S232.

In step S232, the terminal control unit 30 transmits termination instruction information to the radiographic image capturing apparatus 14. In the next step S234, the terminal control unit 30 releases the connection with the radiographic image capturing apparatus 14, and then, terminates the terminal process. Specifically, the terminal control unit 30 cuts off (terminates) the communication with the radiographic image capturing apparatus 14, to thereby release the connection with the radiographic image capturing apparatus 14.

As described above, in the portable information terminal 16 of this embodiment, in a case of controlling the radiographic image capturing apparatus 14 in the capturing of the radiographic image, the terminal control unit 30 receives image data of the preview image from the radiographic image capturing apparatus 14 to display the result on the display 36.

The portable information terminal 16 may perform communication with another control apparatus such as the console 18, or an external system while the capturing of the radiographic image is being performed, but does not receive an instruction relating to an imaging control therefrom. As the portable information terminal 16 communicates with another control apparatus or the external system in this way, it is possible to detect a progressing state of imaging from another control apparatus or the external system.

Next, an operation of the console 18 in a case where a radiographic image is captured under the control of the console 18 will be described.

FIG. 13 is a flowchart illustrating an example of the flow of a console process executed by the control unit 50 of the console 18 of this embodiment. In the console 18 of this embodiment, the control unit 50 executes a console processing program stored in a ROM thereof, to thereby execute the console process.

The console process is executed in a case where power is supplied to a power switch (not shown) of the console 18, or in a case where a message for performing capturing of a radiographic image is instructed by the operation unit 60.

In the console 18, in a case where additional imaging which is not included in the imaging list is generated, differently from the above-described portable information terminal 16, it is assumed that the order information may be acquired from the external system such as RIS and imaging (order information) is added to the imaging list.

In step S300 of FIG. 13, the control unit 50 displays the imaging list on the display 56. In the console 18 of this embodiment, the imaging list is acquired in advance from the external system such as RIS, and is stored in the storage unit 52, or the like, but a timing when the imaging list is acquired is not limited thereto. In the console process, the imaging list may be acquired from the external system immediately before the process of step S300 is executed. Display of the imaging list is the same as in step S200 of the above-described terminal process in the portable information terminal 16.

In the next step S302, the control unit 50 connects the host apparatus and the radiographic image capturing apparatus 14. Specifically, the control unit 50 performs communication with the radiographic image capturing apparatus 14, to thereby connect the host apparatus and the radiographic image capturing apparatus 14. In this way, as the radiographic image capturing apparatus 14 and the console 18 are connected to each other, it is possible to control the radiographic image capturing apparatus 14 using the console 18.

Further, as described above, in the radiographic image capturing apparatus 14, due to the connection to the console 18, since the normal mode instead of the memory mode is selected as the imaging mode, the normal mode process (see FIG. 7) is performed.

In the next step S304, the control unit 50 performs collation of the photographic subject W. A method of collating the photographic subject W in the console 18 may be the same as in step S208 of the above-described terminal process in the portable information terminal 16 using the reader 61.

In the next step S306, the control unit 50 determines whether or not the photographic subject W matches a photographic subject W included in the imaging list information based on the collation result in the process of step S304. In a case where the photographic subject W does not match the imaging list information, the procedure proceeds to step S305, and the control unit 50 displays information indicating the non-match on the display 56. Further, the procedure returns to step S304, and the control unit 50 performs collation of the changed photographic subject W.

On the other hand, in a case where the photographic subject W matches the imaging list information, the procedure proceeds to step S308. In step S308, the control unit 50 transmits collation termination information to the radiographic image capturing apparatus 14. As described above, in a case where the collation termination information is received from the console 18, the radiographic image capturing apparatus 14 determines that capturing of a radiographic image is started (see step S170 in FIG. 7).

Further, in step S308, the control unit 50 instructs the irradiator 12 to perform the capturing of the radiographic image based on the order information.

In the radiographic image capturing apparatus 14, as described above, the capturing of the radiographic image is performed through the processes of steps S172 to S178 of the normal mode process, and image data of the radiographic image obtained by the imaging is transmitted to the console 18.

Thus, in step S310, the control unit 50 determines whether or not the image data of the radiographic image is received. The procedure waits until the image data is received, and then, if the image data is received, the procedure proceeds to step S312.

In step S312, the control unit 50 displays the radiographic image on the display 56 using the received image data of the radiographic image. Further, in the next step S314, the control unit 50 stores the received image data of the radiographic image in the storage unit 52.

Figure 14:
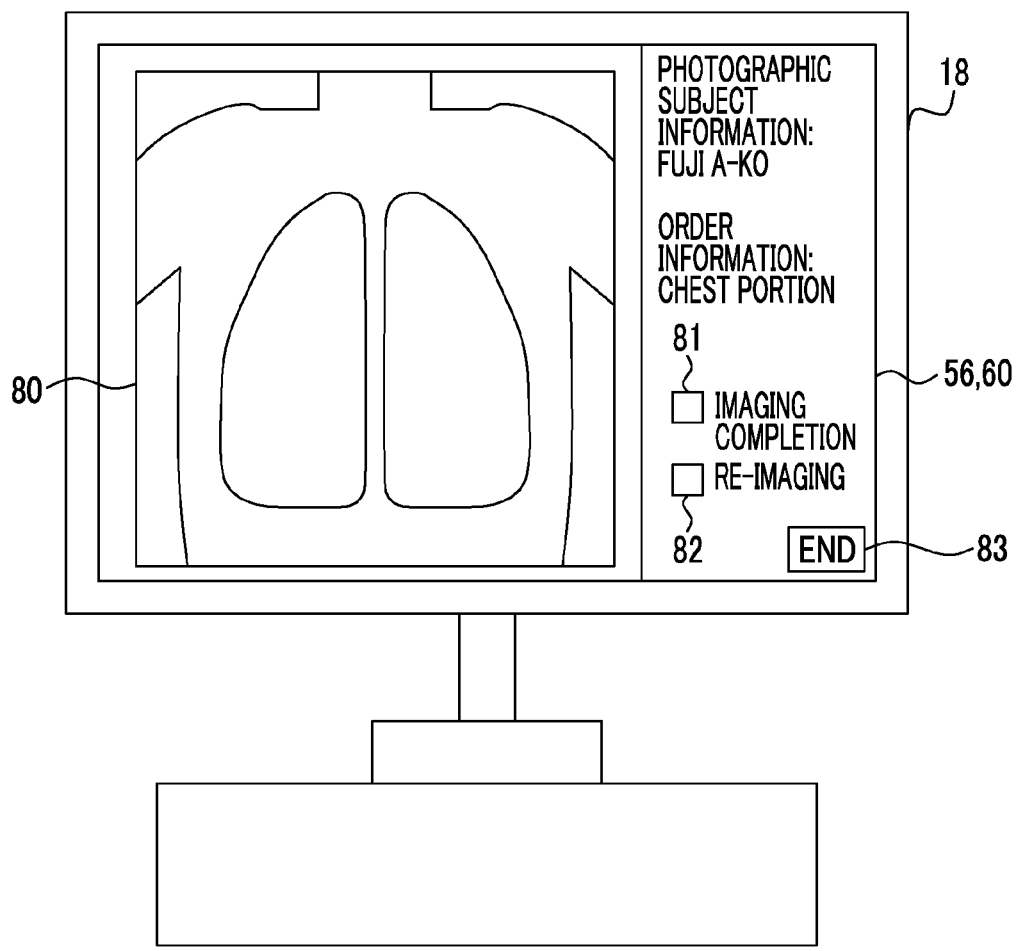
FIG. 14 is a schematic diagram illustrating a specific example of a state where a radiographic image for image reading is displayed on a display of a console.

In this embodiment, as described above, the radiographic image capturing apparatus 14 transmits the image data of the radiographic image for image reading to the console 18. Thus, the control unit 50 displays a radiographic image for image reading on the display 56 as the radiographic image. FIG. 14 is a schematic diagram illustrating a specific example of a state where a radiographic image 80 for image reading is displayed on the display 56 of the console 18.

The radiographic image displayed on the display 56 by the control unit 50 is not limited to this embodiment. For example, image processing is performed with respect to the image data of the radiographic image received from the radiographic image capturing apparatus 14, and a radiographic image after the image processing may be displayed on the display 56. As such a radiographic image, for example, a preview image may be displayed on the display 56.

The user confirms the radiographic image 80 for image reading, and determines whether or not to perform re-imaging. In the console 18 of this embodiment, the user checks a check box 82 displayed on the display 56 in a case where the user instructs the re-imaging, and then, operates an end button 83.

On the other hand, in a case where the imaging is completed without performing the re-imaging, the user checks a check box 81 displayed on the display 56, and then, operates the end button 83.

In the next step S316, the control unit 50 detects the operations using the operation input detector 58 of the console 18. In a case where it is detected that the instruction operation for performing the re-imaging is performed by the user, the control unit 50 causes the procedure to proceed to step S318. In step S318, the control unit 50 transmits re-imaging instruction information to the radiographic image capturing apparatus 14, and then, the procedure returns to step S310.

On the other hand, in a case where the re-imaging is not performed, the procedure proceeds to step S320. In step S320, the control unit 50 transmits imaging completion instruction information to the radiographic image capturing apparatus 14, and then, the procedure proceeds to step S322.

In step S322, the control unit 50 stores the order information in association with the image data of the radiographic image in the storage unit 52. As described above, since the order information can be acquired before the capturing of the radiographic image in the console 18, here, the order information is stored in association with the image data of the radiographic image. Differently from the console 18 of this embodiment, and similar to the above-described portable information terminal 16, in a case where additional imaging where the order information cannot be acquired (order information is not issued) is generated, photographic subject information input by the user may be acquired, and then, the acquired photographic subject information in association with the image data of the radiographic image may be stored in the storage unit 52, similar to the portable information terminal 16.

In the next step S324, the control unit 50 displays the imaging list on the display 56 again. The display of the imaging list is the same as in step S228 of the above-described portable information terminal 16, in which a state where a check box corresponding to order information for which imaging is completed is checked is displayed.

In the next step S326, the control unit 50 determines whether or not the entirety of imaging included in the imaging list is terminated. When it is determined that the entirety of imaging is not terminated, the procedure returns to step S302, and the console process is repeated. On the other hand, in a case where it is determined that the entirety of imaging is terminated, the procedure proceeds to step S328.

In step S328, the control unit 50 transmits termination instruction information to the radiographic image capturing apparatus 14. In the next step S330, the control unit 50 releases the connection to the radiographic image capturing apparatus 14, and then terminates the console process. Specifically, the control unit 50 cuts off (terminates) the communication with the radiographic image capturing apparatus 14 to release the connection to the radiographic image capturing apparatus 14.

As described above, in the console 18 of this embodiment, in a case of controlling the radiographic image capturing apparatus 14 in capturing the radiographic image, the control unit 50 receives the image data of the radiographic image for image reading from the radiographic image capturing apparatus 14 and displays the result on the display 56. Further, the console 18 stores the received image data of the radiographic image for image reading in association with the order information in the storage unit 52.

Second Embodiment

In the first embodiment, in a case where the radiographic image capturing apparatus 14 is operated in the memory mode (in a case where the memory mode process is performed), after the radiographic image is captured, at least one of the photographic subject information or the order information is received from the portable information terminal 16, and the result is stored in the memory 24 in association with the image data of the radiographic image. On the other hand, in a second embodiment, a case where the radiographic image capturing apparatus 14 receives at least one of the photographic subject information or the order information from the portable information terminal 16 before the radiographic image is captured and the result is stored in the memory 24 in association with the image data of the radiographic image after capturing will be described.

Since a configuration (see FIGS. 1 and 2) of a radiographic image capturing system 10 of this embodiment is the same as in the first embodiment, detailed description thereof will not be repeated.

In the radiographic image capturing system 10 of this embodiment, a terminal process executed by the portable information terminal 16 is different from that in the first embodiment.

FIG. 15 is a flowchart illustrating an example of the flow of a terminal process executed by the terminal control unit 30 of the portable information terminal 16 of this embodiment. In FIG. 15, the same step numbers as in FIG. 8 are given to the steps of performing the same processes as in the terminal process shown in FIG. 8, and description thereof will not be repeated.

An overall flow of the terminal process executed by the portable information terminal 16 in this embodiment is the same as in the terminal process (see FIG. 8) in the first embodiment. However, in the terminal process of this embodiment, the process of step S213 corresponding to step S226 (see FIG. 8) in the terminal process of the first embodiment is executed between step S210 and step S214.

Namely, in step S210, in a case where the terminal control unit 30 determines that the photographic subject W matches the imaging list information, the procedure proceeds to step S213. In step S213, the terminal control unit 30 transmits at least one of the photographic subject information or the order information to the radiographic image capturing apparatus 14, similar to step S226 in the terminal process of the first embodiment, and then, the procedure proceeds to step S214.

In this way, in the portable information terminal 16 of this embodiment, before collation termination information is transmitted to the radiographic image capturing apparatus 14 to start capturing the radiographic image, at least one of the photographic subject information or the order information is transmitted to the radiographic image capturing apparatus 14.

Thus, in the radiographic image capturing system 10 of this embodiment, the memory mode process executed by the radiographic image capturing apparatus 14 is different from that in the first embodiment. The overall flow in the imaging process (see FIG. 3) and the normal mode process (see FIG. 7), executed by the radiographic image capturing apparatus 14, are the same as in the first embodiment.

FIG. 16 is a flowchart illustrating an example of the flow of a memory mode process executed by the imaging control unit 22 of the radiographic image capturing apparatus 14 of this embodiment. In FIG. 16, the same step numbers as in FIG. 5 are given to the steps of performing the same processes as in the memory mode process shown in FIG. 5, and description thereof will not be repeated.

An overall flow of the memory mode process executed by the radiographic image capturing apparatus 14 in this embodiment is the same as in the memory mode process (see FIG. 5) in the first embodiment. However, in the memory mode process of this embodiment, the process of step S131 corresponding to step S146 (see FIG. 5) in the memory mode process of the first embodiment is executed between step S130 and step S132.

Namely, in step S130, after the imaging control unit 22 transmits information indicating that the mode is changed to the memory mode and the information indicating the number of photographable images to the portable information terminal 16, the procedure proceeds to step S131. In step S131, the imaging control unit 22 receives at least one of the photographic subject information or the order information from the portable information terminal 16, similar to step S146 in the memory mode process of the first embodiment, and then, the procedure proceeds to step S132.

As described above, in the radiographic image capturing apparatus 14 of this embodiment, in the memory mode process, before the radiographic image is captured, at least one of the photographic subject information or the order information is received from the portable information terminal 16. Further, as described above, in step S148, the imaging control unit 22 stores at least one of the photographic subject information or the order information in association with the image data of the radiographic image in the memory 24 of the radiographic image capturing apparatus 14.

The console process (see FIG. 13) executed by the console 18 is the same as in the first embodiment.

Third Embodiment

In the first and second embodiments, in a case where the radiographic image capturing apparatus 14 is operated in the memory mode, the radiographic image capturing apparatus 14 stores the image data of the radiographic image in association with at least one of the photographic subject information or the order information in the memory 24. On the other hand, in a third embodiment, a case where the portable information terminal 16 associates the image data of the radiographic image with at least one of the photographic subject information or the order information will be described.

Since a configuration (see FIGS. 1 and 2) of a radiographic image capturing system 10 of this embodiment is the same as in the first embodiment, detailed description thereof will not be repeated.

In this embodiment, a memory mode process executed by the radiographic image capturing apparatus 14 is different from that in the first embodiment. An overall flow in the imaging process (see FIG. 3) and the normal mode process (see FIG. 7), executed by the radiographic image capturing apparatus 14, are the same as in the first embodiment.

Figure 17:
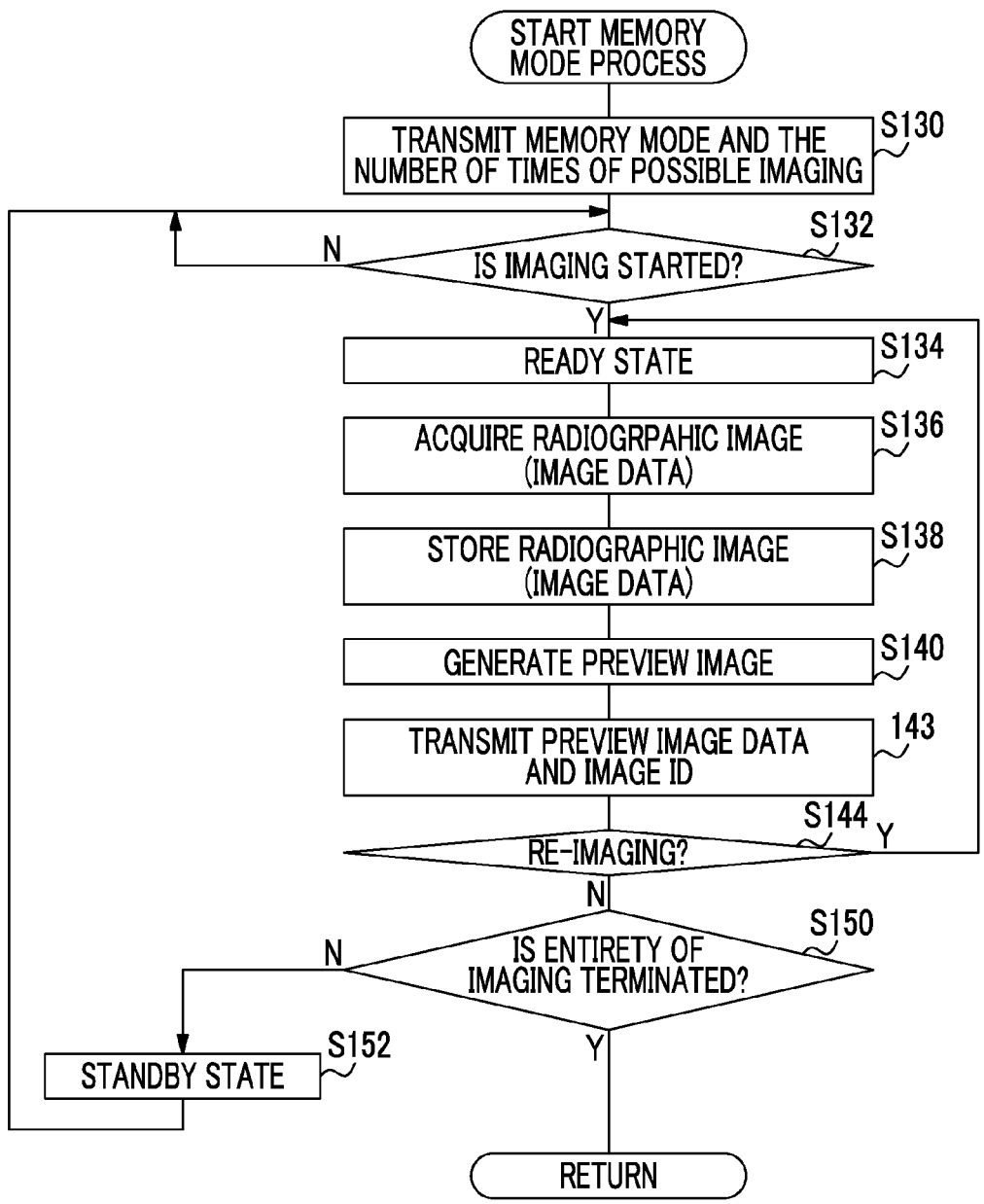
FIG. 17 is a flowchart illustrating an example of the flow of a memory mode process executed by an imaging control unit of a radiographic image capturing apparatus of a third embodiment.

FIG. 17 is a flowchart illustrating an example of the flow of a memory mode process executed by the imaging control unit 22 of the radiographic image capturing apparatus 14 of this embodiment. In FIG. 17, the same step numbers as in FIG. 5 are given to the steps of performing the same processes as in the memory mode process as shown in FIG. 5, and description thereof will not be repeated. Further, FIG. 18 is a diagram illustrating a concept of the memory mode process in the radiographic image capturing apparatus 14 of the third embodiment.

The memory mode process executed by the radiographic image capturing apparatus 14 in this embodiment is the same as the memory mode process (see FIG. 5) in the first embodiment in the overall flow. However, in the memory mode process of this embodiment, the imaging control unit 22 executes step S143 instead of step S142 of the memory mode process (see FIG. 5) in the first embodiment.

In the radiographic image capturing apparatus 14 of this embodiment, an image identification (ID) for specifying an individual is given to image data of a radiographic image obtained by imaging, stored in the memory 24.

Thus, in step S143 of the memory mode process of this embodiment, the imaging control unit 22 transmits image data of a preview image and an image ID given to a radiographic image corresponding to the preview image to the portable information terminal 16.

Further, the radiographic image capturing apparatus 14 of this embodiment does not perform the process of associating the image data of the radiographic image with at least one of the photographic subject information or the order information. Thus, as shown in FIG. 17, in the memory mode process of this embodiment, the imaging control unit 22 does not execute the processes of steps S146 and S148 of the memory mode process (see FIG. 5) in the first embodiment.

In this way, in the radiographic image capturing apparatus 14 of this embodiment, for example, as shown in FIG. 18, the image data of the preview image and the image ID given to the radiographic image corresponding to the preview image are transmitted to the portable information terminal 16 by the above-described memory mode process.

On the other hand, in the radiographic image capturing system 10 of this embodiment, the terminal process executed by the portable information terminal 16 is different from that in the first embodiment.

FIG. 19 is a flowchart illustrating an example of the flow of a terminal process executed by the terminal control unit 30 of the portable information terminal 16 of this embodiment. In FIG. 19, the same step numbers as in FIG. 8 are given to the steps of performing the same processes as in the terminal process shown in FIG. 8, and description thereof will not be repeated.

An overall flow of the memory mode process executed by the portable information terminal 16 in this embodiment is the same as in the terminal process (see FIG. 8) in the first embodiment. However, in the terminal process of this embodiment, the terminal control unit 30 executes step S217 instead of step S216 of the terminal process (see FIG. 8) in the first embodiment. Further, the terminal control unit 30 executes step S227 instead of step S226 of the terminal process (see FIG. 8) in the first embodiment.

As described above, image data of a preview image and an image ID given to a radiographic image corresponding to the preview image are transmitted from the radiographic image capturing apparatus 14. Thus, in step S217, the terminal control unit 30 determines whether or not the image data of the preview image and the image ID given to the radiographic image corresponding to the preview image are received. The procedure waits until the image data and the image ID are received, and if the image data and the image ID are received, the procedure proceeds to step S218.

Further, in step S227, the terminal control unit 30 stores at least one of the photographic subject information or the order information in the storage unit 32 in association with the image ID received in a case where the determination in step S217 is affirmative.

In this way, the portable information terminal 16 of this embodiment stores at least one of the photographic subject information of the captured photographic subject W or the order information in the storage unit 32 in association with an image ID given to a radiographic image of the photographic subject W stored in the memory 24 of the radiographic image capturing apparatus 14, in the process of step S227.

Thus, after imaging, by referring to the image data of the radiographic image stored in the memory 24 of the radiographic image capturing apparatus 14, and at least one of the photographic subject information or the order information stored in the storage unit 32 of the portable information terminal 16, it is possible to associate the image data of the radiographic image with at least one of the photographic subject information or the order information based on the image ID, in the console 18. In a case where the portable information terminal 16 receives the order information from the console 18, information (console ID or the like) indicating the console 18 is transmitted to the radiographic image capturing apparatus 14, and the radiographic image capturing apparatus 14 stores the information in association with the image data of the radiographic image in the memory 24, to thereby make it possible to specify the console 18 that performs the association.

The console process (see FIG. 13) executed by the console 18 is the same as in the first embodiment.

Fourth Embodiment

In the respective embodiments described above, the memory mode and the normal mode are described as the imaging mode. On the other hand, in a fourth embodiment, other imaging modes will be described.

Since a configuration (see FIGS. 1 and 2) of the radiographic image capturing system 10 of this embodiment is the same as in the first embodiment, detailed description thereof will not be repeated.

In this embodiment, as specific examples of other imaging modes in the radiographic image capturing apparatus 14, a power saving mode and a high speed mode will be described. The power saving mode refers to an imaging mode in which power consumption of the radiographic image capturing apparatus 14 is relatively reduced, which is an imaging mode in which the power consumption is reduced compared with that in a high speed mode.

On the other hand, the high speed mode refers to an imaging mode in which an imaging operation of a radiographic image can be performed at high speed, and an imaging mode in which irradiation starting with radiation R is determined at high speed compared with that in the power saving mode.

As described above, the radiographic image capturing apparatus 14 of this embodiment detects the irradiation starting with the radiation R using the host apparatus in an asynchronous manner with the irradiator 12. If the radiation detector 20 enters a ready state, the radiographic image capturing apparatus 14 performs an operation of detecting the irradiation starting with the radiation R. Thus, in the ready state, the power consumption increases compared with the standby state or the sleep state.

In the radiographic image capturing apparatus 14 of this embodiment, in the power saving mode, after positioning of a photographic subject W is terminated and starting of imaging is instructed from the control apparatus, the radiation detector 20 enters the ready state, and thus, the time in the ready state is shortened to reduce the power consumption as much as possible. On the other hand, in the high speed mode, in a case where the radiation detector 20 enters the ready state before the starting of imaging is instructed from the control apparatus, and if the starting of imaging is instructed, the mode is changed to a state where irradiation starting with radiation R can be immediately detected, to thereby perform the high speed operation.

In a case where the portable information terminal 16 is used as the control apparatus, generally, in many cases, imaging is performed at an imaging position where means for supplying source power to the radiographic image capturing apparatus 14 from the outside is not provided. Thus, in a case where the portable information terminal 16 is used as the control apparatus, the power saving mode in which the power consumption of the radiographic image capturing apparatus 14 can be reduced is suitable as the imaging mode.

On the other hand, in a case where the console 18 is used as the control apparatus, imaging is performed at an imaging position where means for supplying source power to the radiographic image capturing apparatus 14 from the outside is provided, such as a clinic of the department of radiology. Thus, in a case where the console 18 is used as the control apparatus, the high speed mode in which an operation can be operated at high speed is suitable as the imaging mode, compared with a case where the power consumption of the radiographic image capturing apparatus 14 is reduced.

Thus, in the radiographic image capturing apparatus 14 of this embodiment, in a case where the connected control apparatus is the portable information terminal 16, the power saving mode is selected as the imaging mode, and in a case where the connected control apparatus is the console 18, the high speed mode is selected as the imaging mode. In the radiographic image capturing apparatus 14 of this embodiment, in the case of the power saving mode, since the connected control apparatus is the portable information terminal 16, similar to the memory mode process of the first embodiment, generation and transmission of a preview image are performed, and a process of storing image data of radiographic images corresponding to plural orders in the memory 24 is also performed. Further, in the radiographic image capturing apparatus 14 of this embodiment, in the case of the high speed mode, since the connected control apparatus is the console 18, similar to the normal mode of the first embodiment, generation and transmission of a radiographic image for image reading are performed, and a process of storing image data of radiographic images corresponding to plural orders in the memory 24 is not performed.

An operation of the radiographic image capturing system 10 of this embodiment in a case of capturing a radiographic image will be described.

First, an operation of the radiographic image capturing apparatus 14 will be described. FIG. 20 is a flowchart illustrating an example of the flow of an imaging process executed by the imaging control unit 22 of the radiographic image capturing apparatus 14 of this embodiment. An overall flow of the imaging process executed by the radiographic image capturing apparatus 14 in this embodiment is the same as the imaging process (see FIG. 3) in the first embodiment. Thus, in FIG. 20, the same step numbers as in FIG. 3 are given to the steps of performing the same processes as in the imaging process shown in FIG. 3, and description thereof will not be repeated.

As shown in FIG. 20, in the imaging process of this embodiment, the imaging control unit 22 executes a power saving mode process of step S109, instead of the memory mode process in step S108 of the imaging process (see FIG. 3) in the first embodiment. Further, the imaging control unit 22 executes a high speed mode process in step S111 instead of the normal mode process in step S110 of the imaging process (see FIG. 3) in the first embodiment.

First, the power saving mode process will be described. In a case where the power saving mode process is performed (in a case where the imaging mode is the power saving mode), as described above, the connected control apparatus is the portable information terminal 16.

Figure 21:
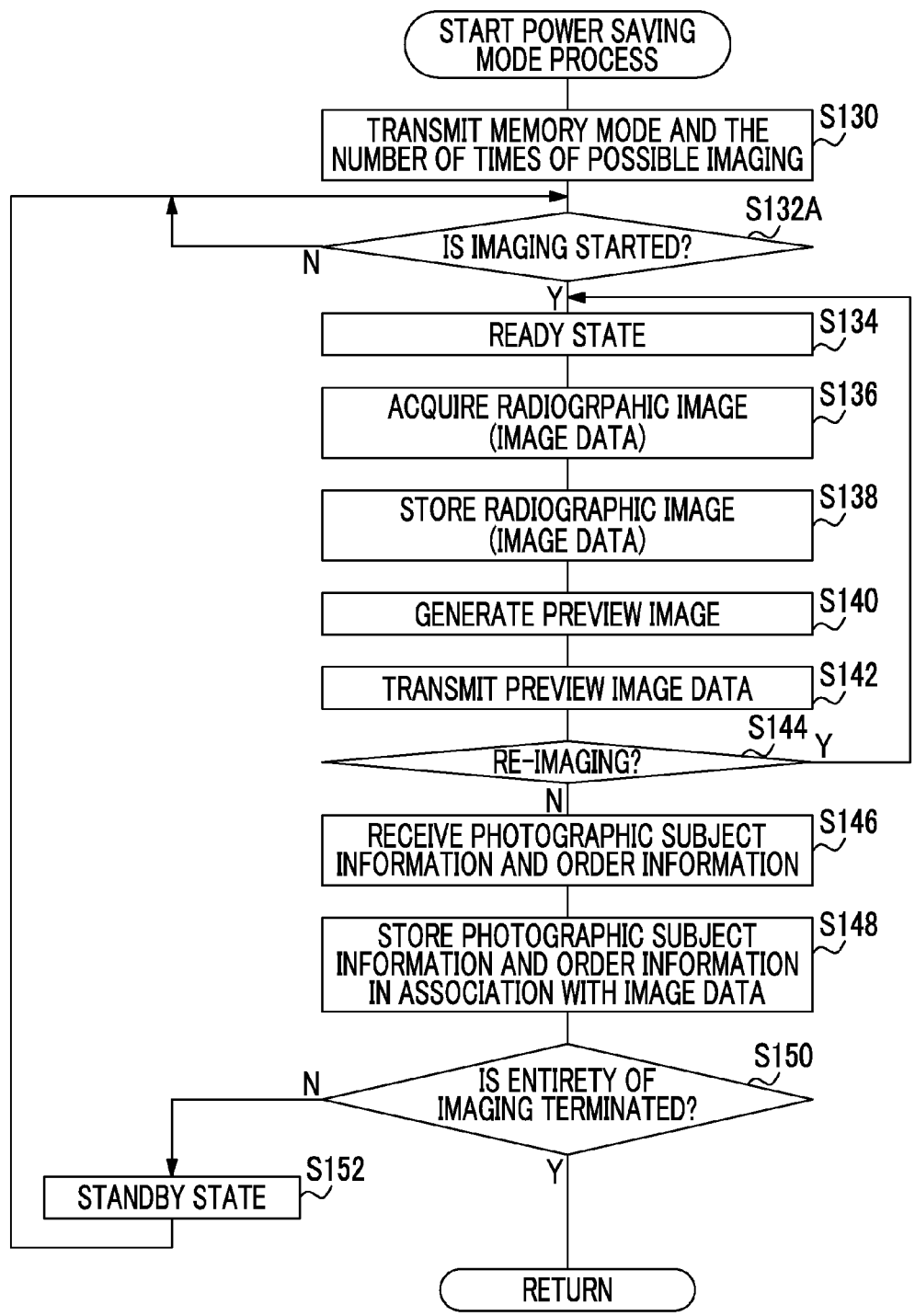
FIG. 21 is a flowchart illustrating an example of the flow of a power saving mode process executed by the imaging control unit of the radiographic image capturing apparatus of the fourth embodiment.

FIG. 21 is a flowchart illustrating an example of the flow of the power saving mode process executed by the imaging control unit 22 of the radiographic image capturing apparatus 14 of this embodiment.

The power saving mode process executed by the imaging control unit 22 of the radiographic image capturing apparatus 14 is different from the memory mode process (see FIG. 5) of the first embodiment in a determination method for determining that the imaging control unit 22 starts the capturing of the radiographic image. In step S132 of the memory mode process of the first embodiment, in a case where collation termination information is received, the imaging control unit 22 determines that the capturing of the radiographic image is started. On the other hand, in step S132A of the memory mode process of this embodiment, in a case where positioning termination information is received, the imaging control unit 22 determines that the capturing of the radiographic image is started.

As shown in FIG. 21, since processes executed in other respective steps are the same as in the memory mode process (see FIG. 5) of the first embodiment, description thereof will not be repeated.

On the other hand, FIG. 22 is a flowchart illustrating an example of the flow of a terminal process executed by the terminal control unit 30 of the portable information terminal 16 of this embodiment.

As shown in FIG. 22, the terminal process executed by the terminal control unit 30 of the portable information terminal 16 performs the same process as the terminal process in the first embodiment, except that steps S214A and 214B are executed instead of step S214 in the terminal process (see FIG. 8) of the first embodiment.

In step S214A, the terminal control unit 30 determines whether or not the positioning of the photographic subject W is terminated. If the photographic subject W matches a photographic subject W included in imaging list information, a user positions the photographic subject W. Alternatively, the user positions the photographic subject W and then performs collation of the photographic subject W.

The portable information terminal 16 of this embodiment causes the user to perform an operation of instructing termination of the positioning in order to determine whether or not the user terminates the positioning of the photographic subject W, and in step S214A, detects the operation of the user to determine whether or not the positioning of the photographic subject W is terminated.

Figure 23:
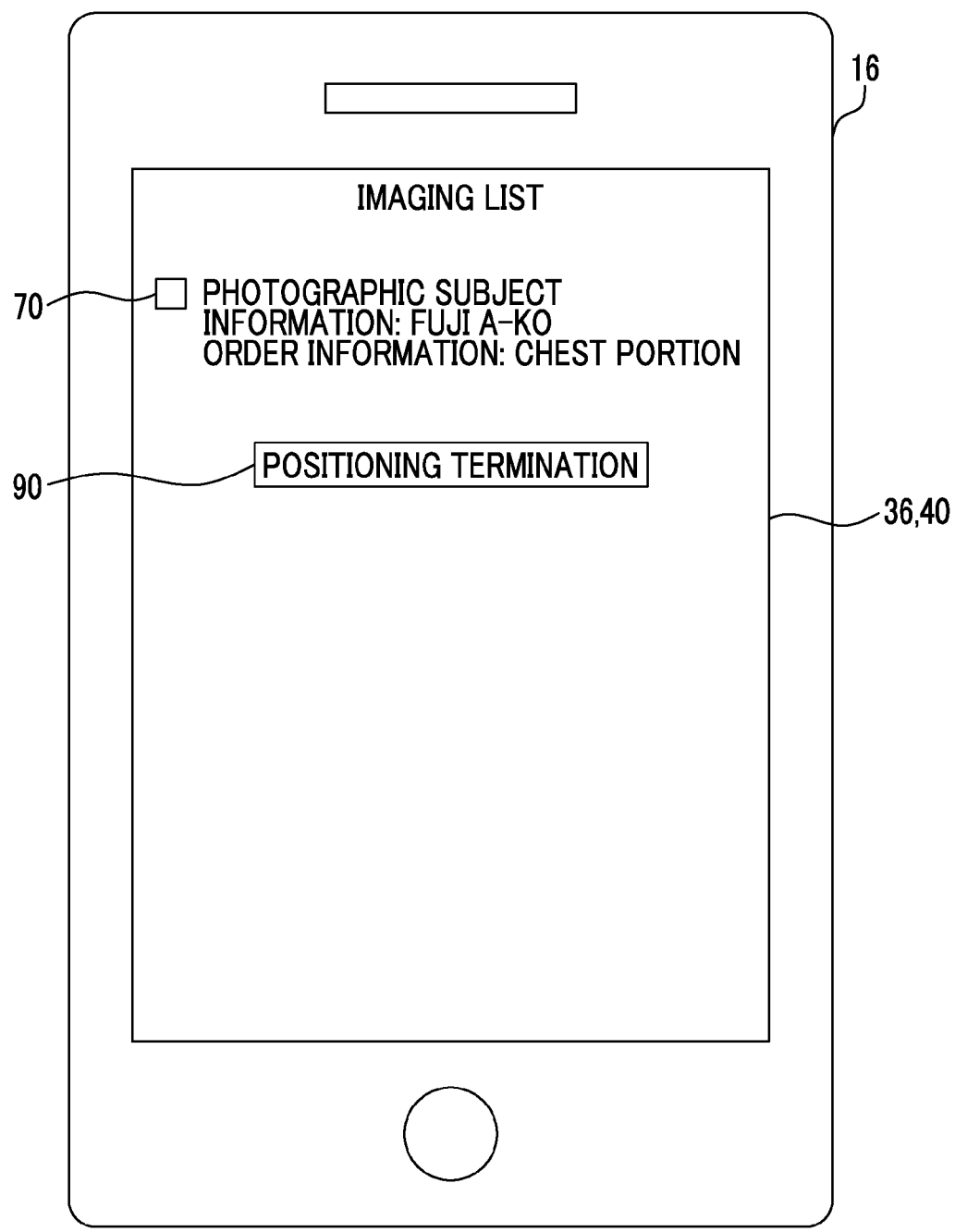
FIG. 23 is a schematic diagram illustrating a specific example of a state where a display for causing a user to perform an operation of instructing termination of positioning is performed on a display of a portable information terminal.

Thus, the terminal control unit 30 of the portable information terminal 16 of this embodiment performs a display for causing the user to perform the operation of instructing the positioning termination on the display 36. FIG. 23 is a schematic diagram illustrating a specific example of a state where the display for causing the user to perform the operation of instructing the positioning termination is performed on the display 36 of the portable information terminal 16. In FIG. 23, a state where content of an imaging list for which the imaging is being performed and an operating button 90 for instructing the positioning termination are displayed is shown.

If the positioning of the photographic subject W is terminated, the user operates the operating button 90 displayed on the display 36. The terminal control unit 30 detects that the operating button 90 is operated using the operation input detection unit 38. Further, the procedure waits until the terminal control unit 30 detects that the operating button 90 is operated by the user, and in a case where it is detected that the operating button 90 is operated, the procedure proceeds to step S214B.

In step S214B, the terminal control unit 30 transmits positioning termination information to the radiographic image capturing apparatus 14. The positioning termination information indicates that the positioning of the photographic subject W is terminated, corresponds to the collation termination information of the first embodiment, and includes information for instructing the radiographic image capturing apparatus 14 to capture a radiographic image.

As described above, in a case where the positioning termination information is received from the portable information terminal 16, the radiographic image capturing apparatus 14 determines that the capturing of the radiographic image is started (see step S132A in FIG. 21).

Further, similar to step S214 (see FIG. 5) in the memory mode process of the first embodiment, in step S214B, the terminal control unit 30 transmits imaging instruction information for a radiographic image to the irradiator 12 based on order information.

Next, the high speed mode process will be described. In a case where the high speed mode process is performed (in a case where the imaging mode is the high speed mode), as described above, the connected control apparatus is the console 18.

Figure 24:
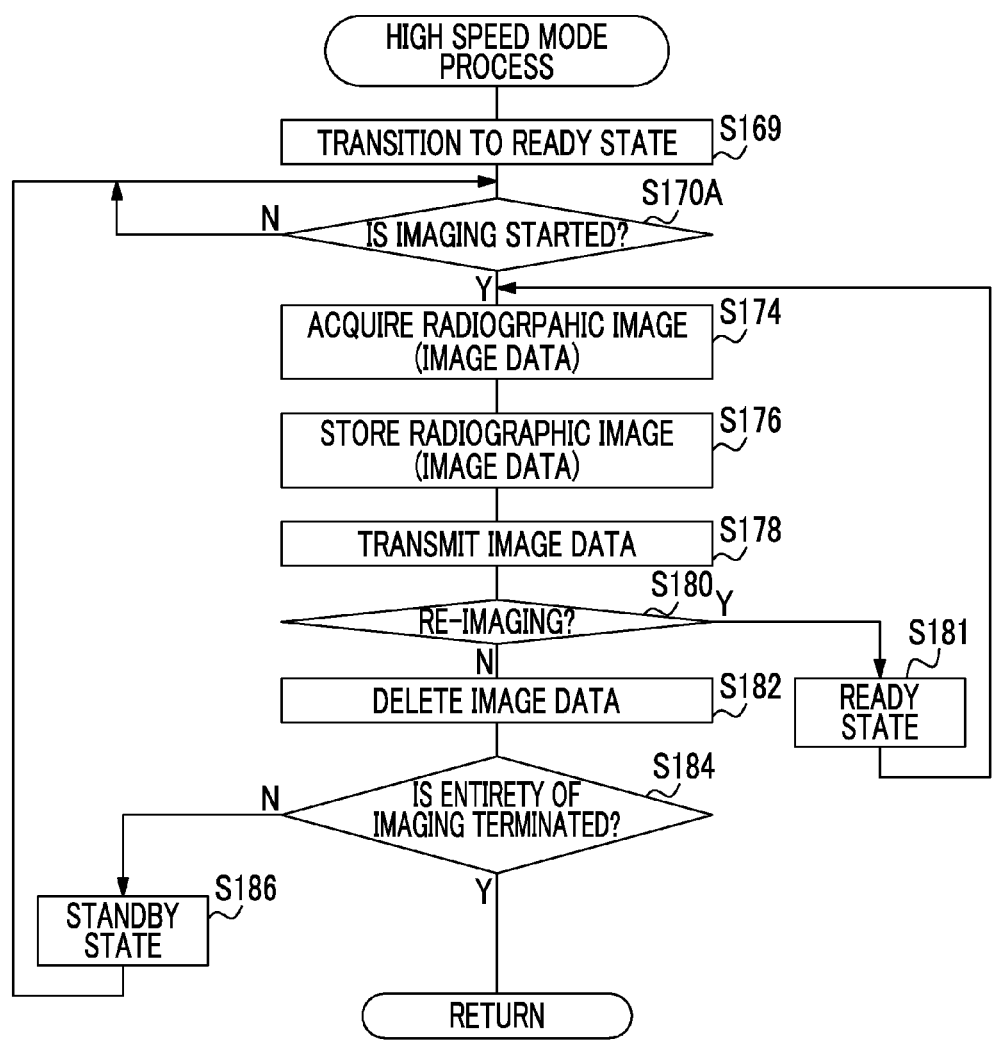
FIG. 24 is a flowchart illustrating an example of the flow of a high-speed mode process executed by an imaging control unit of the radiographic image capturing apparatus of the fourth embodiment.

FIG. 24 is a flowchart illustrating an example of the flow of the high-speed mode process executed by the imaging control unit 22 of the radiographic image capturing apparatus 14 of this embodiment.

In the high speed mode process of this embodiment, a timing when the control for causing the radiation detector 20 to enter the ready state is performed by the imaging control unit 22 is different from that in the memory mode process (see FIG. 5) of the first embodiment. Thus, in the high speed mode process of this embodiment, the imaging control unit 22 executes a process of step S169 corresponding to step S172 of the normal mode process (see FIG. 7) of the first embodiment immediately before step S170.

That is, if the high speed mode process is started, first, in step S169, the imaging control unit 22 performs the control for causing the radiation detector 20 to enter a ready state where detection of the radiation R can be immediately performed.

Then, in step S170A, the imaging control unit 22 determines whether or not capturing of a radiographic image is started. Here, a determination method for determining that the imaging control unit 22 starts the capturing of the radiographic image is the same as in step S132 of the power saving mode process (see FIG. 21).

As shown in FIG. 24, since processes executed in other respective steps are the same as in the normal mode process (see FIG. 7) of the first embodiment, description thereof will not be repeated.

On the other hand, FIG. 25 is a flowchart illustrating an example of the flow of a console process executed by the control unit 50 of the console 18 of this embodiment.

As shown in FIG. 25, the console process executed by the control unit 50 of the console 18 is the same process as the console process of the first embodiment, except that steps S308A and S308B are executed instead of step S308 in the console process (see FIG. 13) of the first embodiment.

Processes of step S308A and S308B are the same processes as in steps S214A and S214B, respectively, of the power saving mode process (see FIG. 21).

In step S308A, the control unit 50 determines whether or not the positioning of the photographic subject W is terminated, and waits until the determination is affirmative. If the determination is affirmative, the procedure proceeds to step S308B.

In step S308B, the control unit 50 transmits positioning termination information to the radiographic image capturing apparatus 14. If the positioning termination information is received from the console 18, the radiographic image capturing apparatus 14 determines that the capturing of the radiographic image is started (see step S170A in FIG. 24).

Further, in step S308B, the control unit 50 transmits imaging instruction information for a radiographic image to the irradiator 12 based on order information.

In this way, the radiographic image capturing apparatus 14 of this embodiment includes the power saving mode and the high speed mode as the imaging mode. In capturing the radiographic image, in a case where the connected control apparatus is the portable information terminal 16, the imaging control unit 22 of the radiographic image capturing apparatus 14 selects the power saving mode as the imaging mode. Further, in capturing the radiographic image, in a case where the connected control apparatus is the console 18, the imaging control unit 22 selects the high speed mode as the imaging mode.

Thus, in the radiographic image capturing apparatus 14 of this embodiment, it is possible to select the imaging mode suitable for the connected control apparatus.

The imaging mode is not limited to the imaging mode described in the present embodiment and the above-described embodiments. For example, the imaging mode may be a synchronous mode in which detection of radiation R is performed in synchronization with the irradiator 12 in the radiographic image capturing apparatus 14, or may be an asynchronous mode in which detection of radiation R is performed in an asynchronous manner with the irradiator 12.

Further, for example, the imaging mode may be an imaging mode depending on image quality of a radiographic image to be captured. In this case, as the imaging mode, for example, a definition mode which is an imaging mode in which a high-definition radiographic image is captured, a low noise mode in which the number of times of sampling of radiation R in the radiation detector 20 is increased to reduce noise, a sensitivity priority mode which is an imaging mode in which detection sensitivity of radiation R in the radiation detector 20 is preferentially considered, or the like may be used.

Fifth Embodiment

In the above-described embodiments, a case where the imaging mode is selected according to the image processing capacity of the control apparatus has been described. On the other hand, in a fifth embodiment, a case where the imaging mode is selected based on the image processing capacity of the control apparatus and the communication capacity between the radiographic image capturing apparatus 14 and the control apparatus will be described. Specifically, a case where the imaging mode is selected based on an evaluation result obtained by evaluating the image processing capacity and the communication capacity will be described.

In this embodiment, the "communication capacity" refers to a capacity based on at least one of communication standard, communication speed, traffic, stability, or the like, for example.

Since a configuration (see FIGS. 1 and 2) of the radiographic image capturing system 10 of this embodiment is the same as in the first embodiment, detailed description thereof will not be repeated.

The imaging control unit 22 of the radiographic image capturing apparatus 14 of this embodiment functions as an evaluation unit and a selection unit of the invention.

An operation of the radiographic image capturing system 10 of this embodiment in a case of capturing a radiographic image will be described.

Figure 27:
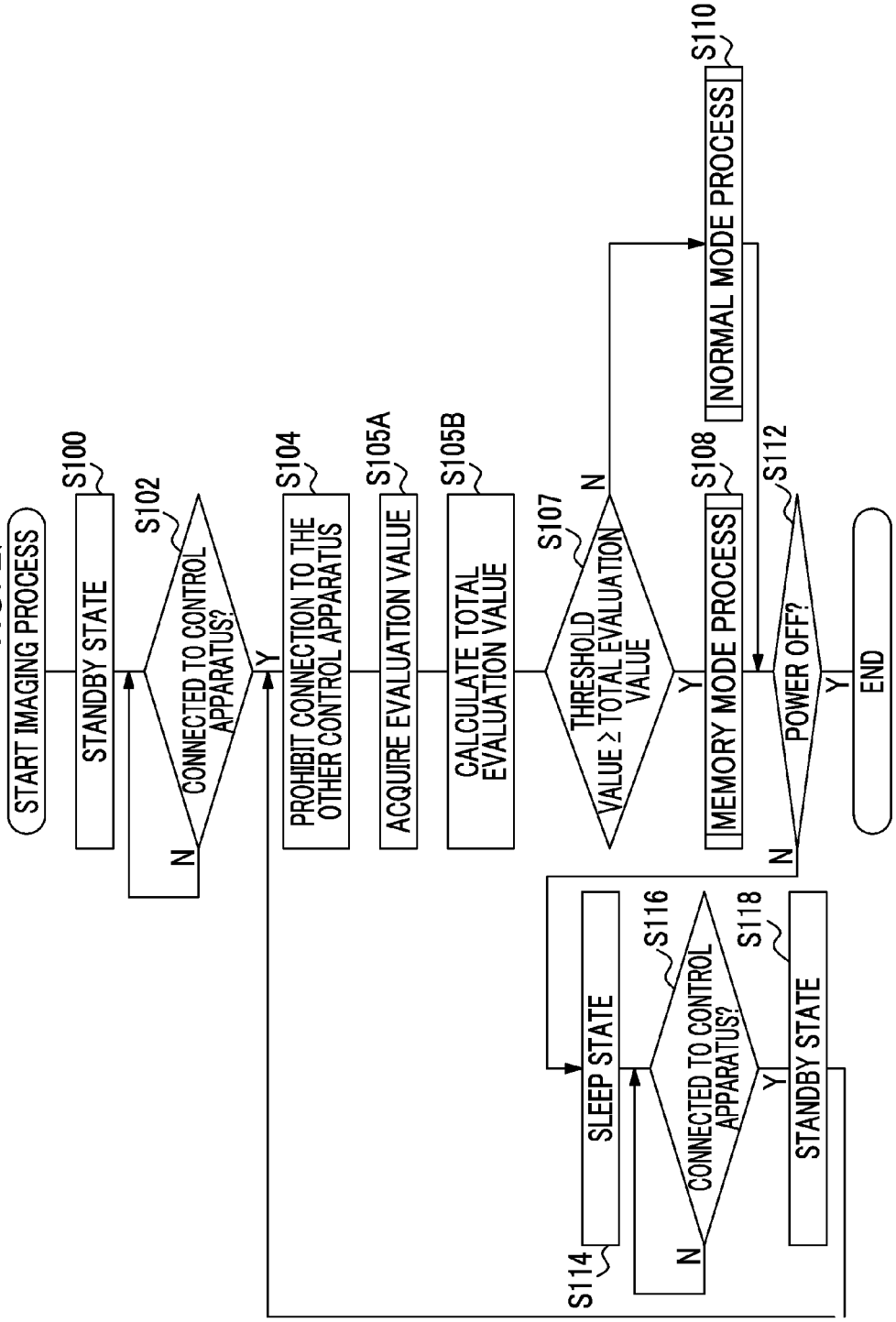
FIG. 27 is a flowchart illustrating an example of the flow of an imaging process executed by an imaging control unit of a radiographic image capturing apparatus of a fifth embodiment.

An operation of the radiographic image capturing apparatus 14 will be described. FIG. 27 is a flowchart illustrating an example of the flow of an imaging process executed by the imaging control unit 22 of the radiographic image capturing apparatus 14 of this embodiment. The imaging process executed by the radiographic image capturing apparatus 14 in this embodiment is the same as the imaging process (see FIG. 3) in the first embodiment in the entire flow. Thus, in FIG. 27, the same step numbers as in FIG. 3 are given to the steps of performing the same processes as in the imaging process shown in FIG. 3, and description thereof will not be repeated.

As shown in FIG. 27, in the imaging process of this embodiment, the imaging control unit 22 executes steps S105A and S105B after step S104 of the imaging process (see FIG. 3) in the first embodiment. Further, the imaging control unit 22 executes a process of step S107 instead of the memory mode process of step S106 in the imaging process (see FIG. 3).

In step S105A, the imaging control unit 22 acquires an evaluation value of the connected control apparatus. In this embodiment, the "evaluation value" refers to a value obtained by evaluating the image processing capacity and the communication capacity.

A specific example of the evaluation value will be described with reference to FIG. 28.

First, the evaluation value of the image processing capacity will be described. In the radiographic image capturing system 10 of this embodiment, as the evaluation value of the image processing capacity, an evaluation value is determined based on the image quality of a radiographic image capable of being displayed using the control apparatus. As shown in FIG. 28, the image quality of the radiographic image is determined in advance based on hardware of the control apparatus, and software used for image processing.

In a specific example shown in FIG. 28, the image quality of the radiographic image is determined in advance based on hardware of the control apparatus and software used for image processing, in which evaluation values A to C are determined in advance based on the image quality of the radiographic image. In the radiographic image capturing system 10 of this embodiment, the evaluation value of the image quality is as follows: A is the highest, and C is the lowest. Further, in the control apparatus that does not display a radiographic image, or in the control apparatus that cannot display a radiographic image, N is given as the evaluation value of the image quality.

The imaging control unit 22 of the radiographic image capturing apparatus 14 acquires the evaluation value of the image processing capacity based on hardware and software of the connected control apparatus. An acquisition method of the evaluation value of the image processing capacity is not particularly limited, but for example, as shown in the specific example in FIG. 28, a specific example of the evaluation value of the image processing capacity may be stored in the memory 24 in advance, information relating to the hardware and the software to be used may be acquired from the connected control apparatus, and an evaluation value corresponding to the acquired information may be acquired from the memory 24. Further, a correspondence relationship between identification information of the control apparatus and the evaluation value of the image processing capacity may be stored in the memory 24 in advance for each control apparatus, identification information of the host apparatus may be acquired from the connected control apparatus, and an evaluation value of the image processing capacity corresponding to the acquired identification information may be acquired from the memory 24.

Next, the evaluation value of the communication capacity will be described. As shown in FIG. 29, an applicable communication method for each control apparatus is determined in advance. In this embodiment, as a specific example, the evaluation value is determined in advance for each communication method, and the evaluation values respectively correspond to Wi-Fi MIMO (multiple input multiple output) (registered trademark), Wi-Fi (registered trademark), Bluetooth (registered trademark), Infrared Data Association (IrDA) (registered trademark), and near field communication (NFC). The evaluation value predetermined for each communication method is the highest in the case of Wi-Fi MIMO (registered trademark), and decreases in the order of Wi-Fi (registered trademark), Bluetooth (registered trademark), IrDA (registered trademark), and NFC. The communication methods are not limited to the methods described in this embodiment.

The imaging control unit 22 of the radiographic image capturing apparatus 14 acquires the evaluation value of the communication capacity based on the communication method for performing communication with the connected control apparatus. For example, a correspondence relationship between the communication method and the evaluation value of the communication capacity may be stored in the memory 24 in advance, and an evaluation value corresponding to the communication method for performing communication with the connected control apparatus may be acquired from the memory 24.

In the next step S105B, the imaging control unit 22 calculates a total evaluation value. The "total evaluation value" refers to an evaluation value calculated based on the evaluation value of the image processing capacity and the evaluation value of the communication capacity. As a specific example, the imaging control unit 22 of this embodiment sets a value obtained by adding the evaluation value of the image processing capacity to the evaluation value of the communication capacity as the total evaluation value. In a case of performing the addition, weighting may be performed with respect to any one of the evaluation value of the image processing capacity and the evaluation value of the communication capacity.

In the next step S107, the imaging control unit 22 determines whether or not the total evaluation value is equal to or lower than a predetermined threshold value for imaging mode selection. In the radiographic image capturing system 10 of this embodiment, as the total evaluation value is high, the normal mode is suitable as the imaging mode, and as the total evaluation value is low, the memory mode is suitable as the imaging mode. Thus, in the radiographic image capturing apparatus 14 of this embodiment, a threshold value for imaging mode selection is obtained in advance through an experiment or the like, and if the total evaluation value is equal to or lower than the threshold value for imaging mode selection, the memory mode is selected, and if the total evaluation value exceeds the threshold value for imaging mode selection, the normal mode is selected.

Thus, in a case where the determination in step S107 is affirmative, the procedure proceeds to step S108, and the imaging control unit 22 executes the above-described memory mode process. On the other hand, in a case where the determination is negative, the procedure proceeds to step S110, and the imaging control unit 22 executes the above-described normal mode process.

In this way, the radiographic image capturing apparatus 14 of this embodiment includes the I/F unit 28 and the imaging control unit 22 that function as a communication unit that selectively performs communication with any of the portable information terminal 16 and the console 18 which are plural control apparatuses that respectively perform a control relating to capturing of a radiographic image. Further, the radiographic image capturing apparatus 14 includes the imaging control unit 22 that functions as an evaluation unit that evaluates at least one of the image processing capacity, with respect to the radiographic image, of the control apparatus that performs communication with the communication unit, or the communication capacity through which the communication unit performs communication with the control apparatus, in a case of capturing the radiographic image, and a selection unit that selects any one of plural imaging modes predetermined with respect to the capturing of the radiographic image based on the evaluation result of the evaluation unit.

Thus, in the radiographic image capturing apparatus 14 of this embodiment, it is possible to select the imaging mode suitable for the connected control apparatus.

In the radiographic image capturing system 10 of this embodiment, the imaging mode is selected based on the total evaluation value obtained by the evaluation value of the image processing capacity and the evaluation value of the communication capacity, but the imaging mode may be selected based on any one of the evaluation value of the image processing capacity and the evaluation value of the communication capacity.

Further, the imaging mode may be selected using an evaluation value depending on a residual quantity of a storage unit provided in the control apparatus, or an evaluation value depending on a residual quantity of a battery (source power) of the control apparatus, in addition to the evaluation value of the image processing capacity and the evaluation value of the communication capacity. For example, in a case where the residual quantity of the storage unit provided in the control apparatus is small, since the memory mode is suitable as the imaging mode, an evaluation value that becomes small as the residual quantity of the storage unit is small may be determined in advance. Further, for example, in a case where the residual quantity of the battery of the control apparatus is small, the radiographic image capturing apparatus 14 and the portable information terminal 16 may be connected to each other using a communication method in which power consumption is reduced, and an evaluation value depending on the communication method may be acquired.

Further, the imaging mode may be selected using an evaluation value depending on the residual quantity of the memory 24 of the radiographic image capturing apparatus 14 or an evaluation value depending on the residual quantity of a battery (source power) of the control apparatus. For example, in a case where the residual quantity of the memory 24 is small, since the memory mode is suitable as the imaging mode, an evaluation value that becomes small as the residual quantity of the memory 24 is small may be determined in advance. Further, for example, in a case where the residual quantity of the battery of the control apparatus is small, the radiographic image capturing apparatus 14 and the portable information terminal 16 may be connected to each other using a communication method in which power consumption is reduced, and an imaging mode depending on the communication method may be acquired.

Further, the imaging mode may be selected using an evaluation value obtained by evaluating user operability (operation capability) with respect to the control apparatus, easiness in conveyance, or the like. For example, since the operability or the easiness in conveyance varies according to a connection state between a main body having a control function and a display unit such as a display, and a keyboard, the imaging mode may be selected using an evaluation value that varies according to the connection state. As a specific example, in a case where the main body having the control function and the display unit such as a display and the keyboard are not connected to each other, the evaluation value may be determined so that the memory mode is selected as the imaging mode.

Sixth Embodiment

In a sixth embodiment, a case where a video mode and a static image mode are provided as the imaging mode will be described.

In the case of the video mode, the radiation detector 20 continuously radiation at high speed (high frame rate) to capture radiographic images, compared with a case where static images are continuously captured, and transmits image data in real time.

Further, in this embodiment, in the case of the video mode, a wearable device may be used as the control apparatus.

Figure 30:
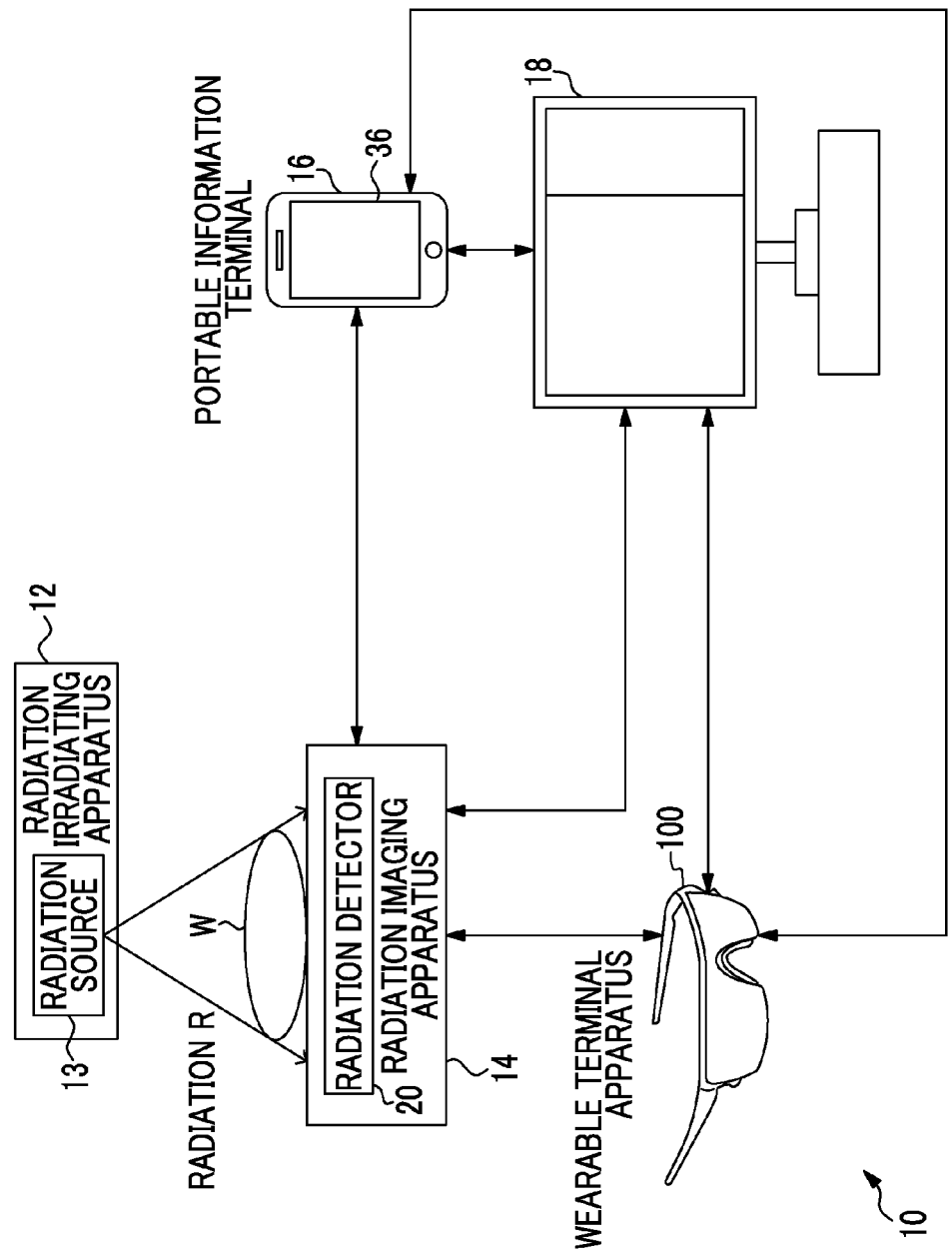
FIG. 30 is a schematic configuration diagram illustrating an example of a radiographic image capturing system of a sixth embodiment.

FIG. 30 is a schematic configuration diagram illustrating an example of a radiographic image capturing system of this embodiment. A radiographic image capturing system 10 of this embodiment is different from the radiographic image capturing system 10 of the first embodiment (see FIGS. 1 and 2) in that a wearable terminal 100 is provided as the wearable device.

The wearable terminal 100 is not particularly limited, and may be any type of wearable device which may be driven by a built-in battery. As a specific example of the wearable terminal 100, a spectacle-type computer such as smart glasses, a head mounted display (HMD), a timepiece-type computer, or the like may be used. Even a PDA such as a smart phone may be considered as the wearable device as long as it is a device capable of being worn by a user and capable of being driven by a built-in battery. The wearable terminal 100 of this embodiment is a device capable of being operated by a gesture such as a wink, voice, or the like without a user's contact with a device body of the wearable terminal 100.

As shown in FIG. 31, the wearable terminal 100 of this embodiment includes a wearable control unit 110, a display driver 112, a reader 113, a display 114, an operation input detection unit 116, an operation unit 118, an I/O unit 120, and an I/F unit 122. The wearable control unit 110, the display driver 112, the reader 113, the operation input detection unit 116, and the I/O unit 120 are connected to exchange a variety of information through a bus 127 such as a system bus or a control bus, for example.

The wearable control unit 110 has a function of controlling an overall operation of the wearable terminal 100.

The wearable control unit 110 includes a CPU, a ROM, and a RAM. The ROM stores in advance various processing programs including a wearable terminal process program (which will be described later) executed by the CPU, or the like. The RAM has a function of temporarily storing a variety of data.

The reader 113 of this embodiment has a function of reading a character, an image, or the like, or a function of imaging a person or the like. Specifically, the reader 113 has a camera function, and functions as a barcode reader.

The display 114 of this embodiment is an example of a display unit of the invention, and has a function of displaying a variety of information relating to imaging. The display driver 112 has a function of controlling display of the variety of information on the display 114.

The operation unit 118 is connected to the operation input detection unit 116, and is provided at a position where there is no interference when a radiographic image is captured in a housing (not shown) of the radiographic image capturing apparatus 14.

The operation unit 118 is used in a case where a user inputs an instruction relating to capturing of a radiographic image, a variety of information, or the like. As described above, the operation unit 118 may be operated by at least a gesture such as a wink, voice or the like. It is preferable that only a specific person such as a user who uses the wearable terminal 100 is able to perform an operation using the operation unit 118.

In this embodiment, the display 114 and the operation unit 118 are integrated to form a touch panel display. The operation input detection unit 116 has a function of detecting an operation state with respect to the operation unit 118.

The I/O unit 120 and the I/F unit 122 have a function for performing communication of a variety of information with the radiographic image capturing apparatus 14, the portable information terminal 16, and the console 18 through wireless communication using radio waves or light, or the like. The wearable terminal 100 of this embodiment uses short-range wireless communication in a case of performing communication with the radiographic image capturing apparatus 14, and uses wireless LAN communication in a case of performing communication with the console 18. Specifically, the wearable terminal 100 of this embodiment uses Bluetooth (registered trademark) in a case of performing communication with the radiographic image capturing apparatus 14, and uses Wi-Fi (registered trademark) in a case of performing communication with the console 18.

An operation of the radiographic image capturing system 10 of this embodiment in a case where a radiographic image is captured will be described.

An operation of the radiographic image capturing apparatus 14 will be described. FIG. 32 is a flowchart illustrating an example of the flow of an imaging process executed by the imaging control unit 22 of the radiographic image capturing apparatus 14 of this embodiment. The imaging process executed by the radiographic image capturing apparatus 14 in this embodiment is the same as the imaging process (see FIG. 27) in the fifth embodiment in the entire flow. Thus, in FIG. 32, the same step numbers as in FIG. 32 are given to the steps of performing the same processes as in the imaging process shown in FIG. 27, and description thereof will not be repeated.

As shown in FIG. 32, in the imaging process of this embodiment, the imaging control unit 22 executes processes of steps S108A and step S110A instead of steps S108 and S110 in the fifth embodiment.

In this embodiment, similar to the fifth embodiment, an imaging mode is selected according to a threshold value. In this embodiment, in the case of a video mode, since image data of plural radiographic images is continuously transmitted to a control apparatus, the video mode is selected in a case where the communication capacity is relatively high. Thus, the threshold value for video mode selection is obtained in advance through an experiment or the like. Here, if a total evaluation value is equal to or lower than the threshold value for the video mode selection, a static image mode is selected, and if the total evaluation value exceeds the threshold value for the video mode selection, the video mode is selected. The relationship between the threshold value in the video mode selection and the total evaluation value is not limited to this embodiment. For example, there is a case where the video image may have image quality lower than that of the static image. In such a case, in a case where the image processing capacity is relatively low, the video mode may be selected. In this case, a threshold value for video mode selection may be obtained in advance through an experiment or the like, and then, if a total evaluation value is equal to or lower than the threshold value for the video mode selection, the video mode is selected, and if the total evaluation value exceeds the threshold value for the video mode selection, the static image mode may be selected. Further, which one of the image processing capacity and the communication capacity is preferentially used may be set, and the relationship between the threshold value in the video mode selection and the total evaluation value may be determined according to the preferentially used capacity.

In a static image mode process in step S108A, it is sufficient if capturing of a static image is captured, and other processes are not particularly limited. For example, any one of the memory mode and the normal mode described in the above embodiments may be executed. Further, for example, similar to the fifth embodiment, any one of the memory mode and the normal mode may be selected in advance based on a total evaluation value and a threshold value for imaging mode selection by an experiment or the like, for execution.

On the other hand, in step S110A, the video mode process (an example thereof is shown in FIG. 33) is executed. As shown in FIG. 33, since the video mode process of this embodiment includes the same process as the normal mode process in the first embodiment, the same reference numerals are given to the same processes, and detailed description thereof will not be repeated.

As shown in FIG. 33, in the video mode process, steps S166 and S168 are executed before step S170.

In step S166, the imaging control unit 22 determines whether or not the wearable terminal 100 controls the radiographic image capturing apparatus 14. That is, the imaging control unit 22 determines whether or not the wearable terminal 100 performs controls (various instructions or the like) performed from a control device with respect to capturing of a radiographic image. For example, in a case where the wearable terminal 100 performs communication with the radiographic image capturing apparatus 14, in a case where setting for performing control in the wearable terminal 100 is performed in advance, or in a case where an instruction for the setting is received, the determination becomes affirmative. In a case where the determination is affirmative, the procedure proceeds to step S168.

In step S168, the imaging control unit 22 prohibits reception of an instruction from the control apparatus. Specifically, the imaging control unit 22 prohibits reception of a control instruction relating to imaging from the portable information terminal 16 or the console 18 connected as the control apparatus, and notifies the connected control apparatus of a message thereof. A method for prohibiting the reception of the control instruction relating to the imaging in the radiographic image capturing apparatus 14 is not particularly limited, and thus, reception of a signal from the control apparatus may be prohibited, or a received signal may be ignored to be discarded.

In this way, in a case where the reception of the instruction from the control apparatus is prohibited, the radiographic image capturing apparatus 14 performs capturing of a radiographic image under the control of the wearable terminal 100.

Then, in step S172A, the imaging control unit 22 performs a control for causing the radiation detector 20 to enter a ready state which is a state where detection of radiation R can be immediately performed. In this embodiment, the wearable terminal 100 instructs the irradiator 12 to capture a radiographic image. Thus, the irradiator 12 performs irradiation with the radiation R in a case where imaging instruction information for a radiographic image transmitted from the wearable terminal 100 is received.

Under the control of the wearable terminal 100 and the imaging control unit 22, the radiation detector 20 detects the radiation R that is emitted from the irradiator 12 and passes through the photographic subject W, to thereby capture the radiographic image depending on the photographic subject W. In this embodiment, in order to perform capturing of a video image, the radiation detector 20 continuously captures radiographic images at predetermined frame rate. Thus, whenever image data of plural radiographic images depending on the frame rate is captured, the image data is sequentially output from the radiation detector 20.

After the radiographic images are captured by the radiation detector 20, in the next step S174A, the imaging control unit 22 sequentially acquires plural pieces of image data (video image data) output from the radiation detector 20. In the next step S176A, the imaging control unit 22 sequentially stores the acquired plural pieces of image data (video image data) in the memory 24.

In the next step S178A, the imaging control unit 22 sequentially transmits the image data (video image data) of the radiographic images to the connected control apparatus.

Further, in the radiographic image capturing system 10 of this embodiment, in a case where a user who confirms the video image displayed on the control apparatus desires re-imaging, the user may instruct the re-imaging by the wearable terminal 100.

In this way, in the case of the video mode, since the video image data is transmitted to the control apparatus from the radiographic image capturing apparatus 14 according to the capturing of the radiographic images, the control apparatus can display the radiographic images which form the video images in real time.

On the other hand, the wearable terminal 100 executes a wearable terminal process (an example thereof is shown in FIG. 34). A wearable control unit 110 executes a wearable terminal processing program stored in a ROM thereof, to thereby execute the wearable terminal process.

In step S400 in FIG. 34, the wearable control unit 110 connects the host apparatus to the radiographic image capturing apparatus 14. Specifically, the wearable control unit 110 performs communication with the radiographic image capturing apparatus 14, to thereby connect the host apparatus to the radiographic image capturing apparatus 14. In this way, as the radiographic image capturing apparatus 14 and the wearable terminal 100 are connected to each other, it is possible to control the radiographic image capturing apparatus 14 by the wearable terminal 100.

In the next step S408, the wearable control unit 110 performs collation of the photographic subject W. Here, the wearable control unit 110 reads, as photographic subject information, a photographic subject name disclosed in a name tag of the photographic subject W, a medical record card, or the like, a bar code, and a two-dimensional code such as a QR code (registered trademark), and the like using the reader 113, and collates the read data with imaging list information, to thereby perform the collation of the photographic subject W. Further, for example, in a case where a photo image including the face of the photographic subject W is included in the imaging list information, the terminal control unit 30 may take a picture of the face of the photographic subject W using the reader 33, and may perform face recognition or the like using an image of the photographed face, for example, to thereby perform the collation of the photographic subject W. In this way, the collation method of the photographic subject W is not particularly limited, and any method capable of collating the photographic subject W to be photographed with the imaging list information may be used. In addition, fingerprint recognition or the like may be used. The imaging list may be acquired from the control apparatus or the like. Further, the collation may be performed using the control apparatus or the like, and the wearable terminal 100 may transmit the photographic subject information read by the reader 113 to the control apparatus, and receive the collation result from the control apparatus.

In the next step S410, the wearable control unit 110 determines whether or not the photographic subject W matches a photographic subject W included in the imaging list information, based on the collation result in the process of step S408. In a case where the determination is negative, the procedure proceeds to step S411.

In step S411, the wearable control unit 1100 displays information indicating non-match on the display 114.

On the other hand, in a case where the determination is affirmative, the procedure proceeds to step S414. In step S414, the wearable control unit 110 transmits collation termination information to the radiographic image capturing apparatus 14. In this embodiment, the collation termination information represents that the collation of the photographic subject W is terminated, and includes information for instructing the radiographic image capturing apparatus 14 to capture a radiographic image.

Further, in step S414, the wearable control unit 110 transmits imaging instruction information for a radiographic image to the irradiator 12 based on order information. The order information may be acquired from the control apparatus or the like.

In the radiographic image capturing apparatus 14, the video image is captured, and the captured video image is displayed using the control apparatus. The user confirms the video image, and determines whether or not to perform re-imaging. In a case of performing the re-imaging, the user instructs the re-imaging using the operation unit 118. A method for instructing the re-imaging is not particularly limited, but for example, in a case where the wearable terminal 100 is the spectacle-type computer, a method for instructing the re-imaging using a wink may be used.

In a case where the determination in step S420 is affirmative, the procedure proceeds to step S422. After the wearable control unit 110 transmits re-imaging instruction information to the radiographic image capturing apparatus 14, the procedure returns to step S420.

On the other hand, in a case where the determination is negative, the procedure proceeds to step S424. In step S424, the wearable control unit 110 transmits imaging completion instruction information to the radiographic image capturing apparatus 14, and then, the procedure proceeds to step S426.

In step S426, the terminal control unit 30 transmits at least one of photographic subject information or order information to the radiographic image capturing apparatus 14.

In the next step S430, the terminal control unit 30 determines whether or not the entirety of imaging included in the imaging list is terminated. In a case where it is determined that the entirety of imaging is not terminated, the procedure returns to step S408 to repeat the wearable terminal process. On the other hand, in a case where it is determined that the entirety of imaging is terminated, the procedure proceeds to step S432.

In step S432, the wearable control unit 110 transmits termination instruction information to the radiographic image capturing apparatus 14. In the next step S424, the wearable control unit 110 releases the connection to the radiographic image capturing apparatus 14, and then, terminates the wearable terminal process. Specifically, the wearable control unit 110 cuts off (terminates) the communication with the radiographic image capturing apparatus 14, to thereby release the connection to the radiographic image capturing apparatus 14.

Next, an operation of the control apparatus of this embodiment will be described. As a specific example, a case where the control apparatus connected to the radiographic image capturing apparatus 14 is the portable information terminal 16 will be described.

The portable information terminal 16 executes the terminal process (an example thereof is shown in FIG. 35). Since the terminal process shown in FIG. 35 is a process similar to the terminal process (FIG. 8) of the first embodiment, the same reference numerals are given to the same processes, and detailed description thereof will not be repeated.

In the terminal process shown in FIG. 35, step S200 of the terminal process (FIG. 8) of the first embodiment is removed, and step S203 is added between step S202 and step S204.

In step S203, the terminal control unit 30 determines whether or not control is prohibited. As a specific example, in a case where the control with respect to the radiographic image capturing apparatus 14 is not prohibited by the process of step S168 of the video mode process (see FIG. 33), the determination becomes negative, and the procedure proceeds to step S204.

Then, in steps S216 and S218 of the terminal process (FIG. 8) of the first embodiment, a preview image is received and displayed, but in this embodiment, instead of the preview image in steps S216A and S218B, a video image is received and is displayed on the display 36.

Further, in the terminal process of this embodiment, step S228 of the terminal process (FIG. 8) of the first embodiment is removed.

On the other hand, in a case where the determination in step S203 is affirmative, the procedure proceeds to step S231A. Step S231A and the next step S231B are the same processes as step S216A, step S218B, and step S218A. That is, the video image is received and is displayed on the display 36.

In the next step S231C, the terminal control unit 30 determines whether or not to terminate the process. In a case where imaging completion instruction information is not received from the wearable terminal 100, the determination becomes negative, and the procedure returns to step S231A. On the other hand, in a case where the imaging completion instruction information is received, the determination becomes affirmative, and the procedure proceeds to step S234.

In this way, in the radiographic image capturing system 10 of this embodiment, in a case where the video mode is selected as the imaging mode, the radiographic image capturing apparatus 14 can be controlled by the wearable terminal 100. Further, since the video image is displayed on the control apparatus, it is possible to confirm the video image by the control apparatus.

According to the radiographic image capturing system 10 of this embodiment, it is possible to perform an instruction with respect to the radiographic image capturing apparatus 14 by using the wearable terminal 100 without operating the operation unit 40 of the portable information terminal 16. Thus, even in a case where the portable information terminal 16 is disposed at a space that a user cannot reach, it is easy to perform an instruction with respect to the radiographic image capturing apparatus 14. Accordingly, it is possible to enhance usability of the radiographic image capturing apparatus for a user.

Further, generally, in many cases, the portable information terminal 16 such as a tablet terminal is used in a medical field. For example, as described above, there is a case where a surgical operation is performed while displaying a radiographic image which is a video image on the display 36 of the portable information terminal 16 in real time. Further, for example, there is a case where a 3D image obtained by performing image processing with respect to an image captured by computed tomography (CT) or magnetic resonance imaging (MRI) in advance is displayed on the display 36 of the portable information terminal 16 and a surgical operation is performed while confirming a stereoscopic positional relationship of organs or blood vessels.

In the medical field, in a case where a user performs an operation while touching the operation unit 40 provided in the device body of the portable information terminal 16, such as an operation using a touch panel, there is a high concern that germs attached to the operation unit 40 are attached to the user.

Thus, generally, as described above, in a case where the portable information terminal 16 is used in the medical field, by sealing the portable information terminal 16 using a sterilized plastic bag or the like, or by providing a sterilized cover or the like to the portable information terminal 16, it is possible to perform the operation without a user's direct touch with the operation unit 40 provided in the device body of the portable information terminal 16.

In this regard, in this embodiment, as the wearable terminal 100 is used as the control apparatus, the user's operation becomes easy, and it is not necessary that the user touches the operation unit 40 of the portable information terminal 16. Thus, it is possible to relieve the effort of the user, for example, for sealing the portable information terminal 16 using the sterilized plastic bag as described above.

Further, in the wearable terminal 100, the operation may be simply operated using a gesture such as a wink. Further, in a case where the wearable terminal 100 has a function of a digital camera or the like, it is possible to simply capture a digital image as well as a radiographic image. In the medical field, the captured image may be very usefully used for confirmation of a medical practice or the like in the future.

Further, since the image captured by the wearable terminal 100 which is the spectacle-type computer is an image captured by the user's eye, it is possible to efficiently use the image for an educational purpose with respect to a doctor or the like having little experience.

In addition, in this embodiment, since the wearable terminal 100 may be operated using a gesture (for example, a wink), it is possible to rapidly perform the operation.

In this embodiment, the display of the video image is performed by the control apparatus, but the display of the video image may be performed by both of the control apparatus and the wearable terminal 100, instead of the control apparatus.

Further, in this embodiment, in the case of the video mode, the entire control of the radiographic image capturing apparatus 14 is performed from the wearable terminal 100, but the wearable terminal 100 may perform only a predetermined control, and the control apparatus connected to the radiographic image capturing apparatus 14 may perform other controls.

In this embodiment, in the case of the video mode, the capturing of only the video image is performed, but capturing of a static image may be performed. For example, the wearable terminal 100 may instruct the radiographic image capturing apparatus 14 to capture a static image, or the capturing of the static image may be performed before or after capturing of the video image, or at a predetermined timing.

Further, in this embodiment, the video mode is selected as the imaging mode based on the total evaluation value and the threshold value for video mode selection, but a method for selecting the video mode as the imaging mode is not limited to this embodiment.

A configuration in which the radiographic image capturing apparatus 14 is controlled by the wearable terminal 100 is not limited to this embodiment. For example, the wearable terminal 100 may be used as the same control apparatus as the portable information terminal 16 or the console 18.

Further, the type of the control performed by the wearable terminal 100 with respect to the radiographic image capturing apparatus 14 is not limited to this embodiment. For example, the wearable terminal 100 may instruct which mode the imaging mode is set to. As a specific example, after positioning of the photographic subject W is terminated, the wearable terminal 100 may instruct the radiographic image capturing apparatus 14 to transition to the power saving mode.

In addition, an antibacterial technique may be applied to an outer surface of the wearable terminal 100. Furthermore, an antibacterial technique that includes a hydrophilic processing unit disclosed in JP2015-27416A may be used. Thus, even in a case where the outer surface of the wearable terminal 100 is contaminated by a body fluid or the like, it is possible to easily remove the contamination.

As described above, the radiographic image capturing apparatus 14 of the respective embodiments includes the I/F unit 28 and the imaging control unit 22 that function as a communication unit that selectively performs communication with any one of the portable information terminal 16 and the console 18 which are plural control apparatuses that have different image processing capacities with respect to a radiographic image and respectively perform a control relating to capturing of the radiographic image, and the imaging control unit 22 that functions as a selection unit that selects any one of plural imaging modes (the memory mode and the normal mode) predetermined with respect to the capturing of the radiographic image based on the image processing capacity of a control apparatus that performs communication with the communication unit in a case of capturing the radiographic image.

Further, the imaging control unit 22 exclusively selects the plural imaging modes for each control apparatus according to the image processing capacities of the plural control apparatuses.

Thus, according to the radiographic image capturing apparatus 14 of this embodiment, it is possible to select the imaging mode suitable for the connected control apparatus in the radiographic image capturing apparatus 14.

Further, according to the radiographic image capturing apparatus 14 of this embodiment, in a case where the portable information terminal 16 is connected, the memory mode is selected as the imaging mode. Thus, according to the radiographic image capturing apparatus 14, even in a case where the communication with the console 18 or an external system cannot be performed due to communication troubles, it is possible to appropriately and reliably capture a radiographic image, and to prevent a user's operation from being complicated. Further, in the case of the console 18, in order to start the imaging, about several minutes are necessary for start-up such as reception of order information. However, since the portable information terminal 16 needs only about 1 minute for the start-up, the start-up becomes fast, and even in a case where the imaging is urgently performed, it is possible to quickly, appropriately, and reliably execute capturing of a radiographic image.

Accordingly, according to the radiographic image capturing apparatus 14 of the respective embodiments, it is possible to enhance usability of the radiographic image capturing apparatus 14 for a user.

Further, in the radiographic image capturing apparatus 14 of the first to third embodiments, in a case where the portable information terminal 16 is connected, the memory mode is selected as the imaging mode, and the image data of the radiographic image obtained by the imaging is stored in the memory 24 of the radiographic image capturing apparatus 14. Thus, it is possible to perform imaging regardless of the capacity of the storage unit 32 of the portable information terminal 16. Further, since the radiographic image capturing apparatus 14 can be handled by the user, similar to a radiographic image capturing apparatus that performs capturing of a radiographic image using a film or a computed radiography (CR) cassette, it is possible to enhance usability of the radiographic image capturing apparatus 14 for the user.

Figure 26:
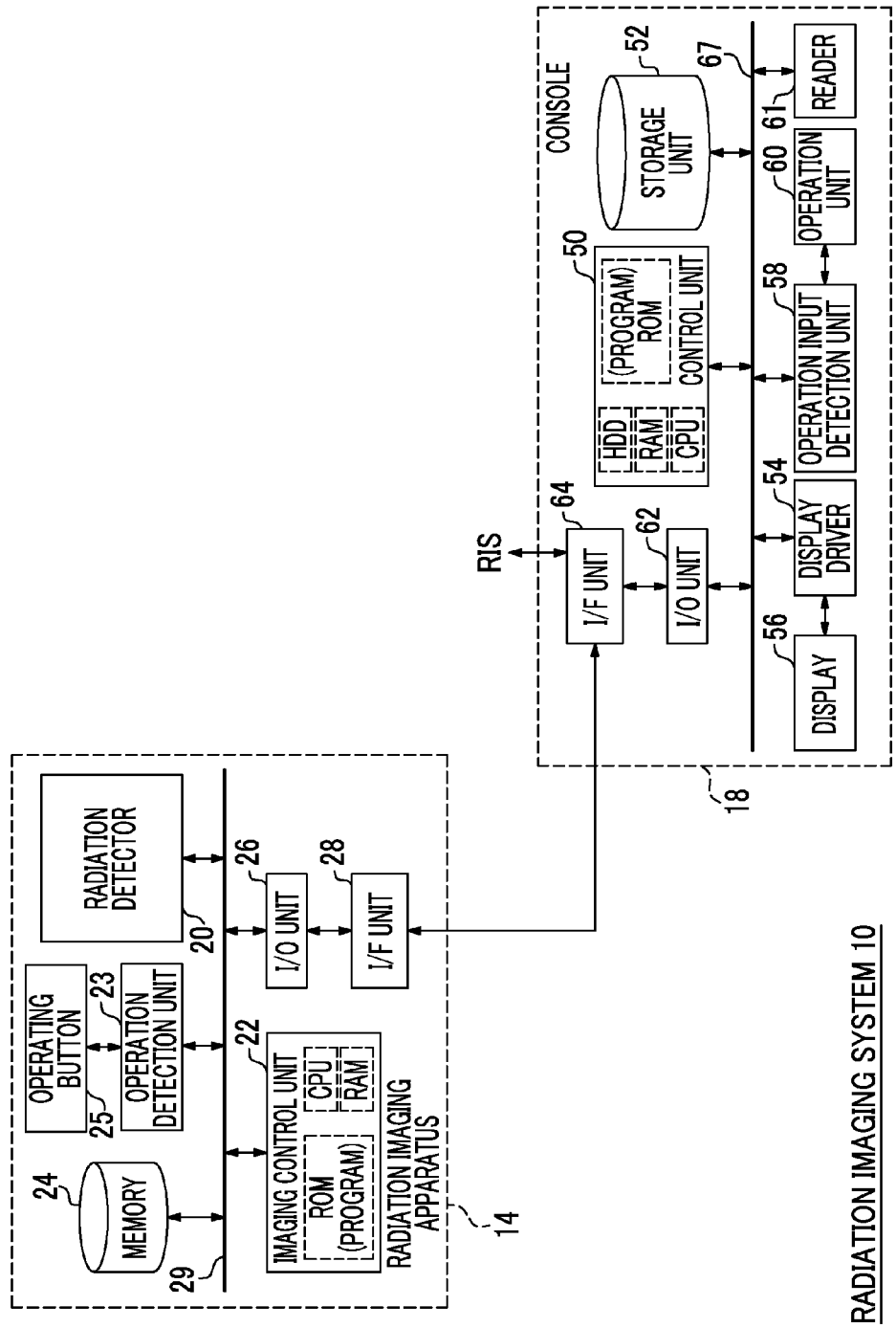
FIG. 26 is a schematic configuration diagram illustrating an example of a radiographic image capturing system that includes a radiographic image capturing apparatus and a console.

The radiographic image capturing system 10 may include only one control apparatus capable of being connected to the radiographic image capturing apparatus 14. As such a case, FIG. 26 shows a schematic configuration of an example of the radiographic image capturing system 10 that includes the radiographic image capturing apparatus 14 and the console 18. The radiographic image capturing system 10 shown in FIG. 26 does not include the portable information terminal 16, differently from the radiographic image capturing system 10 of the first embodiment (see FIGS. 1 and 2).

Even in the case of one control apparatus, in a case where the control apparatus has image processing functions having different image processing capacities with respect to a radiographic image, in which any one of the functions is selectable, each image processing function can be equivalently considered as one control apparatus, and the radiographic image capturing apparatus 14 can be used for imaging similar to the above-described respective embodiments.

As a specific example, it is assumed that the console 18 is a control apparatus that includes a first image processing function of performing offset correction, gain correction, and defective pixel correction, and a second image processing function of performing offset correction and gain correction. In this case, in a case of performing the first image processing function, the control unit 50 may be considered as the same control apparatus as the console 18 described in the above-described respective embodiments. Further, in a case of performing the second image processing function, the control unit 50 may be considered as the same control apparatus as the portable information terminal 16 described in the above-described respective embodiments.

The imaging control unit 22 of the radiographic image capturing apparatus 14 shown in FIG. 26 selects an imaging mode according to which one of the first image processing function and the second image processing function the image processing function executed by the control unit 50 of the console 18 corresponds to. In the imaging control unit 22, a method for determining which one of the first image processing function and the second image processing function the image processing function executed by the control unit 50 of the console 18 corresponds to is not particularly limited. For example, in the radiographic image capturing apparatus 14, a correspondence relationship between each of the first image processing function and the second image processing function, and an imaging mode is stored in advance in the memory 24 or the like. Further, the imaging control unit 22 of the radiographic image capturing apparatus 14 may acquire information indicating which function the image processing function executed by the control unit 50 corresponds to from the console 18, and may select an imaging mode based on the acquired information and the stored correspondence relationship.

Further, even in the case of one control apparatus, in a case where the one control apparatus has plural image processing functions by using an image processing function of a system, an apparatus or the like provided in an external system or the like, similarly, each image processing function can be equivalently considered as one control apparatus, and the radiographic image capturing apparatus 14 can be used for imaging similar to the above-described respective embodiments. As a specific example, it is assumed that the portable information terminal 16 can perform image processing of a radiographic image obtained by imaging using the image processing function of the host apparatus and the image processing function of the console 18. In this case, in a case of performing image processing using the image processing function of the console 18, the imaging control unit 22 may be considered as the same control apparatus as the console 18. Further, in a case of performing image processing using the image processing function of the host apparatus, the imaging control unit 22 may be considered as the same control apparatus as the portable information terminal 16 described in the respective embodiments. In the imaging control unit 22, a method for determining which one of the image processing function of the portable information terminal 16 or the image processing function of the console 18 the image processing function used by the portable information terminal 16 corresponds to is not particularly limited. For example, the imaging control unit 22 may acquire information indicating which of the image processing function used by the portable information terminal 16 corresponds to, and may select an imaging mode based on the acquired information.

In the above-described respective embodiments, a case where the portable information terminal 16 and the console 18 having different image processing functions as image processing capacities are used as the control apparatuses is described, but the image processing capacities are not limited to the image processing functions. For example, the image processing capacities may be display capacities of display units provided in the control apparatuses. In the case of the radiographic image capturing system 10 of the respective embodiments, display capacities of the display 36 of the portable information terminal 16 and the display 56 of the console 18 are different from each other. Here, the "display capacity" refers to a capacity depending on at least one of the size of a display region where a radiographic image is displayed, resolution, gradation, or the like.

As a specific example, in the radiographic image capturing apparatus 14, in a case where a display region of the connected control apparatus is equal to or smaller than a predetermined size, since it may be difficult to display a radiographic image for image reading in the control apparatus, the memory mode described in the first to third embodiments is set as the imaging mode. On the other hand, in the radiographic image capturing apparatus 14, in a case where the display region of the connected control apparatus exceeds a predetermined size, since it is possible to display the radiographic image for image reading in the control apparatus, the normal mode described in the first to third embodiments is set as the imaging mode.

In this case, in the radiographic image capturing apparatus 14, a correspondence relationship between information (control apparatus ID or the like) indicating each control apparatus and the size of the display region is stored in advance in the memory 24 or the like. Further, a control apparatus ID may be acquired from the connected control apparatus, and the size of the display region may be determined based on the acquired control apparatus ID and the stored correspondence relationship, and the imaging mode may be selected depending on the determined size of the display region.

In this case, as an example of the predetermined size of the display region, the size of a tablet terminal may be used. As a specific example, a 10-inch tablet (corresponding to a diagonal length of 25 cm) may be used as the size of a screen, for example.

Further, as a specific example, in a case where the resolution of the radiographic image capturing apparatus 14 is equal to or less than a predetermined resolution, since it may be difficult to see the radiographic image for image reading displayed in the control apparatus, the memory mode described in the first to third embodiments is set to the imaging mode. On the other hand, in the radiographic image capturing apparatus 14, in a case where the resolution of the connected control apparatus exceeds a predetermined resolution, since it is easy to see the radiographic image for image reading displayed in the control apparatus, the normal mode described in the first to third embodiments is set as the imaging mode.

In the above-described respective embodiments, the imaging mode is selected whenever the radiographic image capturing apparatus is connected to the control apparatus, but the timing when the imaging mode is selected is not particularly limited. For example, the imaging mode may be selected for every order information or every photographic subject W. The imaging mode may be selected according to predetermined conditions, for example, conditions set according to a user's desire. In a case where capturing of plural radiographic images is instructed by one piece of order information, it is preferable that the capturing corresponding to one piece of order information is performed in the same imaging mode.

Further, in a case of performing additional imaging, a doctor or the like who requests additional imaging with respect to a user for whom capturing of a photographic image is necessary may urgently desire to read the radiographic image. In such a case, it is preferable that the imaging mode is set to the normal mode and image data of the radiographic image is stored in the control apparatus. Further, in a case where the reading of the radiographic image is not urgent, it may be preferable that the imaging mode is set to the memory mode. Thus, the imaging mode may be selected according to the additional imaging.

In the above-described respective embodiments, the radiographic image capturing apparatus 14 automatically selects the memory mode in a case where the portable information terminal 16 is connected, and the normal mode in a case where the console 18 is connected, but the selection of the imaging mode may be performed based on an imaging mode instructed by the user. For example, in a case where the portable information terminal 16 is connected to the radiographic image capturing apparatus 14, if it is detected that the operation unit 40 of the portable information terminal 16 is operated by a user, the portable information terminal 16 transmits selection information for selecting the memory mode to the radiographic image capturing apparatus 14. Further, the imaging control unit 22 functions as an example of a reception unit of the invention, and selects the memory mode as the imaging mode based on the received selection information.

In this case, the user may perform the instruction of the imaging mode from any apparatus. For example, as described above, the instruction of the imaging mode may be performed from any one of the portable information terminal 16 (operation unit 40), the console 18 (operation unit 60), and the radiographic image capturing apparatus 14 (operating button 25). Further, the instruction of the imaging mode may be performed from an external system which is directly or indirectly connected to the radiographic image capturing apparatus 14.

Further, the timing when the user performs the instruction of the imaging mode is not particularly limited, and for example, may be a timing when the imaging list described in the respective embodiments is displayed, or may be a timing before imaging corresponding to one piece of order information is started. Further, the instruction of the imaging mode may be performed every order information.

The radiographic image capturing apparatus 14 of the above-described respective embodiments may set the instructed imaging mode in the memory 24 or the like using a flag or the like.

Further, similar to the instruction of the imaging mode, the radiographic image capturing apparatus 14 may release an imaging mode which is being executed by an instruction of the user. In this case, the radiographic image capturing apparatus 14 may transition to a predetermined imaging mode.

In addition, in a case where the radiographic image capturing apparatus 14 and the control apparatus perform communication in a wired manner, the imaging mode may be selected according to predetermined conditions regardless of the above-described respective embodiments. For example, in a case where the communication is performed in a wired manner, since the communication capacity is greater than that in a case where the communication is performed in a wireless manner, the normal mode may be selected as the imaging mode. However, since the imaging is performed in an imaging environment where the communication cannot be performed in a wireless manner, in a case where the communication is performed in a wired manner, for example, even in a case where the portable information terminal 16 is used as the control apparatus, it is preferable that the memory mode is selected as the imaging mode.

Further, in the radiographic image capturing apparatus 14 of the above-described respective embodiments, in a case where the memory mode process is performed, it is preferable that in a case where the connection (communication) with the portable information terminal 16 is cut off, the memory mode is maintained as the imaging mode, and in a case where the connection (communication) is restored, the memory mode process is performed again.

In the above-described respective embodiments, a case where the radiographic image capturing apparatus 14 includes two kinds of imaging modes is described, but three or more kinds of imaging modes may be provided. For example, in a case where capturing of a radiographic image is performed using the portable information terminal 16, there is a case where although an empty capacity of the memory 24 of the radiographic image capturing apparatus 14 is insufficient, the capturing of the radiographic image is to be performed using the portable information terminal 16. In this case, it is not appropriate for the imaging control unit 22 of the radiographic image capturing apparatus 14 to select the memory mode as the imaging mode. With respect to the imaging mode, it is preferable that a third mode of generating image data of a preview image and transmitting the image data to the portable information terminal 16 and transmitting raw data of a radiographic image or image data of a radiographic image for image reading to the portable information terminal 16 is provided as the imaging mode, and in the above case, the imaging control unit 22 selects the third mode as the imaging mode.

In the radiographic image capturing system 10 of the above-described respective embodiments, a case where the portable information terminal 16 and the console 18 are provided as plural control apparatuses is described, but the control apparatuses provided in the radiographic image capturing system 10 are not limited thereto. For example, plural portable information terminals 16 may be provided in one radiographic image capturing system 10.

In this case, the plural portable information terminals 16 may include a portable information terminal to which the memory mode is applied as described above, and a portable information terminal to which the normal mode is applied in a similar to the console 18. As a specific example, in a case where the portable information terminal 16 in which OsiriX which is image processing software is applied to an image processing function is used in combination with the console 18, the memory mode is applied similar to the portable information terminal 16 of the first to third embodiments. On the other hand, in a case where the portable information terminal 16 in which OsiriX is applied to the image processing function and a portable information terminal 16 having an image processing function with an image processing capacity lower than that of OsiriX are combined for use, the normal mode is applied similar to the console 18 of the first to third embodiments. Information for determining which imaging mode is selected according to the portable information terminal 16 may be registered in the radiographic image capturing apparatus 14.

In the above-described respective embodiments, a case where image data of a radiographic image or an image ID is stored in association with at least one of photographic subject information or order information is described, but it is preferable that other information may be stored in association.

For example, irradiation result information indicating a result obtained by irradiating the radiographic image capturing apparatus 14 with radiation R from the irradiator 12 may be associated. As a specific example of the information indicating the result, a tube current, a tube voltage, an irradiation time, an irradiation region (opening region of a collimator), and the like may be used. In capturing a radiographic image, imaging may be performed without using a grid for removing scattered rays generated in a case where the radiation R passes through a photographic subject W, and then, a virtual grid process of removing the influence of the scattered rays based on a characteristic of a grid to be used, similar to a case where a grid is provided using image processing with respect to image data of the captured radiographic image, may be performed. Since the amount of scattered rays corresponds to the dose of the emitted radiation R, by associating the information indicating the result, it is possible to enhance the accuracy of the virtual grid process with respect to the image data of the associated radiographic image.

Further, for example, information indicating whether or not imaging is performed using a grid may be associated. In this case, it is possible to determine whether or not the virtual grid process is performed with respect to the image data of the associated radiographic image.

In addition, for example, information (user ID or the like) indicating a user who performs imaging may be associated.

For example, information indicating an upper side and a lower side (top and bottom) of a radiographic image may be associated. In this case, in a case where the user reads the associated radiographic image, it is possible to automatically adjust the upper side and the lower side (top and bottom) of the radiographic image by an apparatus used for reading.

Further, for example, information (imaging apparatus ID or the like) indicating the radiographic image capturing apparatus 14 may be associated.

For example, information indicating an apparatus of a transmission source of order information or a system (for example, console ID or the like in the case of the console 18) may be associated. In this case, it is possible to easily transmit the associated radiographic image to the transmission source of order information.

Further, for example, in a case where imaging is performed in a state where an order is not issued, for example, in additional imaging, information indicating that the order is not issued may be associated. In this case, it is possible to easily associate image data of a radiographic image with order information using the console 18 or the like.

Further, in the first to third embodiments, a case where when imaging starting is instructed from the control apparatus, the radiographic image capturing apparatus 14 causes the radiation detector 20 to enter a ready state to detect irradiation starting with radiation R is described, but a timing when the radiation detector 20 enters the ready state is not limited thereto. For example, a temperature sensor may be provided in the radiographic image capturing apparatus 14, and the imaging control unit 22 may determine that a photographic subject W is positioned and is in contact with the radiographic image capturing apparatus 14 based on a change in temperature detected by the temperature sensor. Further, in a case where it is determined that the photographic subject W is positioned and is in contact with the radiographic image capturing apparatus 14, the radiation detector 20 may enter the ready state. Further, for example, a sensor for detecting a state of the radiographic image capturing apparatus 14 in a case where imaging is started may be provided, and in a case where it is determined by the imaging control unit 22 that the imaging is started based on a detection result of the sensor, the radiation detector 20 may enter the ready state.

In the first to third embodiments, in the case of the normal mode, a case where image data of a radiographic image is temporarily stored in the memory 24 until imaging corresponding to one piece of order information is completed, and if the imaging corresponding to one order is completed, the image data is collectively deleted is described, but a timing when the image data is deleted is not limited thereto. For example, whenever imaging completion instruction information is received from the console 18, the image data may be deleted one by one.

Further, in the above-described respective embodiments, a case where when the console 18 receives image data of a radiographic image, the image data is stored in the storage unit 52 in the console 18 is described, but a position where the information is stored is not limited to the storage unit 52. For example, the information may be stored in an external storage device (PACS: picture archiving and communication system), or the like.

Further, the photographic subject W may not be a human, and may be a creature other than a human, such as an animal or a plant, or may be other objects.

In addition, radiation R used for capturing of a radiographic image is not particularly limited, and X-rays, γ-rays, or the like may be applied.

Furthermore, the configurations and operations of the radiographic image capturing apparatus 14, the portable information terminal 16, the console 18, and the like described in the embodiments are examples, and may be variously modified according to situations in a range without departing from the spirit of the invention.

What is claimed is:

1. A radiographic image capturing apparatus comprising:
a communication unit that selectively performs communication with any one of a plurality of control apparatuses that has different image processing capacities with respect to a radiographic image and respectively performs a control relating to capturing of the radiographic image; and
a selection unit that selects any one of a plurality of imaging modes predetermined with respect to the capturing of the radiographic image according to the image processing capacity of the control apparatus that performs communication with the communication unit in a case of capturing the radiographic image.

2. The radiographic image capturing apparatus according to claim 1,
wherein the plurality of imaging modes includes a plurality of imaging modes that varies according to the image processing capacities, and
the selection unit exclusively selects any one of the plurality of imaging modes for each of the control apparatuses, according to the image processing capacities of the plurality of control apparatuses.

3. The radiographic image capturing apparatus according to claim 1,
wherein the plurality of control apparatuses include a control apparatus having an image processing capacity, among the plurality of control apparatuses, lower than those of the other control apparatuses,
the plurality of imaging modes includes a memory mode which is an imaging mode in which image data of a plurality of radiographic images obtained by imaging is stored in a storage unit integrated with the radiographic image capturing apparatus, and
the selection unit selects the memory mode in a case where the communication unit performs communication with the control apparatus having an image processing capacity, among the plurality of control apparatuses, lower than those of the other control apparatuses.

4. The radiographic image capturing apparatus according to claim 3,
wherein the storage unit is detachably and attachably mounted to the radiographic image capturing apparatus.

5. The radiographic image capturing apparatus according to claim 3,
wherein the image data of the plurality of radiographic images is image data of radiographic images obtained based on a plurality of order information, and image data of the plurality of radiographic images obtained based on one piece of order information is associated with each other and stored in the storage unit.

6. The radiographic image capturing apparatus according to claim 1,
wherein a control apparatus having an image processing capacity, among the plurality of control apparatuses, higher than those of the other control apparatuses has a predetermined image processing function of generating a radiographic image for image reading, and a control apparatus having an image processing capacity lower than those of the other control apparatuses does not have the predetermined image processing function.

7. The radiographic image capturing apparatus according to claim 1,
wherein a control apparatus having an image processing capacity, among the plurality of control apparatuses, higher than those of the other control apparatuses has a display unit capable of displaying a radiographic image for image reading, and a control apparatus having an image processing capacity lower than those of the other control apparatuses has a display unit incapable of displaying the radiographic image for image reading.

8. The radiographic image capturing apparatus according to claim 1,
wherein each of the plurality of control apparatuses includes a display unit having a display capacity according to the image processing capacity, and
the selection unit selects any one of the plurality of predetermined imaging modes according to the display capacity of the display unit.

9. The radiographic image capturing apparatus according to claim 8,
wherein the display capacity includes the size of a display region of the display unit,
the plurality of imaging modes includes a memory mode which is an imaging mode in which image data of a plurality of radiographic images obtained by imaging is stored in a storage unit integrated with the radiographic image capturing apparatus, and
the selection unit selects the memory mode in a case where the communication unit performs communication with the control apparatus having the display unit in which the size of the display region is equal to or smaller than a predetermined size.

10. The radiographic image capturing apparatus according to claim 1,
wherein the selection unit further selects any one of the plurality of imaging modes predetermined with respect to the capturing of the radiographic image, according to a communication capacity through which the communication unit performs communication with the control apparatus.

11. The radiographic image capturing apparatus according to claim 1,
wherein the plurality of imaging modes includes a video mode which is an imaging mode in which a video image is captured,
the radiographic image capturing apparatus further comprising:
a permission unit that permits, in a case where the selection unit selects the video mode, a wearable device to execute at least a part of the control relating to the capturing of the radiographic image, performed by the control apparatus that performs communication with the communication unit.

12. The radiographic image capturing apparatus according to claim 1,
wherein the plurality of control apparatuses include a control apparatus having an image processing capacity, among the plurality of control apparatuses, higher than those of the other control apparatuses,
the plurality of imaging modes includes a normal mode which is an imaging mode in which image data of a plurality of radiographic images obtained by imaging is sequentially transmitted, and
the selection unit selects the normal mode in a case where the communication unit performs communication with the control apparatus having an image processing capacity, among the plurality of control apparatuses, higher than those of the other control apparatuses.

13. The radiographic image capturing apparatus according to claim 1, wherein the plurality of imaging modes includes a normal mode in which image data of a plurality of radiographic images obtained by imaging is sequentially transmitted, and a memory mode in which the image data of the plurality of radiographic images is stored in a storage unit integrated with the radiographic image capturing apparatus, and the selection unit selects the memory mode in a case where the communication unit performs communication with a control apparatus having an image processing capacity, among the plurality of control apparatuses, lower than those of the other control apparatuses.

14. The radiographic image capturing apparatus according to claim 1, further comprising:

a reception unit that receives a setting of the imaging mode, wherein the selection unit selects any one of the plurality of predetermined imaging modes based on the setting received by the reception unit.

15. A radiographic image capturing system comprising:

the radiographic image capturing apparatus according to claim 1; and a plurality of control apparatuses that has different image processing capacities with respect to a radiographic image obtained by imaging in the radiographic image capturing apparatus and respectively performs a control relating to capturing of the radiographic image.

16. A control method of the radiographic image capturing apparatus according to claim 1, comprising:

selectively performing communication with any one of the plurality of control apparatuses that has different image processing capacities with respect to the radiographic image and respectively performs a control relating to capturing of the radiographic image; and selecting any one of the plurality of imaging modes predetermined with respect to the capturing of the radiographic image according to the image processing capacity of the control apparatus with which the communication is performed in a case of capturing the radiographic image.

17. A non-transitory computer readable recording medium recorded with a control program of the radiographic image capturing apparatus according to claim 1, causing a computer to execute a process comprising:

selectively performing communication with any one of the plurality of control apparatuses that has different image processing capacities with respect to the radiographic image and respectively performs a control relating to capturing of the radiographic image; and selecting any one of the plurality of imaging modes predetermined with respect to the capturing of the radiographic image according to the image processing capacity of the control apparatus with which the communication is performed in a case of capturing the radiographic image.

18. A radiographic image capturing apparatus comprising:

a communication unit that selectively performs communication with any one of a plurality of control apparatuses that respectively performs a control relating to capturing of a radiographic image;

an evaluation unit that evaluates at least one selected from a group including an image processing capacity, with respect to the radiographic image, of the control apparatus that performs communication with the communication unit and a communication capacity through which the communication unit performs communication with the control apparatus, in a case of capturing the radiographic image; and a selection unit that selects any one of a plurality of imaging modes predetermined with respect to the capturing of the radiographic image based on an evaluation result of the evaluation unit.

19. The radiographic image capturing apparatus according to claim 18, wherein the plurality of imaging modes includes a video mode which is an imaging mode in which a video image is captured, the radiographic image capturing apparatus further comprising:

a permission unit that permits, in a case where the selection unit selects the video mode, a wearable device to execute at least a part of the control relating to the capturing of the radiographic image, performed by the control apparatus that performs communication with the communication unit.

20. The radiographic image capturing apparatus according to claim 19, wherein in a case where the permission unit gives permission to the wearable device, the communication unit transmits the radiographic image to the control apparatus that communicates with the communication unit, among the control apparatus that communicates with the communication unit and the wearable device.

21. A radiographic image capturing apparatus comprising:

a communication unit that performs communication with a control apparatus that has a plurality of image processing functions having different image processing capacities with respect to a radiographic image, in which any one of the functions is selectively executed, and performs a control relating to capturing of the radiographic image; and a selection unit that selects any one of a plurality of imaging modes predetermined with respect to the capturing of the radiographic image according to the function executed by the control apparatus, among the plurality of functions, in a case of capturing the radiographic image.

22. A radiographic image capturing system comprising:

the radiographic image capturing apparatus according to claim 18; and wherein the control apparatus has a first and a second image processing functions having different image processing capacities with respect to a radiographic image obtained by imaging in the radiographic image capturing apparatus, in which any one of the functions is selectively executed, and performs a control relating to capturing of the radiographic image.

* * * * *